US012677331B2

(12) United States Patent    (10) Patent No.:   US 12,677,331 B2

Al-Ali et al.    (45) Date of Patent:    Jul. 7, 2026

(54) TRANSFERRING WIRELESS MONITORING WITH REDUCED DATA LOSS

(71) Applicant: MASIMO CORPORATION, Irvine, CA (US)

(72) Inventors: Ammar Al-Ali, San Juan Capistrano, CA (US); Austin Kretz Pike, Laguna Niguel, CA (US); Richard Priddell, Irvine, CA (US); Christopher Robert Magers, Vista, CA (US); Omar Ahmed, Lake Forest, CA (US)

(73) Assignee: Masimo Corporation, Irvine, CA (US)

( * ) Notice: Subject to any disclaimer, the term of this patent is extended or adjusted under 35 U.S.C. 154(b) by 72 days.

(21) Appl. No.: 18/365,008

(22) Filed: Aug. 3, 2023

(65) Prior Publication Data

US 2024/0047061 A1    Feb. 8, 2024

Related U.S. Application Data

(60) Provisional application No. 63/370,637, filed on Aug. 5, 2022.

(51) Int. Cl.
   *H04W 76/10*      (2018.01)
   *A61B 5/00*      (2006.01)
       (Continued)

(52) U.S. Cl.
   CPC ............. *H04W 76/10* (2018.02); *A61B 5/002* (2013.01); *A61B 5/681* (2013.01); *G06F 3/011* (2013.01);
       (Continued)

(58) Field of Classification Search
   CPC ... H04W 76/10; H04W 12/009; H04W 12/06; H04W 4/80; A61B 5/002; A61B 5/681;
       (Continued)

(56) References Cited

U.S. PATENT DOCUMENTS

| 4,960,128 A | 10/1990 | Gordon et al. |
| 4,964,408 A | 10/1990 | Hink et al. |

(Continued)

FOREIGN PATENT DOCUMENTS

| WO | WO 2021/231326 | 11/2021 |
| WO | WO 2024/031019 | 2/2024 |

OTHER PUBLICATIONS

US 2024/0016391 A1, 01/2024, Lapotko et al. (withdrawn)

(Continued)

*Primary Examiner* — Jeff Piziali

(74) *Attorney, Agent, or Firm* — Knobbe, Martens, Olson & Bear, LLP

(57) ABSTRACT

A monitoring hub can monitor a health status of a subject having a wireless wearable device. The monitoring hub can access wireless configuration data received from a remote server. The monitoring can establish wireless communication with the wearable device, based on the wireless configuration data, to wirelessly receive real-time physiological data from the wearable device. The monitoring hub can receive historical physiological data from the remote server. The historical physiological data comprising physiological data collected by the wearable device and/or communicated from the wearable device to another monitoring hub before establishing the wireless communication between the monitoring hub and the wearable device. The monitoring hub can generate user interface data for rendering a user interface including the real-time physiological data in combination with the historical physiological data to reduce a gap in monitoring between the historical physiological data and the real-time physiological data.

10 Claims, 42 Drawing Sheets

500C

- 543 Receive request to establish physiological monitoring
- 545 Access wireless configuration data
- 547 Establish wireless communication with sensor(s) based on wireless configuration data
- 549 Receive real-time physiological data originating from sensor(s) via wireless communication
- 551 Receive historical physiological data from remote computing device
- 553 Generate user interface data to display indicia of real-time physiological data and historical physiological data

(51) Int. Cl.

| | |
|---|---|
| *G06F 3/01* | (2006.01) |
| *G16H 40/20* | (2018.01) |
| *G16H 40/67* | (2018.01) |
| *H04B 5/77* | (2024.01) |
| *H04W 12/00* | (2021.01) |
| *H04W 12/06* | (2021.01) |
| *G16H 10/60* | (2018.01) |

(52) U.S. Cl.
CPC ............. *G16H 40/20* (2018.01); *G16H 40/67* (2018.01); *H04B 5/77* (2024.01); *H04W 12/009* (2019.01); *H04W 12/06* (2013.01); *G16H 10/60* (2018.01)

(58) Field of Classification Search
CPC ... A61B 5/7445; A61B 5/022; A61B 5/14551; A61B 5/6822; A61B 5/6826; A61B 5/0006; A61B 5/0022; A61B 5/0024; A61B 5/256; A61B 5/282; A61B 5/339; A61B 5/6823; A61B 5/7435; A61B 5/0002; A61B 5/6813; G06F 3/011; G06F 1/1601; G06F 1/1626; G06F 1/1632; G06F 1/165; G06F 1/1671; G06F 1/1698; G06F 1/203; G06F 2200/1633; G06F 1/1633; G16H 40/20; G16H 40/67; G16H 10/60; G16H 40/63; H04B 5/77
See application file for complete search history.

(56) References Cited

U.S. PATENT DOCUMENTS

| | | | |
|---|---|---|---|
| 5,319,355 | A | 6/1994 | Russek |
| 5,337,744 | A | 8/1994 | Branigan |
| 5,341,805 | A | 8/1994 | Stavridi et al. |
| D353,195 | S | 12/1994 | Savage et al. |
| D353,196 | S | 12/1994 | Savage et al. |
| 5,377,676 | A | 1/1995 | Vari et al. |
| D359,546 | S | 6/1995 | Savage et al. |
| 5,431,170 | A | 7/1995 | Mathews |
| 5,436,499 | A | 7/1995 | Namavar et al. |
| D361,840 | S | 8/1995 | Savage et al. |
| D362,063 | S | 9/1995 | Savage et al. |
| D363,120 | S | 10/1995 | Savage et al. |
| 5,456,252 | A | 10/1995 | Vari et al. |
| 5,479,934 | A | 1/1996 | Imran |
| 5,482,036 | A | 1/1996 | Diab et al. |
| 5,494,043 | A | 2/1996 | O'Sullivan et al. |
| 5,533,511 | A | 7/1996 | Kaspari et al. |
| 5,561,275 | A | 10/1996 | Savage et al. |
| 5,590,649 | A | 1/1997 | Caro et al. |
| 5,602,924 | A | 2/1997 | Durand et al. |
| 5,638,816 | A | 6/1997 | Kiani-Azarbayjany et al. |
| 5,638,818 | A | 6/1997 | Diab et al. |
| 5,645,440 | A | 7/1997 | Tobler et al. |
| 5,671,914 | A | 9/1997 | Kalkhoran et al. |
| 5,726,440 | A | 3/1998 | Kalkhoran et al. |
| D393,830 | S | 4/1998 | Tobler et al. |
| 5,743,262 | A | 4/1998 | Lepper, Jr. et al. |
| 5,747,806 | A | 5/1998 | Khalil et al. |
| 5,750,994 | A | 5/1998 | Schlager |
| 5,758,644 | A | 6/1998 | Diab et al. |
| 5,760,910 | A | 6/1998 | Lepper, Jr. et al. |
| 5,890,929 | A | 4/1999 | Mills et al. |
| 5,919,134 | A | 7/1999 | Diab |
| 5,987,343 | A | 11/1999 | Kinast |
| 5,997,343 | A | 12/1999 | Mills et al. |
| 6,002,952 | A | 12/1999 | Diab et al. |
| 6,010,937 | A | 1/2000 | Karam et al. |
| 6,027,452 | A | 2/2000 | Flaherty et al. |
| 6,040,578 | A | 3/2000 | Malin et al. |
| 6,066,204 | A | 5/2000 | Haven |
| 6,115,673 | A | 9/2000 | Malin et al. |
| 6,124,597 | A | 9/2000 | Shehada et al. |

| | | | |
|---|---|---|---|
| 6,128,521 | A | 10/2000 | Marro et al. |
| 6,129,675 | A | 10/2000 | Jay |
| 6,144,868 | A | 11/2000 | Parker |
| 6,152,754 | A | 11/2000 | Gerhardt et al. |
| 6,184,521 | B1 | 2/2001 | Coffin, IV et al. |
| 6,232,609 | B1 | 5/2001 | Snyder et al. |
| 6,241,683 | B1 | 6/2001 | Macklem et al. |
| 6,253,097 | B1 | 6/2001 | Aronow et al. |
| 6,255,708 | B1 | 7/2001 | Sudharsanan et al. |
| 6,280,381 | B1 | 8/2001 | Malin et al. |
| 6,285,896 | B1 | 9/2001 | Tobler et al. |
| 6,308,089 | B1 | 10/2001 | von der Ruhr et al. |
| 6,317,627 | B1 | 11/2001 | Ennen et al. |
| 6,321,100 | B1 | 11/2001 | Parker |
| 6,334,065 | B1 | 12/2001 | Al-Ali et al. |
| 6,360,114 | B1 | 3/2002 | Diab et al. |
| 6,368,283 | B1 | 4/2002 | Xu et al. |
| 6,411,373 | B1 | 6/2002 | Garside et al. |
| 6,415,167 | B1 | 7/2002 | Blank et al. |
| 6,430,437 | B1 | 8/2002 | Marro |
| 6,430,525 | B1 | 8/2002 | Weber et al. |
| 6,463,311 | B1 | 10/2002 | Diab |
| 6,470,199 | B1 | 10/2002 | Kopotic et al. |
| 6,487,429 | B2 | 11/2002 | Hockersmith et al. |
| 6,505,059 | B1 | 1/2003 | Kollias et al. |
| 6,525,386 | B1 | 2/2003 | Mills et al. |
| 6,526,300 | B1 | 2/2003 | Kiani et al. |
| 6,534,012 | B1 | 3/2003 | Hazen et al. |
| 6,542,764 | B1 | 4/2003 | Al-Ali et al. |
| 6,580,086 | B1 | 6/2003 | Schulz et al. |
| 6,584,336 | B1 | 6/2003 | Ali et al. |
| 6,587,196 | B1 | 7/2003 | Stippick et al. |
| 6,587,199 | B1 | 7/2003 | Luu |
| 6,595,316 | B2 | 7/2003 | Cybulski et al. |
| 6,597,932 | B2 | 7/2003 | Tian et al. |
| 6,606,511 | B1 | 8/2003 | Ali et al. |
| 6,635,559 | B2 | 10/2003 | Greenwald et al. |
| 6,639,668 | B1 | 10/2003 | Trepagnier |
| 6,640,116 | B2 | 10/2003 | Diab |
| 6,640,117 | B2 | 10/2003 | Makarewicz et al. |
| 6,658,276 | B2 | 12/2003 | Kiani et al. |
| 6,661,161 | B1 | 12/2003 | Lanzo et al. |
| 6,697,656 | B1 | 2/2004 | Al-Ali |
| 6,697,658 | B2 | 2/2004 | Al-Ali |
| RE38,476 | E | 3/2004 | Diab et al. |
| RE38,492 | E | 4/2004 | Diab et al. |
| 6,738,652 | B2 | 5/2004 | Mattu et al. |
| 6,760,607 | B2 | 7/2004 | Al-Ali |
| 6,788,965 | B2 | 9/2004 | Ruchti et al. |
| 6,816,241 | B2 | 11/2004 | Grubisic |
| 6,822,564 | B2 | 11/2004 | Al-Ali |
| 6,850,787 | B2 | 2/2005 | Weber et al. |
| 6,850,788 | B2 | 2/2005 | Al-Ali |
| 6,876,931 | B2 | 4/2005 | Lorenz et al. |
| 6,920,345 | B2 | 7/2005 | Al-Ali et al. |
| 6,934,570 | B2 | 8/2005 | Kiani et al. |
| 6,943,348 | B1 | 9/2005 | Coffin, IV |
| 6,956,649 | B2 | 10/2005 | Acosta et al. |
| 6,961,598 | B2 | 11/2005 | Diab |
| 6,970,792 | B1 | 11/2005 | Diab |
| 6,985,764 | B2 | 1/2006 | Mason et al. |
| 6,990,364 | B2 | 1/2006 | Ruchti et al. |
| 6,998,247 | B2 | 2/2006 | Monfre et al. |
| 7,003,338 | B2 | 2/2006 | Weber et al. |
| 7,015,451 | B2 | 3/2006 | Dalke et al. |
| 7,027,849 | B2 | 4/2006 | Al-Ali |
| D526,719 | S | 8/2006 | Richie, Jr. et al. |
| 7,096,052 | B2 | 8/2006 | Mason et al. |
| 7,096,054 | B2 | 8/2006 | Abdul-Hafiz et al. |
| D529,616 | S | 10/2006 | Deros et al. |
| 7,133,710 | B2 | 11/2006 | Acosta et al. |
| 7,142,901 | B2 | 11/2006 | Kiani et al. |
| 7,225,006 | B2 | 5/2007 | Al-Ali et al. |
| RE39,672 | E | 6/2007 | Shehada et al. |
| 7,254,429 | B2 | 8/2007 | Schurman et al. |
| 7,254,431 | B2 | 8/2007 | Al-Ali et al. |
| 7,254,434 | B2 | 8/2007 | Schulz et al. |
| 7,274,955 | B2 | 9/2007 | Kiani et al. |
| D554,263 | S | 10/2007 | Al-Ali et al. |

(56) References Cited

U.S. PATENT DOCUMENTS

| | | | |
|---|---|---|---|
| 7,280,858 B2 | 10/2007 | Al-Ali et al. |
| 7,289,835 B2 | 10/2007 | Mansfield et al. |
| 7,292,883 B2 | 11/2007 | De Felice et al. |
| 7,341,559 B2 | 3/2008 | Schulz et al. |
| 7,343,186 B2 | 3/2008 | Lamego et al. |
| D566,282 S | 4/2008 | Al-Ali et al. |
| 7,356,365 B2 | 4/2008 | Schurman |
| 7,371,981 B2 | 5/2008 | Abdul-Hafiz |
| 7,373,193 B2 | 5/2008 | Al-Ali et al. |
| 7,377,794 B2 | 5/2008 | Al-Ali et al. |
| 7,395,158 B2 | 7/2008 | Monfre et al. |
| 7,415,297 B2 | 8/2008 | Al-Ali et al. |
| 7,438,683 B2 | 10/2008 | Al-Ali et al. |
| 7,483,729 B2 | 1/2009 | Al-Ali et al. |
| D587,657 S | 3/2009 | Al-Ali et al. |
| 7,500,950 B2 | 3/2009 | Al-Ali et al. |
| 7,509,494 B2 | 3/2009 | Al-Ali |
| 7,510,849 B2 | 3/2009 | Schurman et al. |
| 7,514,725 B2 | 4/2009 | Wojtczuk et al. |
| 7,519,406 B2 | 4/2009 | Blank et al. |
| D592,507 S | 5/2009 | Wachman et al. |
| 7,530,942 B1 | 5/2009 | Diab |
| 7,593,230 B2 | 9/2009 | Abul-Haj et al. |
| 7,596,398 B2 | 9/2009 | Al-Ali et al. |
| 7,606,608 B2 | 10/2009 | Blank et al. |
| 7,620,674 B2 | 11/2009 | Ruchti et al. |
| D606,659 S | 12/2009 | Kiani et al. |
| 7,629,039 B2 | 12/2009 | Eckerbom et al. |
| 7,640,140 B2 | 12/2009 | Ruchti et al. |
| 7,647,083 B2 | 1/2010 | Al-Ali et al. |
| D609,193 S | 2/2010 | Al-Ali et al. |
| D614,305 S | 4/2010 | Al-Ali et al. |
| 7,697,966 B2 | 4/2010 | Monfre et al. |
| 7,698,105 B2 | 4/2010 | Ruchti et al. |
| RE41,317 E | 5/2010 | Parker |
| RE41,333 E | 5/2010 | Blank et al. |
| 7,729,733 B2 | 6/2010 | Al-Ali et al. |
| 7,761,127 B2 | 7/2010 | Al-Ali et al. |
| 7,764,982 B2 | 7/2010 | Dalke et al. |
| D621,516 S | 8/2010 | Kiani et al. |
| 7,791,155 B2 | 9/2010 | Diab |
| RE41,912 E | 11/2010 | Parker |
| 7,880,626 B2 | 2/2011 | Al-Ali et al. |
| 7,909,772 B2 | 3/2011 | Popov et al. |
| 7,919,713 B2 | 4/2011 | Al-Ali et al. |
| 7,937,128 B2 | 5/2011 | Al-Ali |
| 7,937,129 B2 | 5/2011 | Mason et al. |
| 7,941,199 B2 | 5/2011 | Kiani |
| 7,957,780 B2 | 6/2011 | Lamego et al. |
| 7,962,188 B2 | 6/2011 | Kiani et al. |
| 7,976,472 B2 | 7/2011 | Kiani |
| 7,990,382 B2 | 8/2011 | Kiani |
| 8,008,088 B2 | 8/2011 | Bellott et al. |
| RE42,753 E | 9/2011 | Kiani-Azarbayjany et al. |
| 8,028,701 B2 | 10/2011 | Al-Ali et al. |
| 8,048,040 B2 | 11/2011 | Kiani |
| 8,050,728 B2 | 11/2011 | Al-Ali et al. |
| RE43,169 E | 2/2012 | Parker |
| 8,118,620 B2 | 2/2012 | Al-Ali et al. |
| 8,130,105 B2 | 3/2012 | Al-Ali et al. |
| 8,182,443 B1 | 5/2012 | Kiani |
| 8,190,223 B2 | 5/2012 | Al-Ali et al. |
| 8,203,438 B2 | 6/2012 | Kiani et al. |
| 8,203,704 B2 | 6/2012 | Merritt et al. |
| 8,219,172 B2 | 7/2012 | Schurman et al. |
| 8,224,411 B2 | 7/2012 | Al-Ali et al. |
| 8,229,532 B2 | 7/2012 | Davis |
| 8,233,955 B2 | 7/2012 | Al-Ali et al. |
| 8,255,026 B1 | 8/2012 | Al-Ali |
| 8,265,723 B1 | 9/2012 | McHale et al. |
| 8,274,360 B2 | 9/2012 | Sampath et al. |
| 8,280,473 B2 | 10/2012 | Al-Ali |
| 8,315,683 B2 | 11/2012 | Al-Ali et al. |
| RE43,860 E | 12/2012 | Parker |
| 8,346,330 B2 | 1/2013 | Lamego |
| 8,353,842 B2 | 1/2013 | Al-Ali et al. |
| 8,355,766 B2 | 1/2013 | MacNeish, III et al. |
| 8,374,665 B2 | 2/2013 | Lamego |
| 8,388,353 B2 | 3/2013 | Kiani et al. |
| 8,401,602 B2 | 3/2013 | Kiani |
| 8,414,499 B2 | 4/2013 | Al-Ali et al. |
| 8,418,524 B2 | 4/2013 | Al-Ali |
| 8,428,967 B2 | 4/2013 | Olsen et al. |
| 8,430,817 B1 | 4/2013 | Al-Ali et al. |
| 8,437,825 B2 | 5/2013 | Dalvi et al. |
| 8,455,290 B2 | 6/2013 | Siskavich |
| 8,457,707 B2 | 6/2013 | Kiani |
| 8,471,713 B2 | 6/2013 | Poeze et al. |
| 8,473,020 B2 | 6/2013 | Kiani et al. |
| 8,509,867 B2 | 8/2013 | Workman et al. |
| 8,515,509 B2 | 8/2013 | Bruinsma et al. |
| 8,523,781 B2 | 9/2013 | Al-Ali |
| D692,145 S | 10/2013 | Al-Ali et al. |
| 8,571,617 B2 | 10/2013 | Reichgott et al. |
| 8,571,618 B1 | 10/2013 | Lamego et al. |
| 8,571,619 B2 | 10/2013 | Al-Ali et al. |
| 8,577,431 B2 | 11/2013 | Lamego et al. |
| 8,584,345 B2 | 11/2013 | Al-Ali et al. |
| 8,588,880 B2 | 11/2013 | Abdul-Hafiz et al. |
| 8,630,691 B2 | 1/2014 | Lamego et al. |
| 8,641,631 B2 | 2/2014 | Sierra et al. |
| 8,652,060 B2 | 2/2014 | Al-Ali |
| 8,666,468 B1 | 3/2014 | Al-Ali |
| 8,670,811 B2 | 3/2014 | O'Reilly |
| RE44,823 E | 4/2014 | Parker |
| RE44,875 E | 4/2014 | Kiani et al. |
| 8,688,183 B2 | 4/2014 | Bruinsma et al. |
| 8,690,799 B2 | 4/2014 | Telfort et al. |
| 8,702,627 B2 | 4/2014 | Telfort et al. |
| 8,712,494 B1 | 4/2014 | MacNeish, III et al. |
| 8,715,206 B2 | 5/2014 | Telfort et al. |
| 8,723,677 B1 | 5/2014 | Kiani |
| 8,740,792 B1 | 6/2014 | Kiani et al. |
| 8,755,535 B2 | 6/2014 | Telfort et al. |
| 8,755,872 B1 | 6/2014 | Marinow |
| 8,764,671 B2 | 7/2014 | Kiani |
| 8,768,423 B2 | 7/2014 | Shakespeare et al. |
| 8,771,204 B2 | 7/2014 | Telfort et al. |
| 8,781,544 B2 | 7/2014 | Al-Ali et al. |
| 8,790,268 B2 | 7/2014 | Al-Ali |
| 8,801,613 B2 | 8/2014 | Al-Ali et al. |
| 8,821,397 B2 | 9/2014 | Al-Ali et al. |
| 8,821,415 B2 | 9/2014 | Al-Ali et al. |
| 8,830,449 B1 | 9/2014 | Lamego et al. |
| 8,840,549 B2 | 9/2014 | Al-Ali et al. |
| 8,852,094 B2 | 10/2014 | Al-Ali et al. |
| 8,852,994 B2 | 10/2014 | Wojtczuk et al. |
| 8,897,847 B2 | 11/2014 | Al-Ali |
| 8,911,377 B2 | 12/2014 | Al-Ali |
| 8,989,831 B2 | 3/2015 | Al-Ali et al. |
| 8,998,809 B2 | 4/2015 | Kiani |
| 9,066,666 B2 | 6/2015 | Kiani |
| 9,066,680 B1 | 6/2015 | Al-Ali et al. |
| 9,095,316 B2 | 8/2015 | Welch et al. |
| 9,106,038 B2 | 8/2015 | Telfort et al. |
| 9,107,625 B2 | 8/2015 | Telfort et al. |
| 9,131,881 B2 | 9/2015 | Diab et al. |
| 9,138,180 B1 | 9/2015 | Coverston et al. |
| 9,153,112 B1 | 10/2015 | Kiani et al. |
| 9,192,329 B2 | 11/2015 | Al-Ali |
| 9,192,351 B1 | 11/2015 | Telfort et al. |
| 9,195,385 B2 | 11/2015 | Al-Ali et al. |
| 9,211,095 B1 | 12/2015 | Al-Ali |
| 9,218,454 B2 | 12/2015 | Kiani et al. |
| 9,245,668 B1 | 1/2016 | Vo et al. |
| 9,267,572 B2 | 2/2016 | Barker et al. |
| 9,277,880 B2 | 3/2016 | Poeze et al. |
| 9,307,928 B1 | 4/2016 | Al-Ali et al. |
| 9,323,894 B2 | 4/2016 | Kiani |
| D755,392 S | 5/2016 | Hwang et al. |
| 9,326,712 B1 | 5/2016 | Kiani |
| 9,392,945 B2 | 7/2016 | Al-Ali et al. |
| 9,408,542 B1 | 8/2016 | Kinast et al. |
| 9,436,645 B2 | 9/2016 | Al-Ali et al. |

(56) References Cited

U.S. PATENT DOCUMENTS

| | | | |
|---|---|---|---|
| 9,445,759 B1 | 9/2016 | Lamego et al. | |
| 9,474,474 B2 | 10/2016 | Lamego et al. | |
| 9,480,435 B2 | 11/2016 | Olsen | |
| 9,510,779 B2 | 12/2016 | Poeze et al. | |
| 9,517,024 B2 | 12/2016 | Kiani et al. | |
| 9,532,722 B2 | 1/2017 | Lamego et al. | |
| 9,560,996 B2 | 2/2017 | Kiani | |
| 9,579,039 B2 | 2/2017 | Jansen et al. | |
| 9,582,646 B2 * | 2/2017 | Wang ................. | H04L 41/0672 |
| 9,622,692 B2 | 4/2017 | Lamego et al. | |
| D788,312 S | 5/2017 | Al-Ali et al. | |
| 9,641,240 B2 | 5/2017 | Dave et al. | |
| 9,649,054 B2 | 5/2017 | Lamego et al. | |
| 9,697,928 B2 | 7/2017 | Al-Ali et al. | |
| 9,717,458 B2 | 8/2017 | Lamego et al. | |
| 9,724,016 B1 | 8/2017 | Al-Ali et al. | |
| 9,724,024 B2 | 8/2017 | Al-Ali | |
| 9,724,025 B1 | 8/2017 | Kiani et al. | |
| 9,749,232 B2 | 8/2017 | Sampath et al. | |
| 9,750,442 B2 | 9/2017 | Olsen | |
| 9,750,461 B1 | 9/2017 | Telfort | |
| 9,775,545 B2 | 10/2017 | Al-Ali et al. | |
| 9,778,079 B1 | 10/2017 | Al-Ali et al. | |
| 9,782,077 B2 | 10/2017 | Lamego et al. | |
| 9,787,568 B2 | 10/2017 | Lamego et al. | |
| 9,808,188 B1 | 11/2017 | Perea et al. | |
| 9,839,379 B2 | 12/2017 | Al-Ali et al. | |
| 9,839,381 B1 | 12/2017 | Weber et al. | |
| 9,847,749 B2 | 12/2017 | Kiani et al. | |
| 9,848,800 B1 | 12/2017 | Lee et al. | |
| 9,861,298 B2 | 1/2018 | Eckerbom et al. | |
| 9,861,305 B1 | 1/2018 | Weber et al. | |
| 9,877,650 B2 | 1/2018 | Muhsin et al. | |
| 9,891,079 B2 | 2/2018 | Dalvi | |
| 9,913,079 B2 | 3/2018 | Srivatsa et al. | |
| 9,924,897 B1 | 3/2018 | Abdul-Hafiz | |
| 9,936,917 B2 | 4/2018 | Poeze et al. | |
| 9,955,937 B2 | 5/2018 | Telfort | |
| 9,965,946 B2 | 5/2018 | Al-Ali et al. | |
| D820,865 S | 6/2018 | Muhsin et al. | |
| 9,986,952 B2 | 6/2018 | Dalvi et al. | |
| D822,215 S | 7/2018 | Al-Ali et al. | |
| D822,216 S | 7/2018 | Barker et al. | |
| 10,010,276 B2 | 7/2018 | Al-Ali et al. | |
| 10,086,138 B1 | 10/2018 | Novak, Jr. | |
| 10,111,591 B2 | 10/2018 | Dyell et al. | |
| D833,624 S | 11/2018 | DeJong et al. | |
| 10,123,729 B2 | 11/2018 | Dyell et al. | |
| D835,282 S | 12/2018 | Barker et al. | |
| D835,283 S | 12/2018 | Barker et al. | |
| D835,284 S | 12/2018 | Barker et al. | |
| D835,285 S | 12/2018 | Barker et al. | |
| 10,149,616 B2 | 12/2018 | Al-Ali et al. | |
| 10,154,815 B2 | 12/2018 | Al-Ali et al. | |
| 10,159,412 B2 | 12/2018 | Lamego et al. | |
| 10,188,348 B2 | 1/2019 | Al-Ali et al. | |
| RE47,218 E | 2/2019 | Al-Ali | |
| RE47,244 E | 2/2019 | Kiani et al. | |
| RE47,249 E | 2/2019 | Kiani et al. | |
| 10,205,291 B2 | 2/2019 | Scruggs et al. | |
| 10,226,187 B2 | 3/2019 | Al-Ali et al. | |
| 10,231,657 B2 | 3/2019 | Al-Ali et al. | |
| 10,231,670 B2 | 3/2019 | Blank et al. | |
| RE47,353 E | 4/2019 | Kiani et al. | |
| 10,279,247 B2 | 5/2019 | Kiani | |
| 10,292,664 B2 | 5/2019 | Al-Ali | |
| 10,299,720 B2 | 5/2019 | Brown et al. | |
| 10,327,337 B2 | 6/2019 | Schmidt et al. | |
| 10,327,713 B2 | 6/2019 | Barker et al. | |
| 10,332,630 B2 | 6/2019 | Al-Ali | |
| 10,383,520 B2 | 8/2019 | Wojtczuk et al. | |
| 10,383,527 B2 | 8/2019 | Al-Ali | |
| 10,388,120 B2 | 8/2019 | Muhsin et al. | |
| D864,120 S | 10/2019 | Forrest et al. | |
| 10,441,181 B1 | 10/2019 | Telfort et al. | |
| 10,441,196 B2 | 10/2019 | Eckerbom et al. | |
| 10,448,844 B2 | 10/2019 | Al-Ali et al. | |
| 10,448,871 B2 | 10/2019 | Al-Ali et al. | |
| 10,456,038 B2 | 10/2019 | Lamego et al. | |
| 10,463,340 B2 | 11/2019 | Telfort et al. | |
| 10,471,159 B1 | 11/2019 | Lapotko et al. | |
| 10,505,311 B2 | 12/2019 | Al-Ali et al. | |
| 10,524,738 B2 | 1/2020 | Olsen | |
| 10,532,174 B2 | 1/2020 | Al-Ali | |
| 10,537,285 B2 | 1/2020 | Shreim et al. | |
| 10,542,903 B2 | 1/2020 | Al-Ali et al. | |
| 10,555,678 B2 | 2/2020 | Dalvi et al. | |
| 10,568,553 B2 | 2/2020 | O'Neil et al. | |
| 10,608,817 B2 | 3/2020 | Haider et al. | |
| D880,477 S | 4/2020 | Forrest et al. | |
| 10,617,302 B2 | 4/2020 | Al-Ali et al. | |
| 10,617,335 B2 | 4/2020 | Al-Ali et al. | |
| 10,637,181 B2 | 4/2020 | Al-Ali et al. | |
| D886,849 S | 6/2020 | Muhsin et al. | |
| D887,548 S | 6/2020 | Abdul-Hafiz et al. | |
| D887,549 S | 6/2020 | Abdul-Hafiz et al. | |
| 10,667,764 B2 | 6/2020 | Ahmed et al. | |
| D890,708 S | 7/2020 | Forrest et al. | |
| 10,721,785 B2 | 7/2020 | Al-Ali | |
| 10,736,518 B2 | 8/2020 | Al-Ali et al. | |
| 10,750,984 B2 | 8/2020 | Pauley et al. | |
| D897,098 S | 9/2020 | Al-Ali | |
| 10,779,098 B2 | 9/2020 | Iswanto et al. | |
| 10,827,961 B1 | 11/2020 | Iyengar et al. | |
| 10,828,007 B1 | 11/2020 | Telfort et al. | |
| 10,832,818 B2 | 11/2020 | Muhsin et al. | |
| 10,849,554 B2 | 12/2020 | Shreim et al. | |
| 10,856,750 B2 | 12/2020 | Indorf | |
| D906,970 S | 1/2021 | Forrest et al. | |
| D908,213 S | 1/2021 | Abdul-Hafiz et al. | |
| 10,918,281 B2 | 2/2021 | Al-Ali et al. | |
| 10,932,705 B2 | 3/2021 | Muhsin et al. | |
| 10,932,729 B2 | 3/2021 | Kiani et al. | |
| 10,939,878 B2 | 3/2021 | Kiani et al. | |
| 10,956,950 B2 | 3/2021 | Al-Ali et al. | |
| D916,135 S | 4/2021 | Indorf et al. | |
| D917,046 S | 4/2021 | Abdul-Hafiz et al. | |
| D917,550 S | 4/2021 | Indorf et al. | |
| D917,564 S | 4/2021 | Indorf et al. | |
| D917,704 S | 4/2021 | Al-Ali et al. | |
| 10,987,066 B2 | 4/2021 | Chandran et al. | |
| 10,991,135 B2 | 4/2021 | Al-Ali et al. | |
| D919,094 S | 5/2021 | Al-Ali et al. | |
| D919,100 S | 5/2021 | Al-Ali et al. | |
| 11,006,867 B2 | 5/2021 | Al-Ali | |
| D921,202 S | 6/2021 | Al-Ali et al. | |
| 11,024,064 B2 | 6/2021 | Muhsin et al. | |
| 11,026,604 B2 | 6/2021 | Chen et al. | |
| D925,597 S | 7/2021 | Chandran et al. | |
| D927,699 S | 8/2021 | Al-Ali et al. | |
| 11,076,777 B2 | 8/2021 | Lee et al. | |
| 11,114,188 B2 | 9/2021 | Poeze et al. | |
| D933,232 S | 10/2021 | Al-Ali et al. | |
| D933,233 S | 10/2021 | Al-Ali et al. | |
| D933,234 S | 10/2021 | Al-Ali et al. | |
| 11,145,408 B2 | 10/2021 | Sampath et al. | |
| 11,147,518 B1 | 10/2021 | Al-Ali et al. | |
| 11,185,262 B2 | 11/2021 | Al-Ali et al. | |
| 11,191,484 B2 | 12/2021 | Kiani et al. | |
| D946,596 S | 3/2022 | Ahmed | |
| D946,597 S | 3/2022 | Ahmed | |
| D946,598 S | 3/2022 | Ahmed | |
| D946,617 S | 3/2022 | Ahmed | |
| 11,272,839 B2 | 3/2022 | Al-Ali et al. | |
| 11,289,199 B2 | 3/2022 | Al-Ali | |
| RE49,034 E | 4/2022 | Al-Ali | |
| 11,298,021 B2 | 4/2022 | Muhsin et al. | |
| D950,580 S | 5/2022 | Ahmed | |
| D950,599 S | 5/2022 | Ahmed | |
| D950,738 S | 5/2022 | Al-Ali et al. | |
| D957,648 S | 7/2022 | Al-Ali | |
| 11,382,567 B2 | 7/2022 | O'Brien et al. | |
| 11,389,093 B2 | 7/2022 | Triman et al. | |
| 11,406,286 B2 | 8/2022 | Al-Ali et al. | |

(56) References Cited

U.S. PATENT DOCUMENTS

| | | | |
|---|---|---|---|
| 11,417,426 | B2 | 8/2022 | Muhsin et al. |
| 11,439,329 | B2 | 9/2022 | Lamego |
| 11,445,948 | B2 | 9/2022 | Scruggs et al. |
| D965,789 | S | 10/2022 | Al-Ali et al. |
| D967,433 | S | 10/2022 | Al-Ali et al. |
| 11,464,410 | B2 | 10/2022 | Muhsin |
| 11,504,058 | B1 | 11/2022 | Sharma et al. |
| 11,504,066 | B1 | 11/2022 | Dalvi et al. |
| D971,933 | S | 12/2022 | Ahmed |
| D973,072 | S | 12/2022 | Ahmed |
| D973,685 | S | 12/2022 | Ahmed |
| D973,686 | S | 12/2022 | Ahmed |
| D974,193 | S | 1/2023 | Forrest et al. |
| D979,516 | S | 2/2023 | Al-Ali et al. |
| D980,091 | S | 3/2023 | Forrest et al. |
| 11,596,363 | B2 | 3/2023 | Lamego |
| 11,627,919 | B2 | 4/2023 | Kiani et al. |
| 11,637,437 | B2 | 4/2023 | Al-Ali et al. |
| D985,498 | S | 5/2023 | Al-Ali et al. |
| 11,653,862 | B2 | 5/2023 | Dalvi et al. |
| D989,112 | S | 6/2023 | Muhsin et al. |
| D989,327 | S | 6/2023 | Al-Ali et al. |
| 11,678,829 | B2 | 6/2023 | Al-Ali et al. |
| 11,679,579 | B2 | 6/2023 | Al-Ali |
| 11,684,296 | B2 | 6/2023 | Vo et al. |
| 11,692,934 | B2 | 7/2023 | Normand et al. |
| 11,701,043 | B2 | 7/2023 | Al-Ali et al. |
| D997,365 | S | 8/2023 | Hwang |
| 11,721,105 | B2 | 8/2023 | Ranasinghe et al. |
| 11,730,379 | B2 | 8/2023 | Ahmed et al. |
| D998,625 | S | 9/2023 | Indorf et al. |
| D998,630 | S | 9/2023 | Indorf et al. |
| D998,631 | S | 9/2023 | Indorf et al. |
| D999,244 | S | 9/2023 | Indorf et al. |
| D999,245 | S | 9/2023 | Indorf et al. |
| D999,246 | S | 9/2023 | Indorf et al. |
| 11,766,198 | B2 | 9/2023 | Pauley et al. |
| D1,000,975 | S | 10/2023 | Al-Ali et al. |
| 11,803,623 | B2 | 10/2023 | Kiani et al. |
| 11,832,940 | B2 | 12/2023 | Diab et al. |
| D1,013,179 | S | 1/2024 | Al-Ali et al. |
| 11,872,156 | B2 | 1/2024 | Telfort et al. |
| 11,879,960 | B2 | 1/2024 | Ranasinghe et al. |
| 11,883,129 | B2 | 1/2024 | Olsen |
| D1,022,729 | S | 4/2024 | Forrest et al. |
| 11,951,186 | B2 | 4/2024 | Krishnamani et al. |
| 11,974,833 | B2 | 5/2024 | Forrest et al. |
| 11,986,067 | B2 | 5/2024 | Al-Ali et al. |
| 11,986,289 | B2 | 5/2024 | Dalvi et al. |
| 11,986,305 | B2 | 5/2024 | Al-Ali et al. |
| D1,031,729 | S | 6/2024 | Forrest et al. |
| 12,004,869 | B2 | 6/2024 | Kiani et al. |
| 12,014,328 | B2 | 6/2024 | Wachman et al. |
| D1,036,293 | S | 7/2024 | Al-Ali et al. |
| D1,037,462 | S | 7/2024 | Al-Ali et al. |
| 12,029,844 | B2 | 7/2024 | Pauley et al. |
| 12,048,534 | B2 | 7/2024 | Vo et al. |
| 12,064,217 | B2 | 8/2024 | Ahmed et al. |
| 12,066,426 | B1 | 8/2024 | Lapotko et al. |
| D1,041,511 | S | 9/2024 | Indorf et al. |
| D1,042,596 | S | 9/2024 | DeJong et al. |
| D1,042,852 | S | 9/2024 | Hwang |
| 12,076,159 | B2 | 9/2024 | Belur Nagaraj et al. |
| 12,082,926 | B2 | 9/2024 | Sharma et al. |
| D1,044,828 | S | 10/2024 | Chandran et al. |
| D1,048,571 | S | 10/2024 | Yu et al. |
| D1,048,908 | S | 10/2024 | Al-Ali et al. |
| 12,106,752 | B2 | 10/2024 | Campbell et al. |
| 12,114,974 | B2 | 10/2024 | Al-Ali et al. |
| 12,126,683 | B2 | 10/2024 | Koo et al. |
| 12,127,838 | B2 | 10/2024 | Olsen et al. |
| 12,128,213 | B2 | 10/2024 | Kiani et al. |
| 12,131,661 | B2 | 10/2024 | Pauley et al. |
| D1,050,910 | S | 11/2024 | Al-Ali et al. |
| 12,178,572 | B1 | 12/2024 | Pauley et al. |
| 12,178,581 | B2 | 12/2024 | Telfort et al. |
| 12,178,852 | B2 | 12/2024 | Kiani et al. |
| D1,057,159 | S | 1/2025 | DeJong et al. |
| D1,057,160 | S | 1/2025 | DeJong et al. |
| 12,198,790 | B1 | 1/2025 | Al-Ali |
| 12,200,421 | B2 | 1/2025 | Campbell et al. |
| 12,207,901 | B1 | 1/2025 | Lapotko et al. |
| D1,060,680 | S | 2/2025 | Al-Ali et al. |
| D1,061,585 | S | 2/2025 | Indorf |
| D1,063,893 | S | 2/2025 | DeJong et al. |
| 12,220,207 | B2 | 2/2025 | Telfort et al. |
| 12,235,941 | B2 | 2/2025 | Kiani et al. |
| 12,236,767 | B2 | 2/2025 | Muhsin |
| D1,066,244 | S | 3/2025 | Lim et al. |
| D1,066,672 | S | 3/2025 | Al-Ali et al. |
| D1,068,656 | S | 4/2025 | Trevisan et al. |
| D1,071,195 | S | 4/2025 | Seung |
| D1,072,836 | S | 4/2025 | Indorf |
| D1,072,837 | S | 4/2025 | Ahmed et al. |
| 12,272,445 | B1 | 4/2025 | Kiani |
| D1,078,689 | S | 6/2025 | Hwang |
| D1,079,020 | S | 6/2025 | Hwang |
| 12,336,796 | B2 | 6/2025 | Al-Ali |
| D1,083,653 | S | 7/2025 | DeJong et al. |
| D1,085,102 | S | 7/2025 | Indorf et al. |
| 12,362,596 | B2 | 7/2025 | Barker et al. |
| 12,390,114 | B2 | 8/2025 | Novak, Jr. et al. |
| D1,092,244 | S | 9/2025 | DeJong et al. |
| D1,093,406 | S | 9/2025 | Indorf et al. |
| D1,094,735 | S | 9/2025 | DeJong et al. |
| D1,095,288 | S | 9/2025 | Lim |
| D1,095,483 | S | 9/2025 | DeJong et al. |
| 12,433,524 | B2 | 10/2025 | Al-Ali et al. |
| 12,440,128 | B2 | 10/2025 | Al-Ali et al. |
| D1,102,622 | S | 11/2025 | Al-Ali et al. |
| 12,478,272 | B2 | 11/2025 | Telfort et al. |
| 12,478,293 | B1 | 11/2025 | Al-Ali et al. |
| D1,106,466 | S | 12/2025 | Avendaño et al. |
| 12,495,967 | B2 | 12/2025 | Muhsin et al. |
| 12,495,999 | B2 | 12/2025 | Al-Ali et al. |
| 12,507,952 | B2 | 12/2025 | Al-Ali et al. |
| 12,521,021 | B2 | 1/2026 | Al-Ali et al. |
| 12,521,506 | B2 | 1/2026 | Yu et al. |
| 12,538,084 | B1 | 1/2026 | Telfort et al. |
| 12,539,046 | B2 | 2/2026 | Kiani |
| 12,575,797 | B2 | 3/2026 | Olsen et al. |
| 2001/0034477 | A1 | 10/2001 | Mansfield et al. |
| 2001/0039483 | A1 | 11/2001 | Brand et al. |
| 2002/0010401 | A1 | 1/2002 | Bushmakin et al. |
| 2002/0045836 | A1 | 4/2002 | Alkawwas |
| 2002/0058864 | A1 | 5/2002 | Mansfield et al. |
| 2002/0133080 | A1 | 9/2002 | Apruzzese et al. |
| 2003/0013975 | A1 | 1/2003 | Kiani |
| 2003/0018243 | A1 | 1/2003 | Gerhardt et al. |
| 2003/0144582 | A1 | 7/2003 | Cohen et al. |
| 2003/0156288 | A1 | 8/2003 | Barnum et al. |
| 2003/0212312 | A1 | 11/2003 | Coffin, IV et al. |
| 2004/0106163 | A1 | 6/2004 | Workman, Jr. et al. |
| 2005/0055276 | A1 | 3/2005 | Kiani et al. |
| 2005/0102167 | A1 | 5/2005 | Kapoor |
| 2005/0234317 | A1 | 10/2005 | Kiani |
| 2006/0073719 | A1 | 4/2006 | Kiani |
| 2006/0189871 | A1 | 8/2006 | Al-Ali et al. |
| 2007/0073116 | A1 | 3/2007 | Kiani et al. |
| 2007/0180140 | A1 | 8/2007 | Welch et al. |
| 2007/0244377 | A1 | 10/2007 | Cozad et al. |
| 2008/0064965 | A1 | 3/2008 | Jay et al. |
| 2008/0094228 | A1 | 4/2008 | Welch et al. |
| 2008/0103375 | A1 | 5/2008 | Kiani |
| 2008/0221418 | A1 | 9/2008 | Al-Ali et al. |
| 2009/0036759 | A1 | 2/2009 | Ault et al. |
| 2009/0093687 | A1 | 4/2009 | Telfort et al. |
| 2009/0095926 | A1 | 4/2009 | MacNeish, III |
| 2009/0247984 | A1 | 10/2009 | Lamego et al. |
| 2009/0275844 | A1 | 11/2009 | Al-Ali |
| 2010/0004518 | A1 | 1/2010 | Vo et al. |
| 2010/0030040 | A1 | 2/2010 | Poeze et al. |
| 2010/0099964 | A1 | 4/2010 | O'Reilly et al. |
| 2010/0198613 | A1 | 8/2010 | Weller |

(56) References Cited

U.S. PATENT DOCUMENTS

| | | |
|---|---|---|
| 2010/0234718 A1 | 9/2010 | Sampath et al. |
| 2010/0270257 A1 | 10/2010 | Wachman et al. |
| 2011/0028806 A1 | 2/2011 | Merritt et al. |
| 2011/0028809 A1 | 2/2011 | Goodman |
| 2011/0040197 A1 | 2/2011 | Welch et al. |
| 2011/0082711 A1 | 4/2011 | Poeze et al. |
| 2011/0087081 A1 | 4/2011 | Kiani et al. |
| 2011/0118561 A1 | 5/2011 | Tari et al. |
| 2011/0137297 A1 | 6/2011 | Kiani et al. |
| 2011/0172498 A1 | 7/2011 | Olsen et al. |
| 2012/0123231 A1 | 5/2012 | O'Reilly |
| 2012/0165629 A1 | 6/2012 | Merritt et al. |
| 2012/0209084 A1 | 8/2012 | Olsen et al. |
| 2012/0226117 A1 | 9/2012 | Lamego et al. |
| 2012/0283524 A1 | 11/2012 | Kiani et al. |
| 2013/0023775 A1 | 1/2013 | Lamego et al. |
| 2013/0060147 A1 | 3/2013 | Welch et al. |
| 2013/0096405 A1 | 4/2013 | Garfio |
| 2013/0296672 A1 | 11/2013 | O'Neil et al. |
| 2013/0331036 A1* | 12/2013 | Baker ..................... H04Q 9/00 |
| | | 455/41.3 |
| 2013/0345921 A1 | 12/2013 | Al-Ali et al. |
| 2014/0166076 A1 | 6/2014 | Kiani et al. |
| 2014/0180160 A1 | 6/2014 | Brown et al. |
| 2014/0187973 A1 | 7/2014 | Brown et al. |
| 2014/0275871 A1 | 9/2014 | Lamego et al. |
| 2014/0275872 A1 | 9/2014 | Merritt et al. |
| 2014/0316217 A1 | 10/2014 | Purdon et al. |
| 2014/0316218 A1 | 10/2014 | Purdon et al. |
| 2014/0323897 A1 | 10/2014 | Brown et al. |
| 2014/0323898 A1 | 10/2014 | Purdon et al. |
| 2015/0005600 A1 | 1/2015 | Blank et al. |
| 2015/0011907 A1 | 1/2015 | Purdon et al. |
| 2015/0073241 A1 | 3/2015 | Lamego |
| 2015/0080754 A1 | 3/2015 | Purdon et al. |
| 2015/0099950 A1 | 4/2015 | Al-Ali et al. |
| 2017/0024748 A1 | 1/2017 | Haider |
| 2017/0155427 A1 | 6/2017 | Hasan et al. |
| 2017/0173632 A1 | 6/2017 | Al-Ali |
| 2017/0251974 A1 | 9/2017 | Shreim et al. |
| 2018/0242926 A1 | 8/2018 | Muhsin et al. |
| 2018/0247353 A1* | 8/2018 | Al-Ali .................. A61B 5/0205 |
| 2018/0247712 A1 | 8/2018 | Muhsin et al. |
| 2019/0117070 A1* | 4/2019 | Muhsin ................ A61B 5/7465 |
| 2019/0125459 A1 | 5/2019 | Shelton, IV |
| 2019/0239787 A1 | 8/2019 | Pauley et al. |
| 2019/0320906 A1 | 10/2019 | Olsen |
| 2019/0371478 A1* | 12/2019 | Rondoni ................ G16H 10/20 |
| 2019/0373471 A1 | 12/2019 | Li |
| 2020/0060869 A1 | 2/2020 | Telfort et al. |
| 2020/0111552 A1 | 4/2020 | Ahmed |
| 2020/0113520 A1 | 4/2020 | Abdul-Hafiz et al. |
| 2020/0138368 A1 | 5/2020 | Kiani et al. |
| 2020/0163597 A1 | 5/2020 | Dalvi et al. |
| 2020/0253474 A1 | 8/2020 | Muhsin et al. |
| 2020/0253544 A1 | 8/2020 | Belur Nagaraj et al. |
| 2020/0275841 A1 | 9/2020 | Telfort et al. |
| 2020/0288983 A1 | 9/2020 | Telfort et al. |
| 2020/0329983 A1 | 10/2020 | Al-Ali et al. |
| 2020/0329993 A1 | 10/2020 | Al-Ali et al. |
| 2021/0000347 A1 | 1/2021 | Stump |
| 2021/0022628 A1 | 1/2021 | Telfort et al. |
| 2021/0104173 A1 | 4/2021 | Pauley et al. |
| 2021/0113121 A1 | 4/2021 | Diab et al. |
| 2021/0117525 A1 | 4/2021 | Kiani et al. |
| 2021/0118581 A1 | 4/2021 | Kiani et al. |
| 2021/0121582 A1 | 4/2021 | Krishnamani et al. |
| 2021/0161465 A1 | 6/2021 | Barker et al. |
| 2021/0236729 A1 | 8/2021 | Kiani et al. |
| 2021/0256835 A1 | 8/2021 | Ranasinghe et al. |
| 2021/0275101 A1 | 9/2021 | Vo et al. |
| 2021/0290060 A1 | 9/2021 | Ahmed |
| 2021/0290072 A1 | 9/2021 | Forrest |
| 2021/0290080 A1 | 9/2021 | Ahmed |
| 2021/0290120 A1 | 9/2021 | Al-Ali |
| 2021/0290177 A1 | 9/2021 | Novak, Jr. |
| 2021/0290184 A1 | 9/2021 | Ahmed |
| 2021/0296008 A1 | 9/2021 | Novak, Jr. |
| 2021/0330228 A1 | 10/2021 | Olsen et al. |
| 2021/0386382 A1 | 12/2021 | Olsen et al. |
| 2021/0402110 A1 | 12/2021 | Pauley et al. |
| 2022/0039707 A1 | 2/2022 | Sharma et al. |
| 2022/0053892 A1 | 2/2022 | Al-Ali et al. |
| 2022/0071562 A1 | 3/2022 | Kiani |
| 2022/0096603 A1 | 3/2022 | Kiani et al. |
| 2022/0151521 A1 | 5/2022 | Krishnamani et al. |
| 2022/0218244 A1 | 7/2022 | Kiani et al. |
| 2022/0287574 A1 | 9/2022 | Telfort et al. |
| 2022/0296161 A1 | 9/2022 | Al-Ali et al. |
| 2022/0361819 A1 | 11/2022 | Al-Ali et al. |
| 2022/0379059 A1 | 12/2022 | Yu et al. |
| 2022/0392610 A1 | 12/2022 | Kiani et al. |
| 2023/0028745 A1 | 1/2023 | Al-Ali |
| 2023/0038389 A1 | 2/2023 | Vo |
| 2023/0045647 A1 | 2/2023 | Vo |
| 2023/0058052 A1 | 2/2023 | Al-Ali |
| 2023/0058342 A1 | 2/2023 | Kiani |
| 2023/0069789 A1 | 3/2023 | Koo et al. |
| 2023/0087671 A1 | 3/2023 | Telfort et al. |
| 2023/0110152 A1 | 4/2023 | Forrest et al. |
| 2023/0111198 A1 | 4/2023 | Yu et al. |
| 2023/0115397 A1 | 4/2023 | Vo et al. |
| 2023/0116371 A1 | 4/2023 | Mills et al. |
| 2023/0135297 A1 | 5/2023 | Kiani et al. |
| 2023/0138098 A1 | 5/2023 | Telfort et al. |
| 2023/0145155 A1 | 5/2023 | Krishnamani et al. |
| 2023/0147750 A1 | 5/2023 | Barker et al. |
| 2023/0210417 A1 | 7/2023 | Al-Ali et al. |
| 2023/0222805 A1 | 7/2023 | Muhsin et al. |
| 2023/0222887 A1 | 7/2023 | Muhsin et al. |
| 2023/0226331 A1 | 7/2023 | Kiani et al. |
| 2023/0284916 A1 | 9/2023 | Telfort |
| 2023/0284943 A1 | 9/2023 | Scruggs et al. |
| 2023/0301562 A1 | 9/2023 | Scruggs et al. |
| 2023/0317269 A1* | 10/2023 | Davis .................... G06N 5/022 |
| | | 705/2 |
| 2023/0346993 A1 | 11/2023 | Kiani et al. |
| 2023/0368221 A1 | 11/2023 | Haider |
| 2023/0371893 A1 | 11/2023 | Al-Ali et al. |
| 2023/0389837 A1 | 12/2023 | Krishnamani et al. |
| 2024/0016418 A1 | 1/2024 | Devadoss et al. |
| 2024/0016419 A1 | 1/2024 | Devadoss et al. |
| 2024/0049310 A1 | 2/2024 | Al-Ali et al. |
| 2024/0049986 A1 | 2/2024 | Al-Ali et al. |
| 2024/0081656 A1 | 3/2024 | DeJong et al. |
| 2024/0122486 A1 | 4/2024 | Kiani |
| 2024/0180456 A1 | 6/2024 | Al-Ali |
| 2024/0188872 A1 | 6/2024 | Al-Ali et al. |
| 2024/0194353 A1 | 6/2024 | Al-Ali et al. |
| 2024/0245855 A1 | 7/2024 | Vo et al. |
| 2024/0260894 A1 | 8/2024 | Olsen |
| 2024/0267698 A1 | 8/2024 | Telfort et al. |
| 2024/0277233 A1 | 8/2024 | Al-Ali |
| 2024/0277280 A1 | 8/2024 | Al-Ali et al. |
| 2024/0298920 A1 | 9/2024 | Fernkbist et al. |
| 2024/0306985 A1 | 9/2024 | Vo et al. |
| 2024/0324953 A1 | 10/2024 | Telfort |
| 2024/0380246 A1 | 11/2024 | Moran |
| 2024/0380247 A1 | 11/2024 | Moran |
| 2024/0404549 A1 | 12/2024 | Campbell et al. |
| 2025/0000458 A1 | 1/2025 | Abdul-Hafiz et al. |
| 2025/0037836 A1 | 1/2025 | Kiani |
| 2025/0100482 A1 | 3/2025 | Al-Ali et al. |
| 2025/0118415 A1 | 4/2025 | Olsen |
| 2025/0255764 A1 | 8/2025 | Stead |
| 2025/0278512 A1 | 9/2025 | Koo et al. |
| 2025/0281059 A1 | 9/2025 | Avendano |
| 2025/0288250 A1 | 9/2025 | Al-Ali et al. |
| 2025/0295366 A1 | 9/2025 | Al-Ali et al. |
| 2025/0302426 A1 | 10/2025 | Ha et al. |
| 2025/0311949 A1 | 10/2025 | Al-Ali et al. |
| 2025/0318761 A1 | 10/2025 | Al-Ali et al. |
| 2025/0322950 A1 | 10/2025 | Al-Ali et al. |
| 2025/0323417 A1 | 10/2025 | Rey |

(56)　　　　　References Cited

U.S. PATENT DOCUMENTS

| | | |
|---|---|---|
| 2025/0329240 A1 | 10/2025 | Kiani |
| 2025/0344010 A1 | 11/2025 | Al-Ali et al. |
| 2026/0014333 A1 | 1/2026 | Fernkvist et al. |
| 2026/0014334 A1 | 1/2026 | Danwihl |
| 2026/0048198 A1 | 2/2026 | Vo et al. |

OTHER PUBLICATIONS

International Search Report and Written Opinion received in PCT Application No. PCT/US2023/071613 dated Nov. 24, 2023 in 17 pages.

* cited by examiner

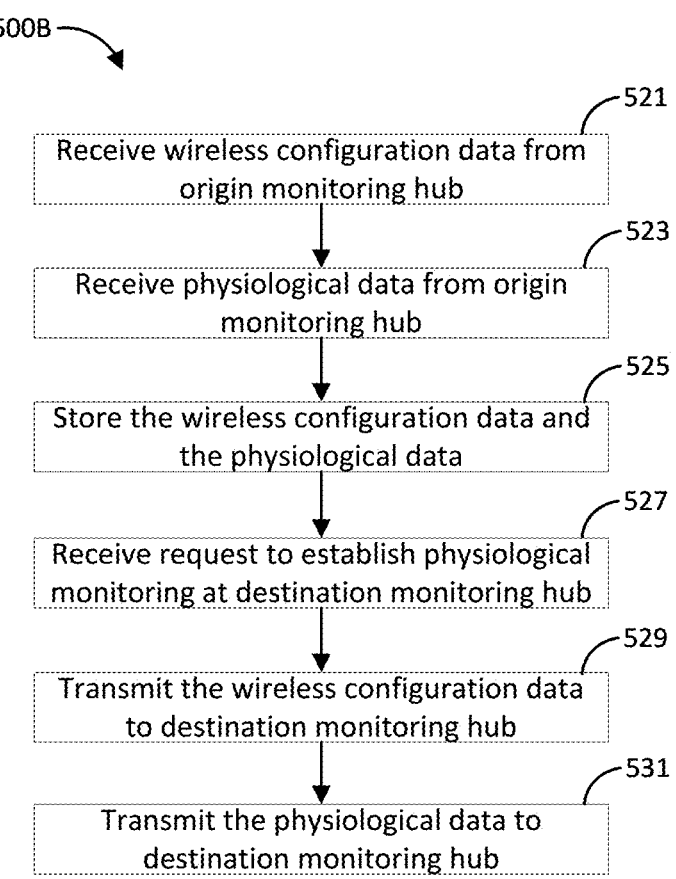

500B

Receive wireless configuration data from
origin monitoring hub — 521

Receive physiological data from origin
monitoring hub — 523

Store the wireless configuration data and
the physiological data — 525

Receive request to establish physiological
monitoring at destination monitoring hub — 527

Transmit the wireless configuration data
to destination monitoring hub — 529

Transmit the physiological data to
destination monitoring hub — 531

561
Establish wireless communication with sensor(s)

563
Transmit wireless configuration data associated with sensor(s) to a remote computing device 565
Receive physiological data originating from sensor(s) via wireless communication 567
Transmit physiological data to remote computing device

703

700

700

700

700

705        707    709

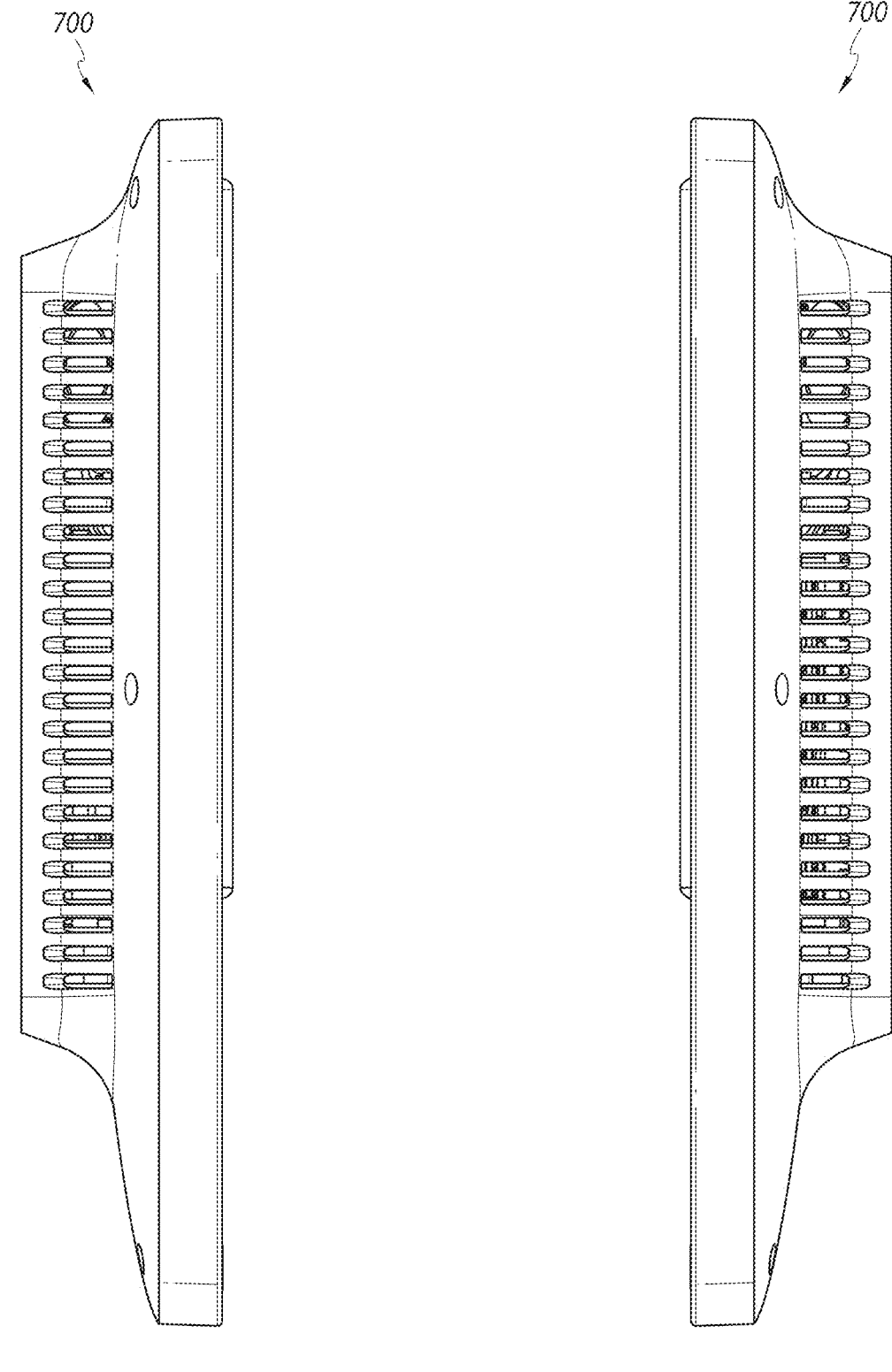
*FIG. 7J*             *FIG. 7K*

700

910

700

910

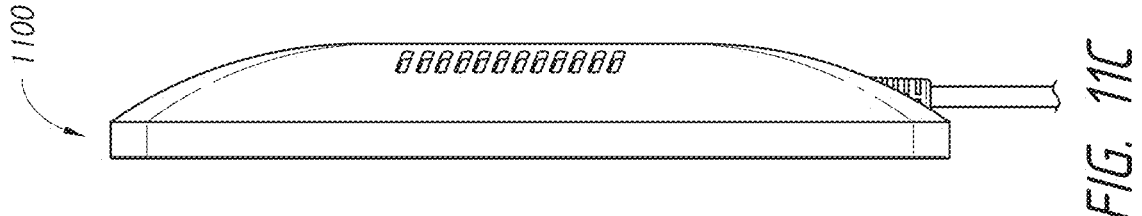
_FIG. 11C_
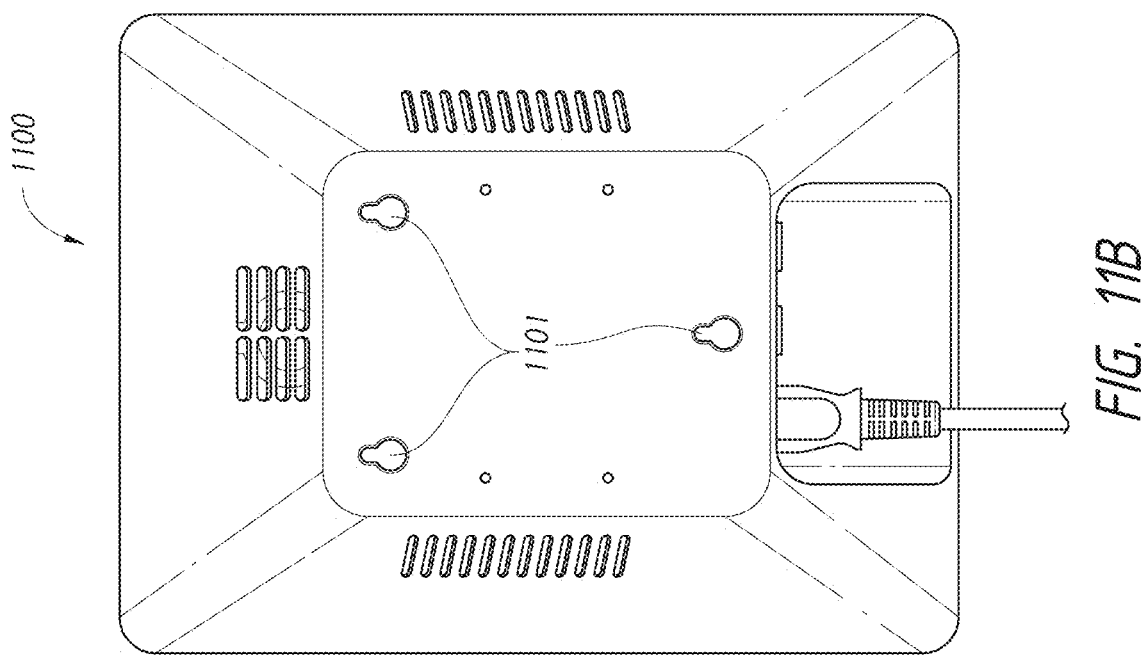
_FIG. 11B_
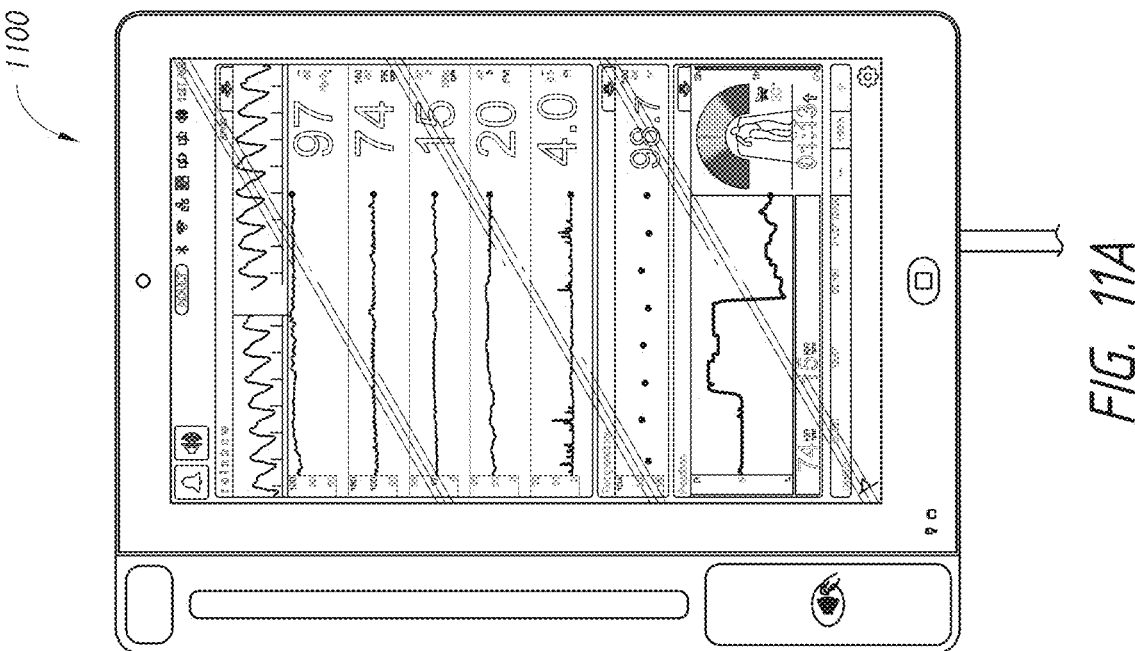
_FIG. 11A_

TRANSFERRING WIRELESS MONITORING WITH REDUCED DATA LOSS

CROSS REFERENCE TO RELATED APPLICATIONS

Any and all applications for which a foreign or domestic priority claim is identified in the Application Data Sheet as filed with the present application are hereby incorporated by reference under 37 CFR 1.57. This application claims benefit of priority to U.S. Provisional Application No. 63/370, 637, filed Aug. 5, 2022. The disclosures of each of the aforementioned applications are incorporated herein in their entireties for all purposes.

FIELD OF THE DISCLOSURE

The present disclosure relates to physiological monitoring devices, systems, and methods.

BACKGROUND

Hospitals, nursing homes, and other patient care facilities typically utilize a number of sensors, devices, and/or monitors to collect or analyze a patient's physiological parameters. Various conventional sensor systems exist which collect physiological data using physiological sensors, process the data, and display the data on a display device. Clinicians, including doctors, nurses, and other medical personnel, use the physiological parameters obtained from patient monitors to diagnose illnesses and to prescribe treatments. Clinicians also use the physiological parameters to monitor patients during various clinical situations to determine whether to increase the level of medical care given to patients.

SUMMARY

Some conventional sensor systems require time-consuming and complex procedures for changing the monitoring of physiological data between display devices. For example, a user may be required to unplug sensors from a first display device and replug the sensors into a second display device. As another example, a user may be required to power the sensors off and then power them on to wirelessly connect with a different display device. As another example, a user may be required to manually change a pairing status of the sensors and/or display devices to terminate a wireless connection with one display device and/or to establish a wireless connection with another display device. For at least the foregoing examples, changing monitoring of physiological data from a first display device to a second display device in a conventional sensor system can take long amounts of time, can be overly complex and frustrating to a user, can result in user error, and can result in loss of physiological data such as during a time in which the sensors are not connected (e.g., wirelessly and/or wired) to any display device.

Various implementations of systems, methods and devices within the scope of the appended claims each have several aspects, no single one of which is solely responsible for the desirable attributes described herein. Without limiting the scope of the appended claims, the description below describes some prominent features.

Details of one or more implementations of the subject matter described in this specification are set forth in the accompanying drawings and the description below. Other features, aspects, and advantages will become apparent from the description, the drawings, and the claims. Note that relative dimensions of the following figures may not be drawn to scale.

Disclosed herein is a monitoring hub configured to monitor a health status of a subject having a wireless wearable device. The monitoring hub can comprise one or more hardware computer processors. The one or more hardware processors can be configured to execute a plurality of computer executable instructions to cause the monitoring hub to responsive to a request to establish wireless monitoring of a subject's physiology at the monitoring hub: access wireless configuration data governing wireless communication with a wearable device on a subject, said wireless configuration data comprising at least one or more device addresses associated with the wearable device, said wireless configuration data received at the monitoring hub from a remote server. The one or more hardware processors can be configured to execute a plurality of computer executable instructions to cause the monitoring hub to responsive to a request to establish wireless monitoring of a subject's physiology at the monitoring hub based on at least the wireless configuration data, establish wireless communication between the monitoring hub and the wearable device to cause the monitoring hub to wirelessly receive real-time physiological data from the wearable device using one or more wireless communication protocols. The one or more hardware processors can be configured to execute a plurality of computer executable instructions to cause the monitoring hub to responsive to a request to establish wireless monitoring of a subject's physiology at the monitoring hub receive historical physiological data from the remote server, the historical physiological data comprising physiological data collected by the wearable device before establishing the wireless communication between the monitoring hub and the wearable device, the historical physiological data comprising physiological data communicated from the wearable device to another monitoring hub before establishing the wireless communication between the monitoring hub and the wearable device. The one or more hardware processors can be configured to execute a plurality of computer executable instructions to cause the monitoring hub to responsive to a request to establish wireless monitoring of a subject's physiology at the monitoring hub generate user interface data for rendering a user interface including the real-time physiological data in combination with the historical physiological data to reduce a gap in monitoring between the historical physiological data and the real-time physiological data.

The one or more hardware computer processors can be further configured to execute the plurality of computer executable instructions to cause the monitoring hub to establish said wireless communication between the monitoring hub and the wearable device by establishing a Bluetooth connection between the monitoring hub and the wearable device.

The one or more hardware computer processors can be further configured to execute the plurality of computer executable instructions to cause the monitoring hub to establish said wireless communication between the monitoring hub and the wearable device by establishing said wireless communication without implementing a Bluetooth pairing process.

The one or more hardware computer processors can be further configured to execute the plurality of computer executable instructions to cause the monitoring hub to establish said wireless communication between the monitoring hub and the wearable device in response to a user input, the user input comprising a non-contact user input.

The one or more hardware computer processors can be further configured to execute the plurality of computer executable instructions to cause the monitoring hub to. receive identification data via the monitoring hub using one or more of near field communication (NFC) or radio frequency identification (RFID), the identification data associated with a user requesting to establish wireless monitoring with the monitoring hub. The one or more hardware computer processors can be further configured to execute the plurality of computer executable instructions to cause the monitoring hub to determine, based on at least the identification data, that the user has permission to establish the wireless monitoring.

The one or more hardware computer processors can be further configured to execute the plurality of computer executable instructions to cause the monitoring hub to establish said wireless communication between the monitoring hub and the wearable device based on at least a proximity of the wearable device to the monitoring hub.

The one or more hardware computer processors can be further configured to execute the plurality of computer executable instructions to cause the monitoring hub to access said wireless configuration data by wirelessly receiving said wireless configuration data from the remote server.

The one or more hardware computer processors can be further configured to execute the plurality of computer executable instructions to cause the monitoring hub to access said wireless configuration data based on at least retrieving said wireless configuration data from memory.

The one or more hardware computer processors can be further configured to execute the plurality of computer executable instructions to cause the monitoring hub to render the user interface via a display of the monitoring hub.

The one or more hardware computer processors can be further configured to execute the plurality of computer executable instructions to cause the monitoring hub to historical user interface data from the remote server, the historical user interface data corresponding to the historical physiological data, the historical user interface data previously generated by the another monitoring hub.

Disclosed herein is a method of continuously monitoring a patient having a wireless wearable device while changing from a first monitoring hub to a second monitoring hub. The method can comprise, responsive to a request to establish wireless monitoring at a monitoring hub of a subject's physiology, accessing wireless configuration data governing wireless communication with a wearable device on a subject, said wireless configuration data comprising at least one or more device addresses associated with the wearable device, said wireless configuration data received at the monitoring hub from a remote server. The method can further comprise based on at least the wireless configuration data, establishing wireless communication between the monitoring hub and the wearable device to cause the monitoring hub to wirelessly receive real-time physiological data from the wearable device using one or more wireless communication protocols. The method can further comprise receiving historical physiological data from a remote server, the historical physiological data comprising physiological data collected by the wearable device before establishing the wireless communication between the monitoring hub and the wearable device, the historical physiological data comprising physiological data communicated from the wearable device to another monitoring hub before establishing the wireless communication between the monitoring hub and the wearable device. The method can further comprise generating user interface data for rendering a user interface including the real-time physiological data in combination with the historical physiological data to reduce a gap in monitoring between the historical physiological data and the real-time physiological data.

In some implementations, establishing said wireless communication between the monitoring hub and the wearable device comprises establishing a Bluetooth connection between the monitoring hub and the wearable device without implementing a Bluetooth pairing process.

The method can further comprise establishing said wireless communication between the monitoring hub and the wearable device in response to a user input, the user input comprising a non-contact user input.

The method can further comprise receiving identification data via the monitoring hub using one or more of near field communication (NFC) or radio frequency identification (RFID), the identification data associated with a user requesting to establish wireless monitoring with the monitoring hub. The method can further comprise determining, based on at least the identification data, that the user has permission to establish the wireless monitoring.

In some implementations, accessing said wireless configuration data comprises retrieving said wireless configuration data from memory.

The method can further comprise rendering the user interface via a display of the monitoring hub.

The method can further comprise receiving historical user interface data from the remote server, the historical user interface data corresponding to the historical physiological data, the historical user interface data previously generated by the another monitoring hub.

Disclosed herein is non-transitory computer-readable media including computer-executable instructions that, when executed by a computing system, cause the computing system to perform operation. The operations can comprise, responsive to a request to establish wireless monitoring at a monitoring hub of a subject's physiology. accessing wireless configuration data governing wireless communication with a wearable device on a subject, said wireless configuration data comprising at least one or more device addresses associated with the wearable device, said wireless configuration data received at the monitoring hub from a remote server. The operations can further comprise based on at least the wireless configuration data, establishing wireless communication between the monitoring hub and the wearable device to cause the monitoring hub to wirelessly receive real-time physiological data from the wearable device using one or more wireless communication protocols. The operations can further comprise receiving historical physiological data from a remote server, the historical physiological data comprising physiological data collected by the wearable device before establishing the wireless communication between the monitoring hub and the wearable device, the historical physiological data comprising physiological data communicated from the wearable device to another monitoring hub before establishing the wireless communication between the monitoring hub and the wearable device. The operations can further comprise generating user interface data for rendering a user interface including the real-time physiological data in combination with the historical physiological data to reduce a gap in monitoring between the historical physiological data and the real-time physiological data.

In some implementations, the computer-executable instructions, when executed by the computing system, further cause the computing system to perform operations comprising rendering the user interface via a display of the monitoring hub.

In some implementations, the computer-executable instructions, when executed by the computing system, further cause the computing system to perform operations comprising receiving historical user interface data from the remote server, the historical user interface data corresponding to the historical physiological data, the historical user interface data previously generated by the another monitoring hub.

Disclosed herein is a computing system configured to facilitate continuously monitoring a patient having a wireless wearable device while changing from a first monitoring hub to a second mobile monitoring hub. The computing system can comprise an in-room display device configured to electronically monitor a patient, the in-room display device including display indicia responsive to physiological data of the patient originating from a wearable device on the patient, wherein the wearable device comprises a wireless wearable device, wherein the wireless wearable device includes wireless configuration data governing wireless transmission of said physiological data from the wearable device. The computing system can further comprise one or more hardware computer processors configured to execute computer executable instructions to cause the computing system to receive, via the in-room display device, a request to transfer wireless monitoring of the patient from the in-room display device to a mobile monitoring hub, the request comprising identification data associated with a user requesting to transfer the wireless monitoring. The one or more hardware computer processors can be configured to execute the computer executable instructions to further cause the computing system to determine whether the user has permission to transfer the wireless monitoring based on at least the identification data. The one or more hardware computer processors can be configured to execute the computer executable instructions to further cause the computing system to, responsive to determining that user has permission to transfer the wireless monitoring access said wireless configuration data associated with the wireless wearable device on the patient, said wireless configuration data received from the in-room display device. The one or more hardware computer processors can be configured to execute the computer executable instructions to further cause the computing system to wirelessly transmit said wireless configuration data associated with the wireless wearable device on the patient to the mobile monitoring hub to cause the mobile monitoring hub to establish a wireless communication between the mobile monitoring hub and the wearable device.

The one or more hardware computer processors can be configured to execute the computer executable instructions to further cause the computing system to receive, via the mobile monitoring hub, second identification data. The one or more hardware computer processors can be configured to execute the computer executable instructions to further cause the computing system to determine an approval status of the request to transfer the wireless monitoring based on least comparing the identification data with second identification data.

The one or more hardware computer processors can be configured to execute the computer executable instructions to further cause the computing system to receive said identification data via the in-room display device one or more of near field communication (NFC) or radio frequency identification (RFID) a non-contact user input via the in-room display device.

The one or more hardware computer processors can be configured to execute the computer executable instructions to further cause the computing system to receive said request to transfer wireless monitoring comprising said identification data via a non-contact user input via the in-room display device.

In some implementations, the identification data comprises a serial number.

In some implementations, the identification data comprises a biological marker.

The one or more hardware computer processors can be configured to execute the computer executable instructions to further cause the computing system to determine a proximity of the wearable device to the mobile monitoring hub based on at least determining a signal strength associated with the wearable device. The one or more hardware computer processors can be configured to execute the computer executable instructions to further cause the computing system to establish said wireless communication between the mobile monitoring hub and the wearable device based on at least determining that the wearable device is within a threshold proximity of the mobile monitoring hub.

The one or more hardware computer processors can be configured to execute the computer executable instructions to further cause the computing system to, responsive to determining that user has permission to transfer the wireless monitoring wirelessly transmit historical physiological data to the mobile monitoring hub, the historical physiological data previously collected by the wearable device and communicated to the in-room display device from the wearable device.

In some implementations, the wireless configuration data comprises a device address associated with the wearable device and one or more link keys associated with establishing wireless communication with the wearable device.

The one or more hardware computer processors can be configured to execute the computer executable instructions to further cause the computing system to, responsive to an indication that the mobile monitoring hub is in a transfer mode, terminate a wireless communication connection between the in-room display device and the wearable device.

The one or more hardware computer processors can be configured to execute the computer executable instructions to further cause the computing system to receive said wireless configuration data from the in-room display device.

Disclosed herein is a method of continuously monitoring a patient having a wireless wearable device while changing from a first monitoring hub to a second mobile monitoring hub configured to travel with the patient if the patient changes location. The method can comprise electronically monitoring a patient with an in-room display device, the in-room display device including display indicia responsive to physiological data of the patient originating from a wearable device on the patient, wherein the wearable device comprises a wireless wearable device, wherein the wireless wearable device includes wireless configuration data governing wireless transmission of said physiological data from the wearable device. The method can further comprise receiving, via the in-room display device, a request to transfer wireless monitoring of the patient from the in-room display device to a mobile monitoring hub, the request comprising identification data associated with a user requesting to transfer the wireless monitoring. The method can further comprise determining whether the user has permission to transfer the wireless monitoring based on at least the identification data. The method can further comprise responsive to determining that user has permission to transfer the wireless monitoring accessing said wireless configuration data associated with the wireless wearable device on the patient, said wireless configuration data received from the in-room display device. The method can further comprise responsive to determining that user has permission to transfer the wireless monitoring wirelessly transmitting said wireless configuration data associated with the wireless wearable device on the patient to the mobile monitoring hub to cause the mobile monitoring hub to establish a wireless communication between the mobile monitoring hub and the wearable device.

The method can further comprise receiving, via the mobile monitoring hub, second identification data. The method can further comprise determining an approval status of the request to transfer the wireless monitoring based on least comparing the identification data with second identification data.

The method can further comprise receiving said identification data via the in-room display device one or more of near field communication (NFC) or radio frequency identification (RFID) a non-contact user input via the in-room display device.

The method can further comprise receiving said request to transfer wireless monitoring comprising said identification data via a non-contact user input via the in-room display device.

In some implementations, the identification data comprises one or more of a serial number or a biological marker.

In some implementations, monitoring the patient with the wearable device comprises monitoring the patient with a watch.

In some implementations, monitoring the patient with the wearable device comprises monitoring the patient with a wearable hub in communication with one or more of an ECG sensor, SpO2 sensor, a blood pressure sensor.

Disclosed herein is non-transitory computer-readable media including computer-executable instructions that, when executed by a computing system, cause the computing system to perform operations comprising: electronically monitoring a patient with an in-room display device, the in-room display device including display indicia responsive to physiological data of the patient originating from a wearable device on the patient, wherein the wearable device comprises a wireless wearable device, wherein the wireless wearable device includes wireless configuration data governing wireless transmission of said physiological data from the wearable device; receiving, via the in-room display device, a request to transfer wireless monitoring of the patient from the in-room display device to a mobile monitoring hub, the request comprising identification data associated with a user requesting to transfer the wireless monitoring; determining whether the user has permission to transfer the wireless monitoring based on at least the identification data; and responsive to determining that user has permission to transfer the wireless monitoring: accessing said wireless configuration data associated with the wireless wearable device on the patient, said wireless configuration data received from the in-room display device; and wirelessly transmitting said wireless configuration data associated with the wireless wearable device on the patient to the mobile monitoring hub to cause the mobile monitoring hub to establish a wireless communication between the mobile monitoring hub and the wearable device.

In some implementations, the computer-executable instructions, when executed by the computing system, further cause the computing system to perform operations comprising: receiving, via the mobile monitoring hub, second identification data; and determining an approval status of the request to transfer the wireless monitoring based on least comparing the identification data with second identification data.

Disclosed herein is a method of continuously monitoring a patient having a wireless wearable device while changing from a first monitoring hub to a second mobile monitoring hub configured to travel with the patient if the patient changes location. The method can comprise electronically monitoring a patient with an in-room display device. The in-room display device can include display indicia responsive to physiological data of the patient originating from a wearable device on the patient. The wearable device can comprise a wireless wearable device. The wireless wearable device can include wireless configuration data governing wireless transmission of said physiological data from the wearable device. The method can further comprise receiving a request to transfer wireless monitoring of the patient from the in-room display device to a mobile monitoring hub. The method can further comprise electronically instructing a caregiver to place the mobile monitoring hub in a transfer mode. The method can further comprise responsive to an indication that the mobile monitoring hub is in the transfer mode, accessing said wireless configuration data associated with the wireless wearable device on the patient, said wireless configuration data received from the in-room display device. The method can further comprise responsive to an indication that the mobile monitoring hub is in the transfer mode, wirelessly transmitting said wireless configuration data associated with the wireless wearable device on the patient to the mobile monitoring hub to cause the mobile monitoring hub to establish a wireless communication between the mobile monitoring hub and the wearable device. The method can further comprise responsive to an indication that the mobile monitoring hub is in the transfer mode, wirelessly transmitting historical physiological data to the mobile monitoring hub, the historical physiological data previously collected by the wearable device and communicated to the in-room display device from the wearable device.

The method can further comprise receiving, via the in-room display device, identification data associated with a user requesting to transfer the wireless monitoring. The method can further comprise determining whether the user has permission to transfer the wireless monitoring based on at least the identification data.

The method can further comprise receiving, via the in-room display device, identification data associated with a user requesting to transfer the wireless monitoring. The method can further comprise determining an approval status of the request to transfer the wireless monitoring based on least comparing the identification data with second identification data received via the mobile monitoring hub.

In some implementations, the wireless configuration data comprises a device address associated with the wearable device and one or more link keys associated with establishing wireless communication with the wearable device.

The method can further comprise responsive to the indication that the mobile monitoring hub is in the transfer mode, terminating a wireless communication connection between the in-room display device and the wearable device.

The method can further comprise receiving said wireless configuration data from the in-room display device.

The method can further comprise receiving said historical physiological data from the in-room display device.

In some implementations, monitoring the patient with the wearable device comprises monitoring the patient with a watch.

In some implementations, monitoring the patient with the wearable device comprises monitoring the patient with a wearable hub in communication with one or more of an ECG sensor, SpO2 sensor, and blood pressure sensor.

The method can further comprise wirelessly transmitting user interface data to the mobile monitoring hub, the user interface data corresponding to the historical physiological data, the user interface data previously generated by the in-room display device.

Disclosed herein is a method of continuously monitoring a patient having a wireless wearable device while changing from a first monitoring hub to a second monitoring hub. The method can comprise: according to a wireless communication protocol, establishing wireless communication between a monitoring hub and a wearable device on a subject. The monitoring hub can include display indicia responsive to physiological data of the subject originating from the wearable device. The wireless communication can comprise a wireless communication connection. The method can further comprise receiving, according to the wireless communication protocol, wireless configuration data associated with the wearable device, said wireless configuration data governing wireless communication with the wearable device. The method can further comprise receiving, at the monitoring hub, physiological data of the subject via the wireless communication between the monitoring hub and a wearable device, said physiological data originating from the wearable device. The method can further comprise communicating said physiological data to a remote server. The method can further comprise communicating at least a portion of said wireless configuration data associated with the wearable device to the remote server, the at least a portion of said wireless configuration data comprising at least one or more device addresses associated with the wearable device, the one or more device addresses configured to facilitate wireless communication with the wearable device.

The method can further comprise communicating said physiological data or said wireless configuration data to the remote server in response to a request to transfer physiological monitoring from the monitoring hub to another monitoring hub.

In some implementations, establishing said wireless communication between the monitoring hub and the wearable device comprises establishing a Bluetooth connection between the monitoring hub and the wearable device.

The method can further comprise communicating user interface data to the remote server, the user interface data corresponding to the physiological data, the user interface data generated by the monitoring hub.

Disclosed herein is a method of monitoring a patient location wearing a wearable device. The method can comprise: detecting, at a monitoring hub, a wireless configuration signal from a wearable device on a patient. The wireless configuration signal can comprise at least a portion of a paging process of a Bluetooth communication protocol. The method can further comprise determining whether the wearable device is within a threshold proximity of the monitoring hub based on at least a signal strength associated with the wireless configuration signal. The method can further comprise in response to determining that the wearable device is within the threshold proximity of the monitoring hub, establishing wireless communication between the wearable device and the monitoring hub according to a Bluetooth communication protocol, the wireless communication comprising a Bluetooth connection. The method can further comprise in response to establishing said wireless communication, determining a location of a subject based on a least determining a location of the monitoring hub in an environment.

Disclosed herein is a method of continuously monitoring a patient having a wireless wearable device while changing from a first monitoring hub to a second monitoring hub. The method can comprise accessing wireless configuration data governing wireless communication with one or more sensors coupled to a subject, said wireless configuration data comprising at least one or more device addresses associated with the one or more sensors. The method can comprise receiving a user input to establish a wireless communication between a monitoring hub and the one or more sensors, said user input comprising a non-contact user input. The method can comprise responsive to said user input, establishing wireless communication between the monitoring hub and the one or more sensors based on at least the wireless configuration data, to cause the monitoring hub to wirelessly receive real-time physiological data from the one or more sensors.

The method can comprise determining a proximity of the one or more sensors to the monitoring hub based on at least determining a signal strength associated with the one or more sensors. The method can further comprise establishing said wireless communication between the monitoring hub and the one or more sensors based on at least determining that the one or more sensors are within a threshold proximity of the monitoring hub.

In some implementations, receiving said non-contact user input comprises receiving, via the monitoring hub, a wireless signal associated with one or more of near field communication (NFC) or radio frequency identification (RFID).

Disclosed herein is a method of continuously monitoring a patient having a wireless wearable device while changing from a first monitoring hub to a second monitoring hub. The method can comprise accessing wireless configuration data governing wireless communication with a plurality sensors coupled to a subject, said wireless configuration data comprising at least one or more device addresses associated with the plurality of sensors. The method can further comprise receiving a user input to establish a wireless communication between a monitoring hub and the plurality of sensors, said user input comprising a single user input. The method can further comprise responsive to said single user input, establishing wireless communication between the monitoring hub and the plurality of sensors, based on at least the wireless configuration data, to cause the monitoring hub to wirelessly receive real-time physiological data from the plurality of sensors.

In some implementations, receiving said user input comprises receiving, via the monitoring hub, a non-contact user input.

Disclosed herein is a monitoring hub for monitoring a subject's physiological status, the monitoring hub comprising: a communication component; a computer readable storage medium having program instructions embodied therewith; and one or more processors. The communication component can be configured to: communicate wirelessly with one or more sensors to communicate physiological data and communication data with the one or more sensors; and communicate wirelessly with a physiological monitoring system to communicate physiological data and communication data with the physiological monitoring system. The one or more processors can be configured to execute the program instructions to cause the monitoring hub to: receive a request to perform a transfer operation; receive identification data; verify permissions of the request based at least in part on the identification data; establish communication, via the communication component, with another monitoring hub, whereby the communication component is configured to communicate wirelessly with the another monitoring hub to communicate physiological data or communication data with the another monitoring hub; determine an approval status of the request to perform the transfer operation based at least in part on the identification data; in response to determining that the request to perform the transfer operation is approved, cause the communication component to communicate physiological data or communication data to the another monitoring hub; and terminate a wireless communication connection between the communication component and the one or more sensors.

In some implementations, the one or more processors are further configured to execute the program instructions to cause the monitoring hub to receive the identification data via the communication component. In some implementations, the one or more processors are further configured to execute the program instructions to cause the monitoring hub to receive the identification data using near field communication (NFC) of the communication component. In some implementations, the one or more processors are further configured to execute the program instructions to cause the monitoring hub to receive the identification data via a user input or display of the monitoring hub. In some implementations, the identification data includes a user identification. In some implementations, the one or more processors are further configured to execute the program instructions to cause the monitoring hub to receive, via the communication component, a second identification data. In some implementations, the one or more processors are further configured to execute the program instructions to cause the monitoring hub to compare the identification data with the second identification data to determine if the identification data matches the second identification data. In some implementations, the one or more processors are further configured to execute the program instructions to cause the monitoring hub to determine the approval status of the request based at least in part on comparing the identification data with the second identification data. In some implementations, the one or more processors are further configured to execute the program instructions to cause the monitoring hub to determine that the request to perform the transfer operation is approved if the identification data matches the second identification data. In some implementations, the one or more processors are further configured to execute the program instructions to cause the monitoring hub to determine that the request to perform the transfer operation is approved if a user identification of the identification data matches a user identification of the second identification data. In some implementations, the one or more processors are further configured to execute the program instructions to cause the monitoring hub to communicate, via the communication component, the identification data to the another monitoring hub. In some implementations, the one or more processors are further configured to execute the program instructions to cause the monitoring hub to communicate, via the communication component, the identification data to the physiological monitoring system. In some implementations, the one or more processors are further configured to execute the program instructions to cause the monitoring hub to receive, via the communication component, the approval status of the request from the another monitoring hub. In some implementations, the one or more processors are further configured to execute the program instructions to cause the monitoring hub to communicate, via the communication component, the approval status of the request from the physiological monitoring system. In some implementations, the one or more processors are further configured to execute the program instructions to cause the monitoring hub to, in response to determining that the request to perform the transfer operation is approved, cause the communication component to communicate physiological data or communication data to the physiological monitoring system. In some implementations, the physiological data includes one or more of raw physiological data obtained from the one or more sensors, processed physiological data, or physiological parameter values. In some implementations, the physiological data includes historical physiological data. In some implementations, the communication data includes one or more device addresses of the one or more sensors. In some implementations, the one or more processors are further configured to execute the program instructions to cause the monitoring hub to receive, via the communication component, communication data from the another monitoring hub. In some implementations, the one or more processors are further configured to execute the program instructions to cause the monitoring hub to communicate, via the communication component, the communication data received from the another monitoring hub to the one or more sensors. In some implementations, the communication data received from the another monitoring hub includes a device address of the another monitoring hub. In some implementations, the one or more processors are further configured to execute the program instructions to cause the monitoring hub to receive, via the communication component, confirmation that the transfer operation was completed. In some implementations, the one or more processors are further configured to execute the program instructions to cause the monitoring hub to receive the confirmation from the another monitoring hub or from the physiological monitoring system. In some implementations, the confirmation includes an indication that the another monitoring hub has established a wireless communication connection with the one or more sensors. In some implementations, the communication component includes a transceiver. In some implementations, the communication component is further configured to communicate with the one or more sensors using one or more wireless communication protocols including WiFi, Bluetooth, near field communication (NFC), radio frequency identification (RFID), cellular, 1G, 2G, 3G, 4G, 5G, or Zigbee. In some implementations, the communication component is further configured to communicate with the physiological monitoring system using one or more wireless communication protocols including WiFi, Bluetooth, near field communication (NFC), radio frequency identification (RFID), cellular, 1G, 2G, 3G, 4G, 5G, or Zigbee. In some implementations, the communication component is further configured to communicate with the another monitoring hub using one or more wireless communication protocols including WiFi, Bluetooth, near field communication (NFC), radio frequency identification (RFID), cellular, 1G, 2G, 3G, 4G, 5G, or Zigbee. In some implementations, the one or more processors are further configured to execute the program instructions to receive the request to perform the transfer operation via a user input of the monitoring hub. In some implementations, verifying the permissions of the request includes verifying permissions of a user associated with the request. In some implementations, the one or more processors are further configured to execute the program instructions to cause the communication component to communicate a transfer signal to the physiological monitoring system to initiate the transfer operation. In some implementations, the one or more processors are further configured to execute the program instructions to cause the communication component to communicate physiological data or communication data to the physiological monitoring system to initiate the transfer operation. In some implementations, the physiological data includes historical physiological data. In some implementations, the communication data includes one or more device addresses of the one or more sensors.

Disclosed herein is a monitoring hub for monitoring a subject's physiological status, the monitoring hub comprising: a communication component; a computer readable storage medium having program instructions embodied therewith; and one or more processors. In some implementations, the communication component is configured to: communicate wirelessly with one or more sensors to communicate physiological data and communication data with the one or more sensors; and communicate wirelessly with a physiological monitoring system to communicate physiological data and communication data with the physiological monitoring system. In some implementations, the one or more processors are configured to execute the program instructions to cause the monitoring hub to: receive a request to perform a transfer operation; receive identification data; establish communication, via the communication component, with another monitoring hub, whereby the communication component is configured to communicate wirelessly with the another monitoring hub to communicate physiological data or communication data with the another monitoring hub; determine an approval status of the request to perform the transfer operation based at least in part on the identification data; in response to determining that the request to perform the transfer operation is approved, receive, via the communication component, physiological data or communication data from the another monitoring hub; and establish a wireless communication connection between the communication component and the one or more sensors.

In some implementations, the one or more processors are further configured to execute the program instructions to cause the monitoring hub to receive the identification data via the communication component. In some implementations, the one or more processors are further configured to execute the program instructions to cause the monitoring hub to receive the identification data using near field communication (NFC) of the communication component. In some implementations, the one or more processors are further configured to execute the program instructions to cause the monitoring hub to receive the identification data via a user input or display of the monitoring hub. In some implementations, the identification data includes a user identification. In some implementations, the one or more processors are further configured to execute the program instructions to cause the monitoring hub to receive, via the communication component, a second identification data. In some implementations, the one or more processors are further configured to execute the program instructions to cause the monitoring hub to compare the identification data with the second identification data to determine if the identification data matches the second identification data. In some implementations, the one or more processors are further configured to execute the program instructions to cause the monitoring hub to determine the approval status of the request based at least in part on comparing the identification data with the second identification data. In some implementations, the one or more processors are further configured to execute the program instructions to cause the monitoring hub to determine that the request to perform the transfer operation is approved if the identification data matches the second identification data. In some implementations, the one or more processors are further configured to execute the program instructions to cause the monitoring hub to determine that the request to perform the transfer operation is approved if a user identification of the identification data matches a user identification of the second identification data. In some implementations, the one or more processors are further configured to execute the program instructions to cause the monitoring hub to communicate, via the communication component, the identification data to the another monitoring hub. In some implementations, the one or more processors are further configured to execute the program instructions to cause the monitoring hub to communicate, via the communication component, the identification data to the physiological monitoring system. In some implementations, the one or more processors are further configured to execute the program instructions to cause the monitoring hub to receive, via the communication component, the approval status of the request from the another monitoring hub. In some implementations, the one or more processors are further configured to execute the program instructions to cause the monitoring hub to communicate, via the communication component, the approval status of the request from the physiological monitoring system. In some implementations, the one or more processors are further configured to execute the program instructions to cause the monitoring hub to, in response to determining that the request to perform the transfer operation is approved, receive, via the communication component physiological data or communication data from the physiological monitoring system. In some implementations, the physiological data includes one or more of raw physiological data obtained from the one or more sensors, processed physiological data, or physiological parameter values. In some implementations, the physiological data includes historical physiological data. In some implementations, the communication data includes one or more device addresses of the one or more sensors. In some implementations, the one or more processors are further configured to execute the program instructions to cause the monitoring hub to communicate, via the communication component, confirmation that the transfer operation was completed. In some implementations, the one or more processors are further configured to execute the program instructions to cause the monitoring hub to communicate the confirmation to the another monitoring hub or to the physiological monitoring system. In some implementations, the confirmation includes an indication that the monitoring hub has established a wireless communication connection with the one or more sensors. In some implementations, the communication component includes a transceiver. In some implementations, the communication component is further configured to communicate with the one or more sensors using one or more wireless communication protocols including WiFi, Bluetooth, near field communication (NFC), radio frequency identification (RFID), cellular, 1G, 2G, 3G, 4G, 5G, or Zigbee. In some implementations, the communication component is further configured to communicate with the physiological monitoring system using one or more wireless communication protocols including WiFi, Bluetooth, near field communication (NFC), radio frequency identification (RFID), cellular, 1G, 2G, 3G, 4G, 5G, or Zigbee. In some implementations, the communication component is further configured to communicate with the another monitoring hub using one or more wireless communication protocols including WiFi, Bluetooth, near field communication (NFC), radio frequency identification (RFID), cellular, 1G, 2G, 3G, 4G, 5G, or Zigbee. In some implementations, the one or more processors are further configured to execute the program instructions to cause the monitoring hub to receive the request to perform the transfer operation via a user input of the monitoring hub. In some implementations, the one or more processors are further configured to execute the program instructions to cause the communication component to communicate physiological data or communication data to the physiological monitoring system. In some implementations, the one or more processors are further configured to execute the program instructions to cause the monitoring hub to receive, via the communication component, physiological data from the one or more sensors. In some implementations, the one or more processors are further configured to execute the program instructions to display, via a display of the monitoring hub, the physiological data received from the one or more sensors and historical physiological data.

Disclosed herein is a physiological monitoring system for monitoring a subject's physiological status, the physiological monitoring system comprising: a computer readable storage medium having program instructions embodied therewith; and one or more processors. The one or more processors can be configured to execute the program instructions to cause the physiological monitoring system to: receive a request to perform a transfer operation from one or more monitoring hubs; determine an approval status of the request to perform the transfer operation; in response to determining that the request to perform the transfer operation is approved: receive monitoring hub communication data from the one or more monitoring hubs; access sensor communication data: establish a wireless communication connection between a first monitoring hub of the one or more monitoring hubs and the one or more sensors; and terminate a wireless communication connection between a second monitoring hub of the one or more monitoring hubs and the one or more sensors.

In some implementations, the one or more processors are further configured to execute the program instructions to cause the physiological monitoring system to determine the approval status based in least in part on one or more signal received from the one or more monitoring hubs. In some implementations, the one or more processors are further configured to execute the program instructions to cause the physiological monitoring system to receive first and second identification data from the one or more monitoring hubs. In some implementations, the first and second identification data include user identifications. In some implementations, the one or more processors are further configured to execute the program instructions to cause the physiological monitoring system to compare the first identification data with the second identification data to determine if the first identification data matches the second identification data. In some implementations, the one or more processors are further configured to execute the program instructions to cause the physiological monitoring system to determine the approval status of the request based at least in part on comparing the first identification data with the second identification data. In some implementations, the one or more processors are further configured to execute the program instructions to cause the physiological monitoring system to determine that the request to perform the transfer operation is approved if the first identification data matches the second identification data. In some implementations, the one or more processors are further configured to execute the program instructions to cause the physiological monitoring system to determine that the request to perform the transfer operation is approved if a user identification of the first identification data matches a user identification of the second identification data. In some implementations, the monitoring hub communication data includes a device address of the first monitoring hub. In some implementations, the sensor communication data includes one or more device addresses of the one or more sensors. In some implementations, the one or more processors are further configured to execute the program instructions to cause the physiological monitoring system to communicate the monitoring hub communication data to the one or more sensors. In some implementations, the one or more processors are further configured to execute the program instructions to cause the physiological monitoring system to communicate the sensor communication data to the first monitoring hub. In some implementations, the one or more processors are further configured to execute the program instructions to cause the physiological monitoring system to access historical physiological data. In some implementations, the one or more processors are further configured to execute the program instructions to cause the physiological monitoring system to communicate historical physiological data to the first monitoring hub.

Disclosed herein is a method of transferring a wireless connection that is between a first medical monitoring device and one or more physiological sensors to a wireless connection that is between a second medical monitoring device and said one or more physiological sensors, said second medical monitoring device being different than said first medical monitoring device, wherein the method comprises: receiving a request to transfer said wireless connection; receiving, with said first medical monitoring device, first identification data; receiving, with said second medical monitoring device, second identification data; comparing the second identification data to the first identification data; and initiating, based on said comparison, said transfer of said wireless connection to enable wireless communication between said one or more physiological sensors and said second medical monitoring device.

In some implementations, said receiving said request to transfer said wireless connection comprises receiving user input at the first medical monitoring device. In some implementations, said comparing the second identification data to the first identification data is performed by one or more of: the first medical monitoring device; the second medical monitoring device; a third medical monitoring device; or a server. In some implementations, said initiating said transfer comprises receiving, with the second medical monitoring device, communication data associated with each of the one or more physiological sensors. In some implementations, said initiating said transfer comprises transmitting communication data associated with each of the one or more physiological sensors to the second medical monitoring device. In some implementations, said transmitting said communication data is performed by a server in communication with the first and second medical monitoring devices. In some implementations, said transmitting said communication data is performed by the first medical monitoring device. In some implementations, said initiating said transfer comprises receiving, with the one or more physiological sensors, communication data associated with the second medical monitoring device. In some implementations, said initiating said transfer comprises transmitting communication data associated with the second medical monitoring device to each of the one or more physiological sensors. In some implementations, said transmitting said communication data is performed by the first medical monitoring device. In some implementations: said comparing the second identification data to the first identification data comprises determining whether the second identification data is associated with the first identification data; and said method comprises initiating said transfer of said wireless connection responsive to determining that the second identification data is associated with the first identification data. In some implementations: said comparing the second identification data to the first identification data comprises determining whether the second identification data matches the first identification data; and said method comprises initiating said transfer of said wireless connection responsive to determining that the second identification data matches the first identification data. In some implementations, the first identification data is associated with a user. In some implementations, the first identification data is associated with a healthcare provider. In some implementations, a user is not required to terminate a wireless connection between the wireless sensor and the first medical monitoring device. In some implementations, the first medical monitoring device is not directly connected with the second medical monitoring device with a wired or wireless connection. In some implementations, the method further comprises automatically terminating a wireless connection between the wireless sensor and the first medical monitoring device in response to determining that the second identification data matches the first identification data. In some implementations, Bluetooth multipoint is not enabled. In some implementations, the wireless sensor is configured to wirelessly connect with a single medical monitoring device at a time.

Disclosed herein is a method of transferring a wireless connection that is between a first medical monitoring device and one or more physiological sensors to a wireless connection that is between a second medical monitoring device and said one or more physiological sensors, said second medical monitoring device being different than said first medical monitoring device, wherein the method comprises: receiving first information relating to said transfer of said wireless connection; receiving second information relating to said transfer of said wireless connection; and initiating said transfer of said wireless connection to enable wireless communication between said one or more physiological sensors and said second medical monitoring device based at least on the received first and second information, wherein initiating said transfer does not require a user to terminate said wireless connection between said first medical monitoring device and said one or more physiological sensors.

In some implementations, said first information comprises first identification data. In some implementations, said first identification data is associated with a user. In some implementations, said first identification data is associated with a healthcare provider. In some implementations, said second information comprises second identification data. In some implementations, said second identification data is associated with a user. In some implementations, said second identification data is associated with a healthcare provider. In some implementations, said initiating said transfer of said wireless connection comprises determining that at least a portion of the first information matches at least a portion of the second information. In some implementations, initiating the change does not require the user to change a pairing mode of the wireless sensor. In some implementations, initiating the change does not require the user to power the wireless sensor off.

Disclosed herein is a mounting assembly for mounting an electronic device to a support surface, the mounting assembly comprising: a first mount configured to be secured to a portion of the electronic device; and a second mount configured to be secured to the support surface. The first mount can be configured to be removably secured to the second mount, thereby mounting the electronic device to the support surface.

In some implementations, said electronic device is a monitoring hub, such as any of the monitoring hubs disclosed herein, with any of the features and/or functionality described with respect to any of the monitoring hubs disclosed herein. In some implementations, said support surface is a wall. In some implementations, said support surface is on a support arm that is secured to a wall. In some implementations, the first mount is configured to be secured to the second mount without using a screw and/or without using a nail. In some implementations, the first mount is configured to be secured to the second mount by inserting a portion of the first mount into a portion of the second mount. In some implementations, the first mount is configured to be secured to the second mount by moving the first mount in a first direction relative to the second mount, and wherein the first mount is configured to be removed from the second mount by moving the first mount in a second direction relative to the second mount that is opposite to the first direction. In some implementations, the second mount comprises one or more fingers configured to engage portions of the first mount. In some implementations: the second mount comprises a base and said one or more fingers; said one or more fingers extend outward from the base such that a gap exists between a portion of each of the one or more fingers and a surface of the base; and said gap is configured to receive said portions of the first mount. In some implementations, said one or more fingers are configured to vertically support said portions of the first mount. In some implementations, said one or more fingers form a funneled pocket that vertically supports said portions of the first mount. In some implementations, said portions of the first mount that are vertically supported by said one or more fingers are part of a base of the first mount, said base having a width that tapers along at least a portion of a height of the base. In some implementations: one of the first or second mounts comprises a lever configured to be moved from a first position to a second position; and when the lever is in the first position, detachment of the first mount from the second mount is inhibited. In some implementations: the second mount comprises a lever configured to be moved from a first position to a second position; when the lever is in the first position, a portion of the lever engages a portion of the first mount, thereby resulting in a physical interference that inhibits the first mount from being detached from the second mount; and when the lever is in the second position, said physical interference is removed. In some implementations: said lever comprises a protrusion and said first mount comprises an opening; when the lever is in the first position, said protrusion of the lever engages a portion of the first mount proximate the opening of the first mount, thereby resulting in said physical interference. In some implementations, when the lever is in the first position, said protrusion of the lever is positioned at least partially within said opening of the first mount. In some implementations, when the lever is in the second position, said protrusion of the lever is positioned outside said opening of the first mount.

Disclosed herein is a holder for receiving an electronic device, the holder comprising: a base configured to receive at least a portion of the electronic device; a first arm extending outward from the base, the first arm oriented nonparallel relative to the base such that, when the first arm is positioned atop a support surface, the base is oriented nonparallel relative to said support surface; and a second arm extending outward from the base and spaced from the first arm, the second arm comprising a hook configured to secure around a portion of an object.

In some implementations, the object is a hospital bed and said portion comprises a wall or rail of the hospital bed. In some implementations, the first arm comprises a first end connected to a first portion of the base and a second end connected to a second portion of the base, thereby forming a loop of the holder. In some implementations, the second arm comprises a first end connected to a first portion of the base and a second end connected to a second portion of the base, thereby forming a loop of the holder. In some implementations, the holder further comprises a bar extending from a first portion of the first arm to a second portion of the first arm, said bar splitting said loop into a first loop portion and a second loop portion. In some implementations, the first arm is connected to a first end of the base and the second arm is connected to a second end of the base that is opposite the first end of the base. In some implementations, the holder is configured such that, when the second arm is wrapped around and/or rests atop a top portion of a support structure, the first arm contacts the support structure and operably positions the base away from the support structure. In some implementations, the holder is configured such that, when the second arm is wrapped around and/or rests atop the top portion of the support structure, the first arm contacts the support structure and operably positions the base such that the base is oriented substantially parallel relative to a plane extending along the support structure. In some implementations, said support structure is generally perpendicular to a ground surface. In some implementations, the holder is configured such that, when the second arm is wrapped around and/or rests atop the top portion of the support structure, the first arm contacts the support structure and operably positions the base to be generally perpendicular to the ground surface. In some implementations, the holder is configured such that, when the second arm is wrapped around and/or rests atop the top portion of the support structure, the first arm contacts the support structure and operably positions the base to be within 30 degrees of being perpendicular to the ground surface. In some implementations, the holder is configured such that, when the second arm is wrapped around and/or rests atop the top portion of the support structure, the first arm contacts the support structure and operably positions the base to be within 20 degrees of being perpendicular to the ground surface. In some implementations, the holder is configured such that, when the second arm is wrapped around and/or rests atop the top portion of the support structure, the first arm contacts the support structure and operably positions the base to be within 10 degrees of being perpendicular to the ground surface.

Various combinations of the above and below recited features, embodiments, implementations, and aspects are also disclosed and contemplated by the present disclosure.

Additional implementations of the disclosure are described below in reference to the appended claims, which may serve as an additional summary of the disclosure.

In various implementations, systems and/or computer systems are disclosed that comprise a computer-readable storage medium having program instructions embodied therewith, and one or more processors configured to execute the program instructions to cause the systems and/or computer systems to perform operations comprising one or more aspects of the above- and/or below-described implementations (including one or more aspects of the appended claims).

In various implementations, methods and/or computer-implemented methods are disclosed in which, by one or more processors executing program instructions, one or more aspects of the above- and/or below-described implementations (including one or more aspects of the appended claims) are implemented and/or performed.

In various implementations, computer program products comprising a computer-readable storage medium are disclosed, wherein the computer-readable storage medium has program instructions embodied therewith, the program instructions executable by one or more processors to cause the one or more processors to perform operations comprising one or more aspects of the above- and/or below-described implementations (including one or more aspects of the appended claims).

BRIEF DESCRIPTION OF THE DRAWINGS

Various implementations will be described hereinafter with reference to the accompanying drawings. These implementations are illustrated and described by example only, and are not intended to limit the scope of the disclosure. In the drawings, similar elements may have similar reference numerals.

FIGS. 5A-5D are flowcharts illustrating example processes associated with transferring physiological monitoring from an origin monitoring hub to a destination monitoring hub.

FIGS. 7F-7K illustrate front, rear, top, bottom, left side, and right side views (respectively) of the monitoring hub of FIG. 7A in accordance with aspects of this disclosure.

FIGS. 11A-11C illustrate front, rear, and side views (respectively) of another implementation of a monitoring hub in accordance with aspects of this disclosure.

DETAILED DESCRIPTION

Figures 1A, 1B:
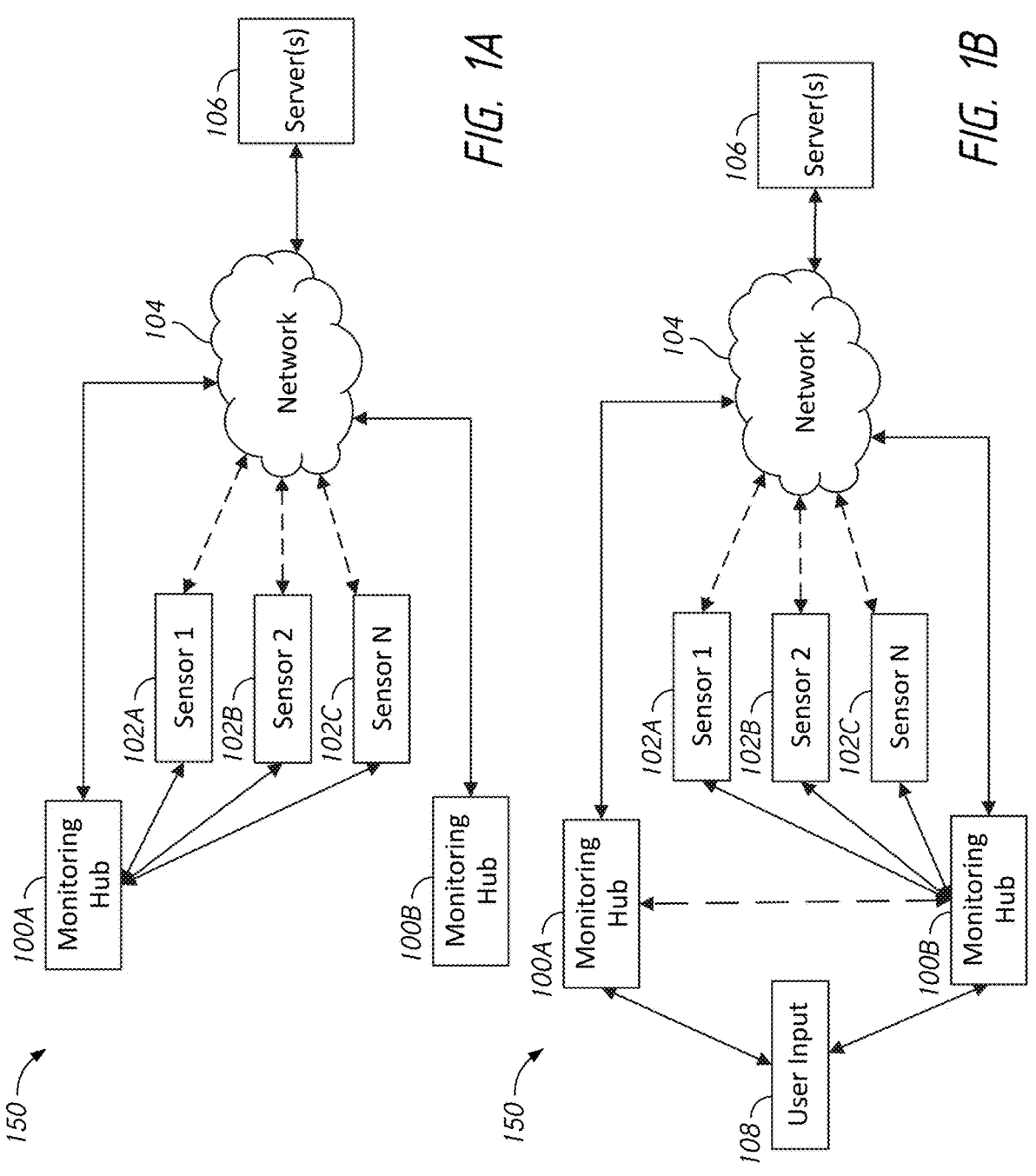
FIGS. 1A-1B are schematic block diagrams illustrating example implementations of a physiological monitoring system (PMS).

Although certain implementations, embodiments, and examples are disclosed below, the inventive subject matter extends beyond the specifically disclosed implementations to other alternative implementations and/or uses and to modifications and equivalents thereof. Thus, the scope of the claims appended hereto is not limited by any of the particular implementations described below. For example, in any method or process disclosed herein, the acts or operations of the method or process may be performed in any suitable sequence and are not necessarily limited to any particular disclosed sequence. Various operations may be described as multiple discrete operations in turn, in a manner that may be helpful in understanding certain implementations; however, the order of description should not be construed to imply that these operations are order dependent. Additionally, the structures, systems, and/or devices described herein may be embodied as integrated components or as separate components. For purposes of comparing various implementations, certain aspects and advantages of these implementations are described. Not necessarily all such aspects or advantages are achieved by any particular implementation. Thus, for example, various implementations may be carried out in a manner that achieves or optimizes one advantage or group of advantages as taught herein without necessarily achieving other aspects or advantages as may also be taught or suggested herein.

Overview

A physiological monitoring system (PMS) can monitor a patient or subject including physiological data of the subject. One or more physiological sensors can be coupled to the subject and can obtain physiological data of the subject. The one or more sensors can communicate physiological data to a monitoring hub which can display indicia of the physiological data. A user may desire to use another monitoring hub to monitor the subject such as to receive and display physiological data obtained from the sensors. The user can request the PMS to transfer physiological monitoring from the initial monitoring hub to the other monitoring hub. Described herein are systems, devices, processes, etc. for transferring physiological monitoring of a PMS from one monitoring hub to another monitoring hub and which can provide numerous benefits including improved physiological monitoring, improved health care services, and the like.

Advantageously, the systems, devices, and processes described herein can facilitate faster, simpler, and more efficient transfer of physiological monitoring from one monitoring hub to another monitoring hub. For example, a user may be able to transfer physiological monitoring from one monitoring hub to another monitoring hub without having to unplug, plug, and/or replug cables, wiring, etc. of the monitoring hubs and/or physiological sensors. As another example, a user may be able to transfer physiological monitoring from one monitoring hub to another monitoring hub without having to turn off and/or turn on devices connected to the monitoring hubs such as physiological sensors. As another example, a user may be able to transfer physiological monitoring from one monitoring hub to another monitoring hub without having to implement a time-consuming wireless pairing process. As another example, the PMS provides an intuitive and easy-to-use system for transferring physiological monitoring which can reduce time a health care provider must spend to oversee the subject's physiological monitoring and which can improve the quality of health care services provided to the subject.

Advantageously, the systems, devices, and processes described herein can reduce and/or eliminate data loss while transferring physiological monitoring from one monitoring hub to another monitoring hub. For example, a PMS may be configured to continuously monitor the physiology of the subject while transferring physiological monitoring from one monitoring hub to another monitoring hub. A PMS can be configured to retain (e.g., store) physiological data obtained from sensor(s) before, during, and/or after transferring physiological monitoring between monitoring hubs. A PMS can be configured to exchange physiological data between monitoring hubs to allow a user to view historical physiological data in combination with present or real-time physiological data. For example, a monitoring hub of a PMS can be configured to display real-time physiological data received from sensors in addition to historical physiological data that was received from the sensor by another monitoring hub previous to transferring physiological monitoring as if the monitoring hub had been monitoring the subject the entire time and had received all physiological data from the sensors directly.

Advantageously, the systems, devices, and processes described herein for transferring physiological monitoring of a PMS can improve patient mobility. For example, a PMS may facilitate simple, quick, and efficient transfer of physiological monitoring from one monitoring hub (which may be at a fixed location such as a patient room in a hospital) to another monitoring hub (such as a portable monitoring hub) while continuing to monitor the patient which can allow the patient to relocate to a different location such as a different room in a hospital. Moreover, as a patient moves within an environment, such as a hospital, the PMS can facilitate automatic wireless communication between sensors coupled to the patient and monitoring hubs within a proximity of the patient. For example, sensors coupled to a patient may automatically establish a wireless connection, such as a Bluetooth connection, with the nearest monitoring hub as the patient moves around in an environment having multiple monitoring hubs.

Advantageously, the systems, devices, and processes described herein can improve patient location tracking. For example, a PMS may monitor a patient's location, such as within a hospital, by identifying which monitoring hub are wirelessly connected to sensors attached to the patient. As the patient moves within an environment the sensor's coupled to the patient may wirelessly connect and/or communicate with various monitoring hubs, such as monitoring hubs within a close proximity to the sensors. Accordingly, a PMS can track a patient's location which can improve a quality of healthcare provided to the patient by quickly and efficiently having knowledge of the patient's location at all times, such as whether the patient is in a particular portion of a hospital they are supposed to be or have been assigned or scheduled to be, such as in an operating room.

Advantageously, the systems, devices, and processes described herein for transferring physiological monitoring of a PMS can facilitate removing, adding, replacing, and/or exchanging monitoring hubs within the PMS such as for example when a monitoring hub is low on battery power and should be replaced by another monitoring hub to continue monitoring a subject which can for example improve PMS performance as well as health care services.

Advantageously, the systems, devices, and processes described herein for transferring physiological monitoring of a PMS can improve quality control of health care services. For example, the PMS can be configured to verify the permissions associated with a user requesting to transfer physiological monitoring from one monitoring hub to another. For example, the PMS may be configured to reject a request to transfer physiological monitoring from a health care provider who does not have permission to relocate a subject being monitored and/or a health care provider who is not assigned to provide health care to the subject.

Advantageously, the systems, devices, processes described herein can improve fidelity of transferring physiological monitoring from one monitoring hub to another monitoring hub. For example, the PMS may be configured to verify a requesting user ID at a first monitoring hub and at a subsequent monitoring hub to ensure that the user IDs correspond (e.g., match) which may ensure that the PMS transfers physiological monitoring to the correct monitoring hub (e.g., to the monitoring with a requesting user ID that matches to the requesting user ID of the initial monitoring hub) which may advantageously improve transfer fidelity and accuracy in a system with numerous monitoring hubs and/or numerous requests to transfer occurring at or near the same time.

To facilitate an understanding of the systems and methods discussed herein, several terms are described below. These terms, as well as other terms used herein, should be construed to include the provided descriptions, the ordinary and customary meanings of the terms, and/or any other implied meaning for the respective terms, wherein such construction is consistent with context of the term. Thus, the descriptions below do not limit the meaning of these terms, but only provide example descriptions.

In some implementations, a sensor can comprise a wearable device. A sensor can comprise a wireless wearable device. A wearable device can include one or more sensors. A wearable device can comprise a wearable hub in communication with one or more sensors. A sensor can comprise an auricular device such as an earbud, earpiece, headphone, earphone, or the like. A sensor can comprise a wrist-worn device such as a smartwatch. A sensor can comprise a physiological sensor. A sensor can collect physiological data from a subject such as ECG data, EEG data, blood oxygenation data, heart rate data, pulse data, respiration data, blood pressure data, motion data, orientation data, temperature data, etc. A sensor can be coupled to a subject. A sensor may be attached to a subject. A sensor can be donned by a subject. A sensor can be worn by a subject. A sensor can be secured to a subject by adhesion. A sensor can be secured to a subject by one or more straps. A sensor may be worn on and/or attached to a finger, wrist, arm, forearm, head, forehead, ear, chest, back, torso, stomach, leg, ankle, foot, toe, or other body portion of a subject. A plurality of sensors can be disposed within a same housing or device. Sensors may be disposed within separate housings or devices.

In some implementations, a monitoring hub can comprise an electronic device configured to facilitate physiological monitoring of a patient. A monitoring hub can display indicia corresponding to physiological data of the patient. A monitoring hub can be mobile. A monitoring hub can be portable. A monitoring hub may comprise a hand-held device. A monitoring hub may be carried by a user. A monitoring hub can be mounted to a wall. A monitoring hub may comprise an in-room display. A monitoring hub may be stationary. A monitoring hub may be at a fixed location. A monitoring hub may comprise a tablet, monitor, PC, phone, wearable device, such as a smartwatch, or the like. A monitoring hub may communicate with one or more remote computing devices via one or more wireless communication protocols. A monitoring hub may communicate with a remote server. A monitoring hub may communicate with one or more sensors. A monitoring hub may also be referred to herein as a hub, an electronic device, a display device, a monitoring device, or the like.

In some implementations, an origin monitoring hub can refer to a monitoring hub in wireless communication with one or more sensors prior to transferring physiological monitoring to another monitoring hub. An origin monitoring hub can comprise any of the example monitoring hubs shown and/or described herein including structural and/or operational features of any of the example monitoring hubs shown and/or described herein. An origin monitoring hub may also be referred to herein as a first monitoring hub, an initial monitoring hub, or the like.

In some implementations, a destination monitoring hub can refer to a monitoring hub in wireless communication with one or more sensors subsequent to transferring physiological monitoring from another monitoring hub. A destination monitoring hub can comprise any of the example monitoring hubs shown and/or described herein including structural and/or operational features of any of the example monitoring hubs shown and/or described herein. A destination monitoring hub may also be referred to herein as a second monitoring hub, a subsequent monitoring hub, another monitoring hub, or the like.

A destination monitoring hub may comprise a different type of monitoring hub than an origin monitoring hub. For example, one of the destination monitoring hub or the origin monitoring hub may comprise a mobile monitoring hub while the other of the destination monitoring hub or the origin monitoring hub comprises a monitoring hub in a fixed location, such as a wall-mounted monitoring hub or an in-room monitoring hub. A destination monitoring hub may comprise a same type of monitoring hub as an origin monitoring hub. For example, a destination monitoring hub and an origin monitoring hub may both comprise mobile monitoring hubs.

In some implementations, "transferring physiological monitoring" can refer to transferring the monitoring, displaying, and/or collection of physiological data from an origin monitoring hub to a destination monitoring hub. Transferring physiological monitoring can include transferring a wireless connection between sensor(s) and an origin monitoring hub to sensor(s) and a destination monitoring hub. Transferring physiological monitoring can include updating or changing a wireless connection of physiological sensor(s) and/or updating or changing a wireless connection of monitoring hub(s). Transferring physiological monitoring can include terminating wireless communication between an origin monitoring hub and sensors. Transferring physiological monitoring can include establishing a wireless communication between a destination monitoring hub and sensors. In some implementations, transferring physiological monitoring can include transferring less than all of the wireless connections to sensors from an origin monitoring hub to a destination monitoring hub. In some implementations, transferring physiological monitoring can include transferring all of the wireless connections to sensors from an origin monitoring hub to a destination monitoring hub.

In some implementations, a transfer request can include a request to transfer physiological monitoring from an origin monitoring hub to a destination monitoring hub. A transfer request can be received via a user input at a monitoring hub. For example, a user may press a button on one or more monitoring hubs to initiate a transfer request. In some implementations, a transfer request may comprise a non-contact or minimal-contact user input, such as a wireless communication signal, facial recognition, eye recognition, fingerprint recognition, gesture recognition, voice recognition, or the like. A transfer request can be received at a location and/or computing device that is remote to a monitoring hub. A transfer request may initiate transferring physiological monitoring.

In some implementations, identification data can include data generated and/or received via a monitoring hub when transferring physiological monitoring. Identification data can include data that is associated with a user and can be used to identify the user. Identification data can comprise a user ID. Identification data can include a tag, marker, serial number, bar code, QR code, facial recognition, fingerprint recognition, voice recognition, eye recognition, gesture recognition, or the like. Identification data may be unique to a user. Identification data may be unique to a group of users (and may be the same for individuals within the group). Identification data may be used to identify a group to which the user belongs. Identification data may comprise or indicate permissions associated with a user such as permission or authority to transfer physiological monitoring. Identification data can include a reason (e.g., provided by a requesting user) for requesting a transfer. A computing device, such as a monitoring hub, can receive identification data via one or more wireless communication protocols such as near field communication (NFC) or radio frequency identification (RFID). For example, a user may place a badge configured for wireless communication in proximity to a monitoring hub to be detected by the monitoring hub. A computing device, such as a monitoring hub, can receive identification data via manual user input at a monitoring hub. For example, a user may enter their identification data at the monitoring hub via a keyboard, user interface, touchscreen, or the like. A computing device, such as a monitoring hub, can receive identification data via one or more biological markers. For example, a user may scan their finger, eye, face, or speak as their identification data to be identified at the monitoring hub. Identification data can be linked or paired with a transfer request.

In some implementations, a transfer request status may indicate a status of a request to transfer physiological monitoring. A transfer request status can include an approved or not approved status. In some implementations, a transfer request may be approved if identification data from a first monitoring hub matches identification data from a second monitoring hub. A transfer request may be approved if a requesting user has appropriate permissions to perform the transfer. In some implementations, a transfer request may not be approved if identification data from a first monitoring hub does not match identification data from a second monitoring hub. A transfer request may not be approved if a requesting user does not have appropriate permissions to perform the transfer.

In some implementations, wireless communication configuration data can comprise data used to establish wireless communication between one or more computing devices. For example, a monitoring hub and sensor may implement wireless communication configuration data to communicate with each other via one or more wireless communication protocols. Wireless communication configuration data can include device addresses of one or more computing devices such as monitoring hubs and/or sensors. Wireless communication configuration data can include access codes such as one or more of Inquiry Access Codes (IAC), Device Access Codes (DAC), and Channel Access Codes (CAC). An access code can include and/or be derived from a device address. Wireless communication configuration data can include link keys. Wireless communication configuration data can include clock data such as frequencies at which computing devices will communicate (e.g., to transmit data). Wireless communication configuration data may also be referred to herein as wireless communication data or communication data or wireless configuration data or configuration data.

In some implementations, a device address can facilitate wireless communication between computing devices. A device address may be associated with a computing device. A device address may be unique to a computing device. A device address can comprise an IP address. A device address can comprise a MAC address. A device address can comprise a serial ID associated with a computing device. A device address can comprise a Bluetooth Address (BD_ADDR). A device address can comprise an LAP value. A device address, or derivation thereof, may form at least a portion of an access code.

In some implementations, a link key may facilitate wireless communication between computing devices. A link key can authenticate one or more computing devices with each other. A link key can encrypt data exchanged wirelessly between one or more computing devices. A link key can comprise a Long-Term Key (LTK).

In some implementations, physiological data can include data generated by one or more sensors. Physiological data can correspond to a subject. Physiological data can include raw data, partially processed data, and/or fully processed data. Physiological data can include physiological parameters. Physiological data can include data relating to heart rate, respiration rate, blood pressure, blood oxygen saturation, hemoglobin content, ECG, EEG, temperature, subject orientation, subject position, subject movement, as non-limiting examples. Physiological data can include historical physiological data. Historical physiological data can include physiological data generated by a sensor over a time frame preceding a present time. Historical physiological data can include data corresponding to a time frame of less than 24 hours, less than 12 hours, less than 1 hour, less than 30 minutes, less than 10 minutes, less than minutes, less than 2 minutes, less than 1 minute, less than 30 seconds, less than 15 seconds, less than 10 seconds, less than 5 seconds, or less than 1 second. Physiological data can include real-time physiological data. Real-time physiological data can include physiological data transmitted and/or received at a substantially similar time as the physiological data is generated by a sensor, for example, such that any difference in time may be imperceptible to human senses.

Example Systems

FIG. 1A is a schematic block diagram illustrating an example implementation of a physiological monitoring system (PMS) 150. The PMS 150 can include a monitoring hub 100A, a monitoring hub 100B, one or more sensors 102 (e.g., sensors 102A, 102B, 102C), a network 104, and one or more servers 106. In some implementations, the PMS 150 may include only two monitoring hubs (e.g., hubs 100A, 100B). In some implementations, the PMS 150 may include more than two monitoring hubs. In some implementations, the PMS 150 may include only one monitoring hub.

The monitoring hub 100A can communicate with the one or more sensors 102. In some implementations the monitoring hub 100A may communicate with the one or more sensors 102 via a wireless communication protocol such as WiFi, Bluetooth, near field communication (NFC), radio frequency identification (RFID), cellular, 1G, 2G, 3G, 4G, 5G, and/or Zigbee. In some implementations, the sensor(s) 102 may be a "slave" in a master-slave communication relationship such as a Bluetooth communication protocol with the monitoring hub 100A. In some implementations, the sensor(s) 102 may communicate with only one device at a time (e.g., a "master" device) such as a monitoring hub. The monitoring hub 100A may communicate data to the one or more sensors 102 and/or receive data from the one or more sensors 102. For example, the monitoring hub 100A may receive physiological data from the one or more sensors 102. As another example, the monitoring hub 100A may receive communication data (e.g., device addresses of the one or more sensors 102) from the one or more sensors 102 and/or communicate communication data (e.g., device addresses of the monitoring hubs 100A, 100B) to the one or more sensors 102. In the example implementation illustrated in FIG. 1A, monitoring hub 100B has not established direct wireless communication with the one or more sensors 102.

The monitoring hubs 100A, 100B can communicate with the server(s) 106 via a network 104. The network 104 can include any one or more communications networks, such as the Internet. The network 104 can include any combination of networks, such as a personal area network (PAN), a local area network (LAN), a metropolitan area network (MAN), a wide area network (WAN), or the like. Accordingly, various components of the PMS 150 can communicate with one another directly or indirectly via any appropriate communications links and/or networks, such as network 104 (e.g., one or more communications links, one or more computer networks, one or more wired or wireless connections, the Internet, any combination of the foregoing, and/or the like). Similarly, the various components (e.g., as described below) of the PMS 150 may, in various implementations, communicate with one another directly or indirectly via any appropriate communications links (e.g., one or more communications links, one or more computer networks, one or more wired or wireless connections, the Internet, any combination of the foregoing, and/or the like). The monitoring hubs 100A, 100B may, via the network 104, communicate data to the server(s) 106 and/or receive data from the server(s) 106 including communication data (e.g., device addresses and/or link keys corresponding to the sensors 102 and/or monitoring hubs 100), physiological data, identification data (user ID), transfer requests, request approval status, or the like. The monitoring hubs 100A, 100B may communicate with the server(s) 106 via any combination of wireless communication protocols including, for example, WiFi, Bluetooth, near field communication (NFC), radio frequency identification (RFID), cellular, 1G, 2G, 3G, 4G, 5G, and/or Zigbee. In some implementations, a monitoring hub 100 may communicate with the server(s) 106 via a different wireless communication protocol than which it communicates with the one or more sensors 102. For example, a monitoring hub 100 may communicate with the server(s) 106 via a first wireless communication protocol, such as WiFi, and may communicate with the one or more sensors 102 via a second wireless communication protocol, such as Bluetooth.

In some implementations, the sensors 102 may optionally communicate with the server(s) 106 via the network 104. For example, the sensors 102 may communicate physiological data to the server(s) 106 and/or receive communication data (e.g., device address of a monitoring hub) from the server(s) 106. In some implementations, the sensors 102 may not communicate directly with the server(s) 106. In some implementations, data may be transmitted from the sensor(s) 102 to the server(s) 106 via a monitoring hub 100, or vice versa.

In some implementations, the monitoring hub 100A may be portable or mobile. For example, the monitoring hub 100A may be sized, shaped, and/or include a housing or casing to facilitate carrying the monitoring hub 100A such as by hand. In some implementations, the monitoring hub 100A may be stationary or fixed in a location. For example, the monitoring hub 100A may be mounted to a wall. In some implementations, the monitoring hub 100B may include similar structural and/or operational features as monitoring hub 100A. The monitoring hub 100A may be referred to as an origin monitoring hub. The monitoring hub 100B may be referred to herein as a destination monitoring hub.

The one or more sensors 102 can include various types of sensors configured to collect physiological data of a subject. The one or more sensors 102 can attach or couple to different parts of a subject such as, but not limited to, arms, legs, torso, chest, head, neck, fingers, forehead, and the like. The one or more sensors 102 can collect patient physiological data including, but not limited to, data relating to heart rate, respiration rate, blood pressure, blood oxygen saturation, hemoglobin content, ECG, EEG, temperature, subject orientation, subject position, subject movement, as non-limiting examples, and the like. The one or more sensors 102 can transmit physiological data to the monitoring hub 100A, monitoring hub 100B, and/or to the server(s) 106 in real-time as the one or more sensors 102 collect the data. In some implementations, one or more sensors 102 can include processors that can fully or partially process the data obtained by the sensors 102.

The server(s) 106 may comprise one or more computing devices including one or more hardware processors. The server(s) 106 may comprise program instructions configured to cause the server(s) 106 to perform one or more operations when executed by the hardware processors. The server(s) 106 may include, and/or have access to (e.g., be in communication with) a database or storage component or storage system which can include any computer readable storage medium and/or device (or collection of data storage mediums and/or devices), including, but not limited to, one or more memory devices that store data, including without limitation, dynamic and/or static random access memory (RAM), programmable read-only memory (PROM), erasable programmable read-only memory (EPROM), electrically erasable programmable read-only memory (EEPROM), optical disks (e.g., CD-ROM, DVD-ROM, etc.), magnetic disks (e.g., hard disks, floppy disks, etc.), memory circuits (e.g., solid state drives, random-access memory (RAM), etc.), and/or the like. In some implementations, the server(s) 106 may include and/or be in communication with a hosted storage environment that includes a collection of physical data storage devices that may be remotely accessible and may be rapidly provisioned as needed (commonly referred to as "cloud" storage). Data stored in and/or accessible by the server(s) 106 can include physiological data including historical physiological data previously obtained by the one or more sensors 102 and/or communication data including, for example, link keys and/or device addresses associated with monitoring hubs, sensors, or the like.

In some implementations, the network 104 may comprise and/or be in communication with an electronic medical records (EMR). In some implementations, the server(s) 106 may comprise and/or be in communication with an EMR. In some implementations, the one or more of the monitoring hubs 100A, 100B may be in communication with an EMR. An EMR can comprise a propriety EMR. An EMR can comprise an EMR associated with a hospital. An EMR can store data including medical records.

FIG. 1B is a schematic block diagram illustrating an additional example implementation of the physiological monitoring system (PMS) 150. The example implementation shown in FIG. 1B may result from a request to transfer physiological monitoring from monitoring hub 100A to monitoring hub 100B. Transferring physiological monitoring from one monitoring hub to another monitoring hub is described in greater detail herein, for example, with respect to at least FIG. 4 and/or FIGS. 5A-5E. For example, as shown in the example implementation of FIG. 1A, the sensor(s) 102 may be in communication with the monitoring hub 100A and may not be in communication with the monitoring hub 100B. The PMS 150 can transfer physiological monitoring (e.g., in response to a user request) from the monitoring hub 100A to the monitoring hub 100B. As shown in FIG. 1B, after the PMS 150 has transferred the physiological monitoring from monitoring hub 100A to monitoring hub 100B, the sensor(s) 102 may be in communication with the monitoring hub 100B and may not be in communication with the monitoring hub 100A. The monitoring hub 100B can receive and/or display physiological data received from the sensor(s) 102 via the wireless communication connection (e.g., Bluetooth and/or other wireless communication protocol) established with the sensor(s) 102 as a result of the transfer.

The monitoring hubs 100A, 100B can receive a user input 108. The user input 108 can include identification data and/or a transfer request. The user input 108 can be a manual user input such as via a display of the monitoring hubs 100A, 100B or via one or more buttons of the monitoring hubs 100A, 100B. For example, a user may press a button of the monitoring hubs 100A, 100B to request a transfer. The user input 108 can include an electronic input such as an electronic signal generated in response to a wireless communication protocol. For example, a user may bring a communication device (e.g., user ID badge) in proximity to the monitoring hubs 100A, 100B to generate an electronic signal (e.g., via NFC and/or RFID) at the monitoring hubs 100A, 100B.

In some implementations, the monitoring hub 100A can optionally communicate with the monitoring hub 100B. In some implementations the monitoring hub 100A may communicate with the monitoring hub 100B via a wireless communication protocol such as WiFi, Bluetooth, near field communication (NFC), radio frequency identification (RFID), cellular, 1G, 2G, 3G, 4G, 5G, and/or Zigbee. The monitoring hub 100A may communicate data to the monitoring hub 100B and/or receive data from the monitoring hub 100B including communication data (e.g., device addresses of the sensors 102), physiological data, identification data (e.g., user ID), transfer requests, request approval status, or the like. In some implementations, the monitoring hub 100A may communicate with the monitoring hub 100B only while the PMS 150 is transferring the physiological monitoring from the monitoring hub 100A to the monitoring hub 100B. For example, in some implementations, the monitoring hub 100A may only communicate with the monitoring hub 100B until the transfer is complete, the monitoring hub 100B has established communication with the sensor(s) 102, or the like. In some implementations, the monitoring hub 100A may communicate with the monitoring hub 100B to facilitate the transfer (e.g., may transmit communication data to facilitate establishing communication between the monitoring hub 100B and the sensor(s) 102. In some implementations, the monitoring hub 100A may not communicate with the monitoring hub 100B.

Figure 1C:
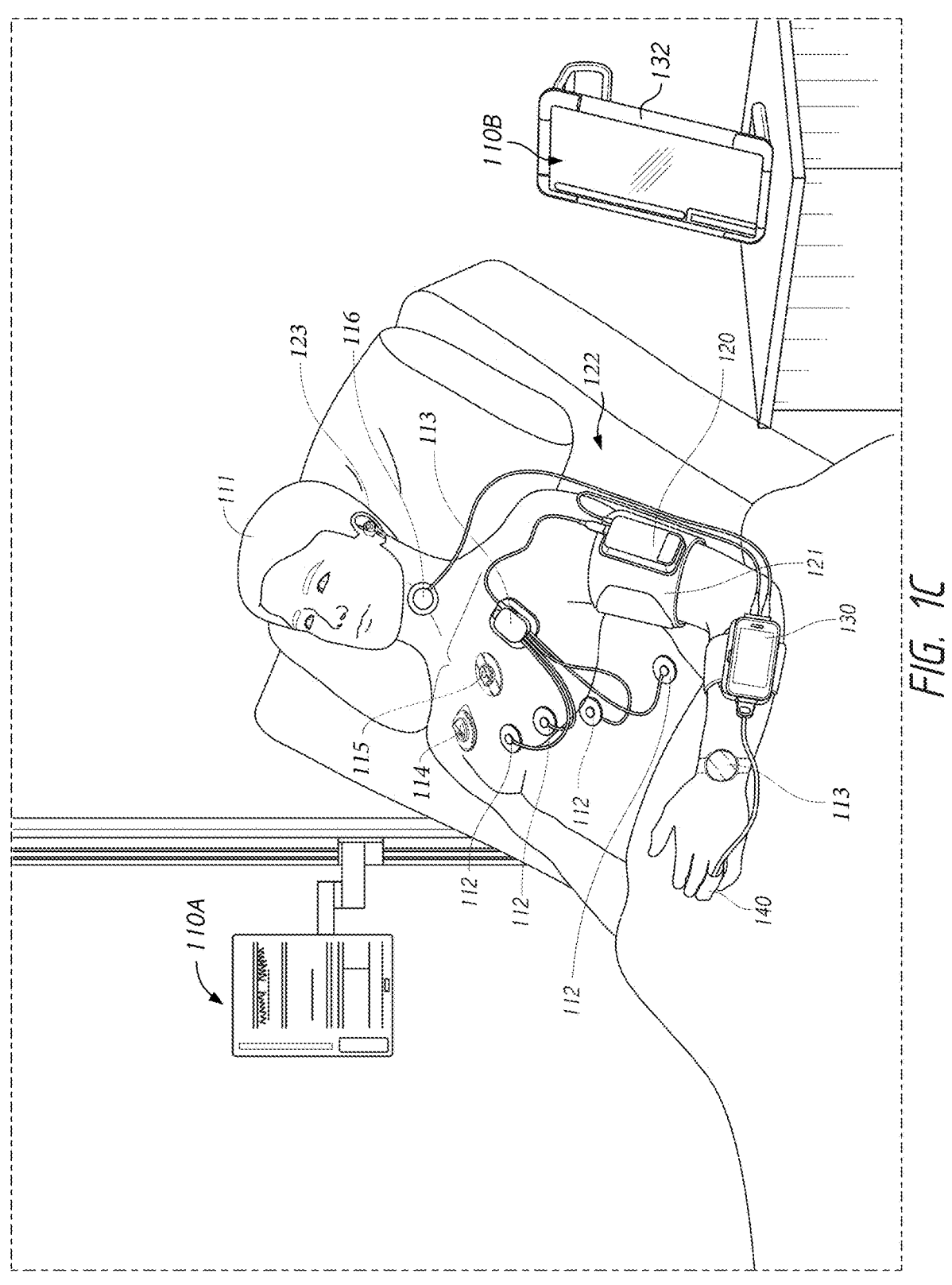
FIG. 1C illustrates an example implementation of a physiological monitoring system (PMS).

FIG. 1C illustrates an example implementation of a physiological monitoring system (PMS) including a monitoring hub 110A, a monitoring hub 110B, and one or more sensors 122. The PMS, or portions thereof, shown and discussed in FIG. 1C can include similar structural and/or operational features as the PMS 150, or portions thereof, shown and/or discussed in FIGS. 1A-1B. For example, the monitoring hub 110A can include similar structural and/or operational features as the monitoring hub 100A discussed in FIGS. 1A-1B. As another example, the monitoring hub 110B can include similar structural and/or operational features as the monitoring hub 100B discussed in FIGS. 1A-1B. As another example, the one or more sensors 122 can include similar structural and/or operational features as the sensor(s) 102 discussed in FIGS. 1A-1B.

As shown in this example implementation, the monitoring hub 110A is monitoring the physiological data of the subject 111 and the monitoring hub 110B is not monitoring the physiological data of the subject 111.

The one or more sensors 122 can be configured to obtain physiological data of the subject 111. The monitoring hub 110A is in electrical communication with the one or more sensors 122. In some implementations, the electrical communication between the monitoring hub 110A and the one or more sensors 122 may include a wireless communication protocol such as Bluetooth. The monitoring hub 110A receives physiological data from the one or more sensors 122 (e.g., in real-time as the data is generated by the one or more sensors 122). The monitoring hub 110A displays indicia of the physiological data and/or information relating thereto on a display of the monitoring hub 110A.

The monitoring hub 110B is not in electrical communication with the sensor 122. The monitoring hub 110B does not receive or display physiological data from the sensor 122. A user, such as a healthcare provider (e.g., doctor, nurse, etc.) may desire to transfer physiological monitoring from the monitoring hub 110A to the monitoring hub 110B. As described in greater detail herein, the user can transfer physiological monitoring from the monitoring hub 110A to the monitoring hub 110B such that the monitoring hub 110B would receive and display physiological data from the one or more sensors 122 and monitoring hub 110A would discontinue to receive and/or display physiological data from the one or more sensors 122. Subsequent to transferring physiological monitoring, the monitoring hub 110B could display indicia of physiological data previously displayed on the monitoring hub 110A. The monitoring hub 110B could display a user interface similar or identical, in whole or in part, to a user interface previously displayed by the monitoring hub 110A.

The one or more sensors 122 can include any number and/or type of sensors. The one or more sensors 122 can include an auricular device 123, such as an earbud, earpiece, or the like. The one or more sensors 122 can include an ECG device 113 which may include and/or be coupled to one or more ECG electrodes 112. The one or more sensors 122 can include a temperature sensor 114. The one or more sensors 122 can include a motion sensor 115 which can include one or more of a position sensor, motion sensor, gyroscope, accelerometers, or the like. The one or more sensors 122 can include an acoustic sensor 116. The one or more sensors 122 can include a wearable device 113, such as a smart device, which can comprise a watch. The wearable device 113 can include one or more sensors. The one or more sensors 122 can include an optical sensor 140 can comprise a finger sensor. The one or more sensors 122 can include a blood pressure monitor 121. The one or more sensors 122 can include a wearable hub 130. The wearable hub 130 may be coupled to one or more of the sensors shown and/or described herein. The wearable hub 130 may be in communication with one or more of the sensors shown and/or described herein. The wearable hub 130 may receive data from one or more of the sensors shown and/or described herein. In some implementations, the wearable hub 130 may be in communication with monitoring hub 110A and/or monitoring hub 110B. In some implementations, wearable hub 130 may collect sensor data from one or more sensors and communicate the sensor data to monitoring hub 110A and/or monitoring hub 110B. In some implementations, one or more of the sensors shown and/or described herein, may communicate directly with the monitoring hub 110A and/or monitoring hub 110B. For example, the wearable device 113, auricular device 123, optical sensor 140, ECG device 113, acoustic sensor 116, temperature sensor 114, motion sensor 115, blood pressure monitor 121 may communicate directly with the monitoring hub 110A and/or monitoring hub 110B, such as via wireless communication. In some implementations, the one or more sensors can include one or more of an infusion pump, a brain monitoring device, a depth of conscience device, or a pacemaker.

The monitoring hub 110A is shown as being in a fixed location (e.g., mounted to the wall). The monitoring hub 110A may be removably mounted to the wall. The monitoring hub 110B is shown as resting on a surface adjacent to the subject 111 and may be portable or mobile (e.g., not fixed to a particular location). The monitoring hub 110B is housed within a holder 132. The holder 132 is configured to support the monitoring hub in an upright position. In some implementations, the monitoring hub 110B may be fixed or removably fixed to a particular location. For example, the monitoring hub 110B may couple to a structure, such as a bed, by the holder 132. In some implementations, the monitoring hub 110A may be portable or mobile. In some implementations, the monitoring hub 110A may be housed within a holder similar or identical to the holder 132.

Figure 1D:
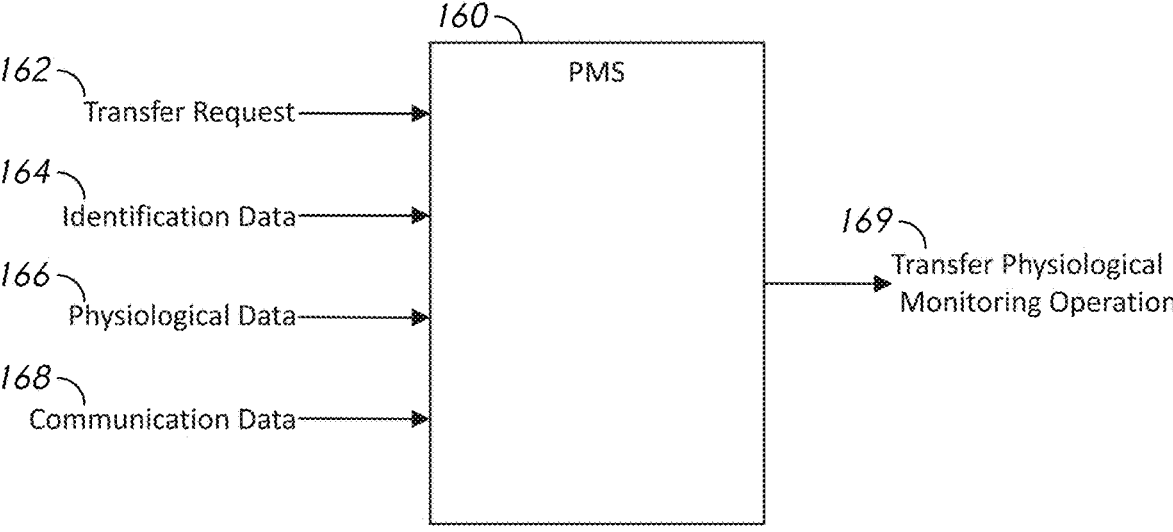
FIG. 1D is a schematic block diagram illustrating an implementation of an example physiological monitoring system (PMS).

FIG. 1D is a schematic block diagram illustrating an implementation of an example physiological monitoring system (PMS) 160. The PMS 160 may include similar features as other PMS discussed herein such as PMS 150 shown and/or discussed with respect to FIGS. 1A-1B. The operations, processes, functionality of the PMS 160 may be performed by one or more computing devices (e.g., hardware processor(s) of computing devices) such as any of the computing devices discussed herein, such as monitoring hub(s), sensor(s), and/or server(s), for example.

The PMS 160 can receive one or more inputs. The PMS 160 can receive a transfer request 162. The PMS 160 can receive the transfer request 162 via one or more monitoring hubs as described in greater detail elsewhere herein, such as shown and/or discussed with respect to FIG. 4, for example. The PMS 160 can receive identification data 164. The PMS can receive the identification data 164 via one or more monitoring hubs as described in greater detail elsewhere herein, such as shown and/or discussed with respect to FIG. 4, for example.

The PMS 160 can receive and/or access physiological data 166. The PMS 160 can receive the physiological data 166 from one or more physiological sensors. In some implementations, a monitoring hub of the PMS 160 can receive the physiological data 166 in real-time and/or directly from the one or more sensors. In some implementations, a server of the PMS 160 can receive the physiological data 166 in real-time and/or directly from the one or more sensors. In some implementations, a monitoring hub of the PMS 160 can transmit the physiological data 166 to a server of the PMS 160 after having received it from the sensors.

The PMS 160 can receive and/or access communication data 168. Communication data can include data to facilitate establishing communication between computing devices. Communication data can include device addresses of computing devices such as device addresses of monitoring hubs and/or physiological sensors, for example. The PMS 168 can access communication data 168 of a computing device from the computing device. The PMS can transmit communication data 168 between computing devices of the PMS 168 such as between monitoring hubs, sensors, and/or servers.

The PMS 160 can process the one or more inputs (e.g., inputs 162, 164, 166, 168) to generate an output. The PMS can process the inputs as described in greater detail elsewhere herein, such as shown and/or discussed with respect to FIGS. 5A-5E, for example. The PMS 160 can output a transfer physiological monitoring operation 169 in response to receiving and/or processing one or more inputs. The transfer physiological monitoring operation 169 can include transferring physiological monitoring from one monitoring hub of the PMS 160 to another monitoring hub of the PMS 160. The transfer physiological monitoring operation 169 may be described in greater detail elsewhere herein, such as shown and/or discussed with respect to FIGS. 5A-5E, for example.

Example Implementations

Figure 2:
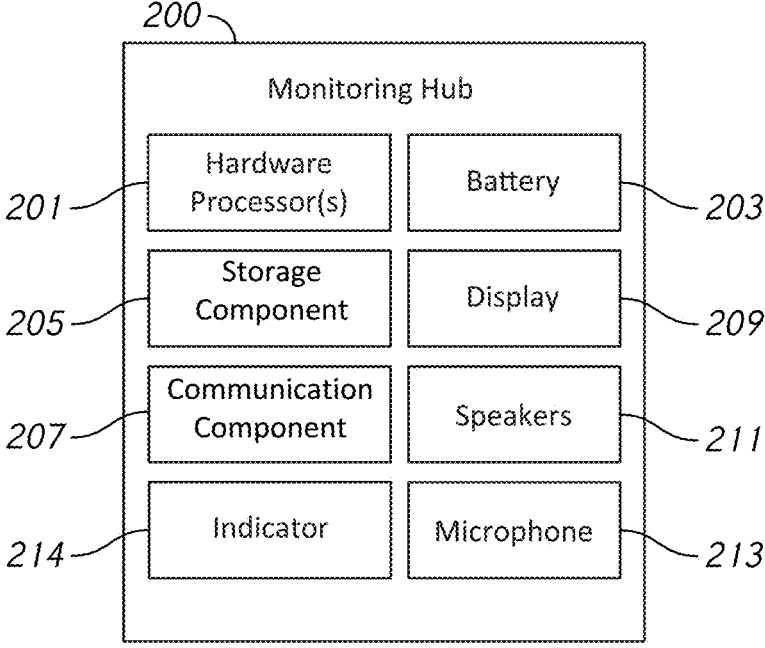
FIG. 2 is a block diagram illustrating an example implementation of a monitoring hub of a physiological monitoring system (PMS).

FIG. 2 is a block diagram illustrating an example implementation of a monitoring hub 200. The monitoring hub 200 can include similar structural and/or operational features as any of the other example monitoring hubs shown and/or discussed herein such as monitoring hubs 100A, 100B discussed in FIG. 1A.

As shown, the monitoring hub 200 can include a hardware processor 201, a storage component 205, a communication component 207, and a battery 203. The hardware processor 201 can be configured, among other things, to process data, execute program instructions to perform one or more functions, and/or control the operation of the monitoring hub 200. For example, the hardware processor 201 can process physiological data obtained from physiological sensors and can execute instructions to perform functions related to storing and/or transmitting such physiological data. As another example, the hardware processor 201 can process data relating to transfer requests, identification data, and/or transfer approval status.

The storage component 205 can include one or more memory devices that store data, including without limitation, dynamic and/or static random-access memory (RAM), programmable read-only memory (PROM), erasable programmable read-only memory (EPROM), electrically erasable programmable read-only memory (EEPROM), and the like. The storage component 205 can store data including processed and/or unprocessed physiological data obtained from physiological sensors. The storage component 205 can store data including communication data such as link keys and/or device addresses associated with sensors and/or monitoring hubs.

The communication component 207 can facilitate communication (via wired and/or wireless connection) between the monitoring hub 200 (and/or components thereof) and separate computing devices, such as separate monitoring hubs, monitoring devices, sensors, systems, servers, or the like. For example, the communication component 207 can be configured to allow the monitoring hub 200 to wirelessly communicate with other devices, systems, using any combination of a variety of communication protocols and/or over one or more networks. The communication component 207 can be configured to implement any combination of a variety of wireless communication protocols, such as Wi-Fi (802.11x), Bluetooth®, ZigBee®, Z-Wave®, cellular telephony, infrared, near-field communications (NFC), radio frequency identification (RFID), satellite transmission, proprietary protocols, combinations of the same, and the like. The communication component 207 can allow data and/or instructions to be transmitted and/or received to and/or from the monitoring hub 200 and separate computing devices. The communication component 207 can be configured to transmit and/or receive (for example, wirelessly) processed and/or unprocessed physiological data with separate computing devices including physiological sensors, other monitoring hubs, remote servers, or the like. As another example, the communication component 207 can be configured to transmit and/or receive (for example, wirelessly) communication data (e.g., link keys and/or device addresses associated with monitoring hubs and/or sensors) with separate computing devices including physiological sensors, other monitoring hubs, remote servers, or the like. The communication component 207 can be embodied in one or more components that may be in communication with each other. The communication component 207 can include one or more wireless transceivers, one or more antennas, one or more radios, and/or a near field communication (NFC) component such as a transponder. The communication component 207 can wirelessly communicate or connect to one or more remote computing devices over a network such as by implementing one or more wireless communication protocols.

The monitoring hub 200 can include a battery 203. The battery 203 can provide power for hardware components of the monitoring hub 200 described herein. The battery 203 can be, for example, a lithium battery. Additionally or alternatively, the monitoring hub 200 can be configured to obtain power from a power source that is external to the monitoring hub 200. For example, the monitoring hub 200 can include or can be configured to connect to a cable which can itself connect to an external power source to provide power to the monitoring hub 200.

The monitoring hub 200 can include a display 209. The display 209 can comprise an LED display. The display 209 can comprise a touchscreen, such as capacitive touchscreen. The display 209 can receive user input. The display 209 can render one or more user interfaces. The display 209 can display indicia of physiological data.

The monitoring hub 200 can include one or more speakers 211. The speakers 211 can emit an audio signal. The speakers 211 can emit an alarm. The speakers 211 can emit a voice audio signal. The speakers 211 can include a plurality of speakers positioned apart from one another at various positions on the monitoring hub 200. The speakers 211 can emit stereophonic audio. The speakers 211 can emit audio using one or more audio channels. The speakers 211 can emit audio in a plurality of directions. The speakers 211 can emit monaural audio. The speakers 211 can emit audio originating during a voice call and/or video call.

The monitoring hub 200 can include one or more microphones 213. The microphone 213 can detect audio signals and generate signals responsive to the detected audio signals. The microphone 213 can detect an ambient noise level. The microphone 213 can detect a noise level in an environment surrounding the monitoring hub 200. The microphone 213 can detect a noise level in an environment adjacent to and/or encompassing a subject. The monitoring hub 200 can adjust one or more operations based on at least an ambient noise level detected by the microphone 213. The monitoring hub 200 can perform one or more operations to increase a patient's comfort based on at least an ambient noise level detected by the microphone 213. The microphone 213 can detect the voice a person speaking. The microphone 213 can detect a person's voice during a voice call and/or during a video call.

The monitoring hub 200 can implement a voice call. The monitoring hub 200 can connect to one or more cellular devices. The monitoring hub 200 can implement a voice call using cellular telephony such as via the communication component 207. The monitoring hub 200 can implement a video call. A patient being monitored by the monitoring hub 200 can talk to another person in a remote location, such as a caregiver, via the monitoring hub 200 which can implement one or more wireless communication protocols, such as mobile telephony, to connect to one or more remote computing devices over a network, and which can detect the patient's voice using the microphone 213.

The monitoring hub 200 can include one or more indicators 214. The indicator 214 can include a visual indicator. The indicator 214 can include an LED indicator, comprising one or more LEDs. The indicator 214 can emit one or more visual signals. The visual signals may correspond to a physiological status of a patient being monitored by the monitoring hub 200. The indicator 214 can emit visual signals including a plurality of colors. The indicator 214 can emit visual signals according to a color-code scheme wherein various colors may correspond to various physiological statuses of a patient being monitored by the monitoring hub 200.

Figure 3A:
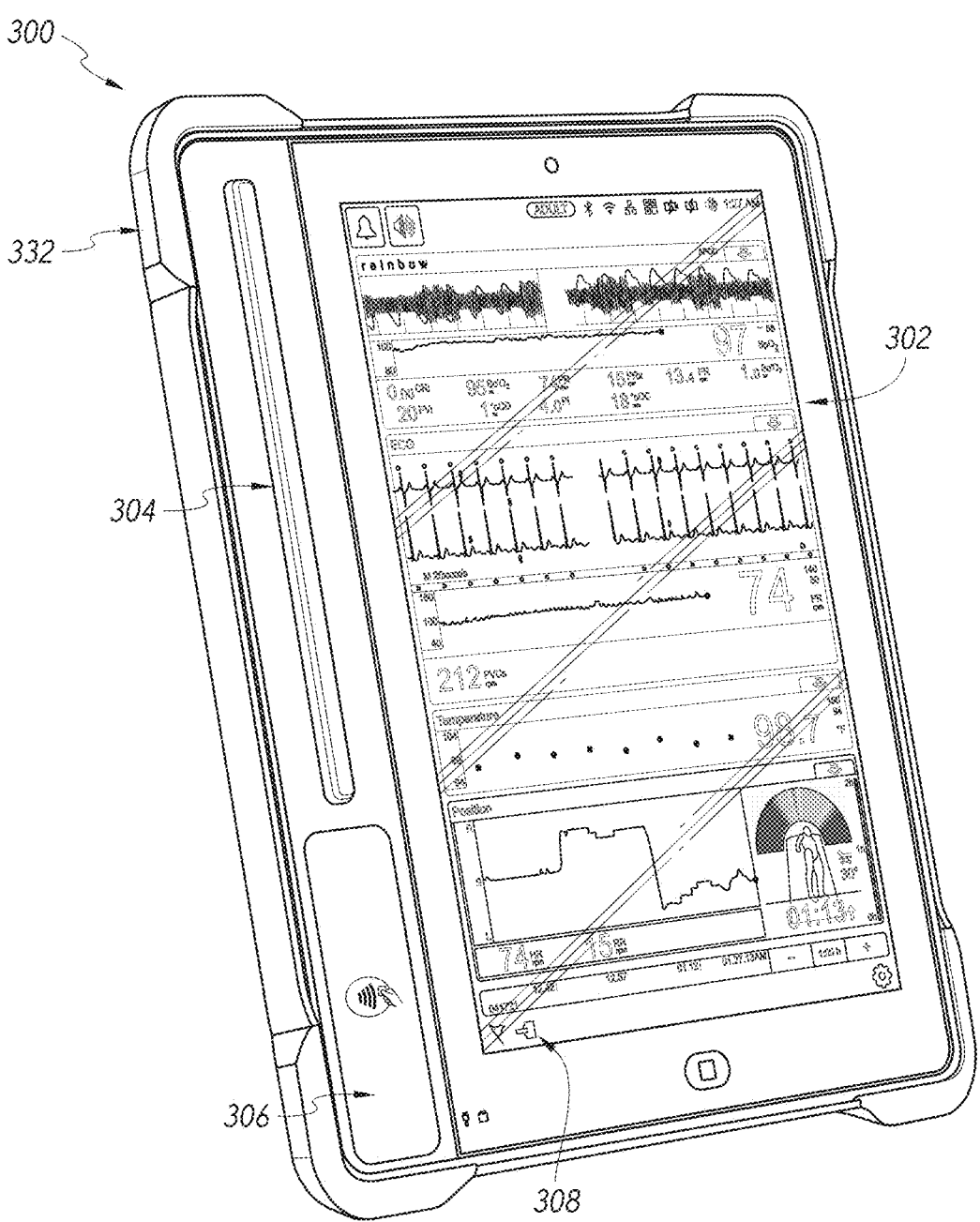
FIGS. 3A-3B are perspective views of example monitoring hubs.

FIG. 3A is a perspective view of an example monitoring hub 300. Monitoring hub 300 can include similar structural and/or operational features as any of the other example monitoring hubs shown and/or described herein. In this example implementation, the monitoring hub 300 is secured within a holder 332. The monitoring hub 300 may be removably secured within the holder 332, for example, via a friction fit. In this example implementation, the monitoring hub 300 can include a display 302. The display 302 can include an LED display. The display 302 can include a touchscreen configured to receive user input in response to touching the display 302. The display 302 can display indicia of physiological data, including physiological trends, graphs, graphics, charts, parameters, values, percentages, animations, visualizations, and the like. The display 302 can display indicia of physiological data from a plurality of sensors including different types of sensors that measure different types of physiological data. The monitoring hub can generate (and/or receive) user interface data for rendering the display indicia based on at least physiological data originating from one or more sensors or other devices.

The monitoring hub 300 can include a status indicator 304. The status indicator 304 can include one or more LEDs. The status indicator 304 can indicate a status of a subject being monitored by the monitoring hub 300. For example, the status indicator 304 may illuminate in response to a certain change in the physiological data of the subject, such as physiological parameter(s) of the subject, exceeding a threshold. The status indicator 304 may illuminate different colors during different operations or modes. The status indicator 304 may illuminate (e.g., red) during an alarm mode. The status indicator 304 may not illuminate when the monitoring hub 300 is not in alarm mode.

The monitoring hub 300 can include a communication interface 306. The communication interface 306 can include electronics configured to execute a wireless communication protocol. The communication interface 306 can include an NFC and/or RFID transponder or reader. The communication interface 306 can include a bar code reader or scanner. The communication interface 306 can include a QR code reader or scanner. The communication interface 306 can include a fingerprint scanner. The communication interface 306 can include a camera configured to capture images of a user's face for facial recognition. The communication interface 306 can use magnetic field induction to communicate with a separate device. The communication interface 306 can communicate with a user device such as a user ID badge, a user phone, a user mobile device, a user smartwatch, or the like, to identify and/or verify a user such as by receiving a unique user identification from the user device.

The monitoring hub 300 can include a transfer request button 308. The transfer request button 308 can include a capacitive sensor configured to generate one or more signals in response to a user's touch. The transfer request button 308 can include one or more physical or mechanical actuators configured to generate one or more signals in response a physical actuation of the button 308, such as depression of the button 308. A user may press the transfer request button 308 to initiate transfer of physiological monitoring to the monitoring hub 300 or from the monitoring hub 300. In some implementations, the transfer request button 308 can be incorporated into the display 302 (e.g., as part of a touchscreen display).

Figure 3B:
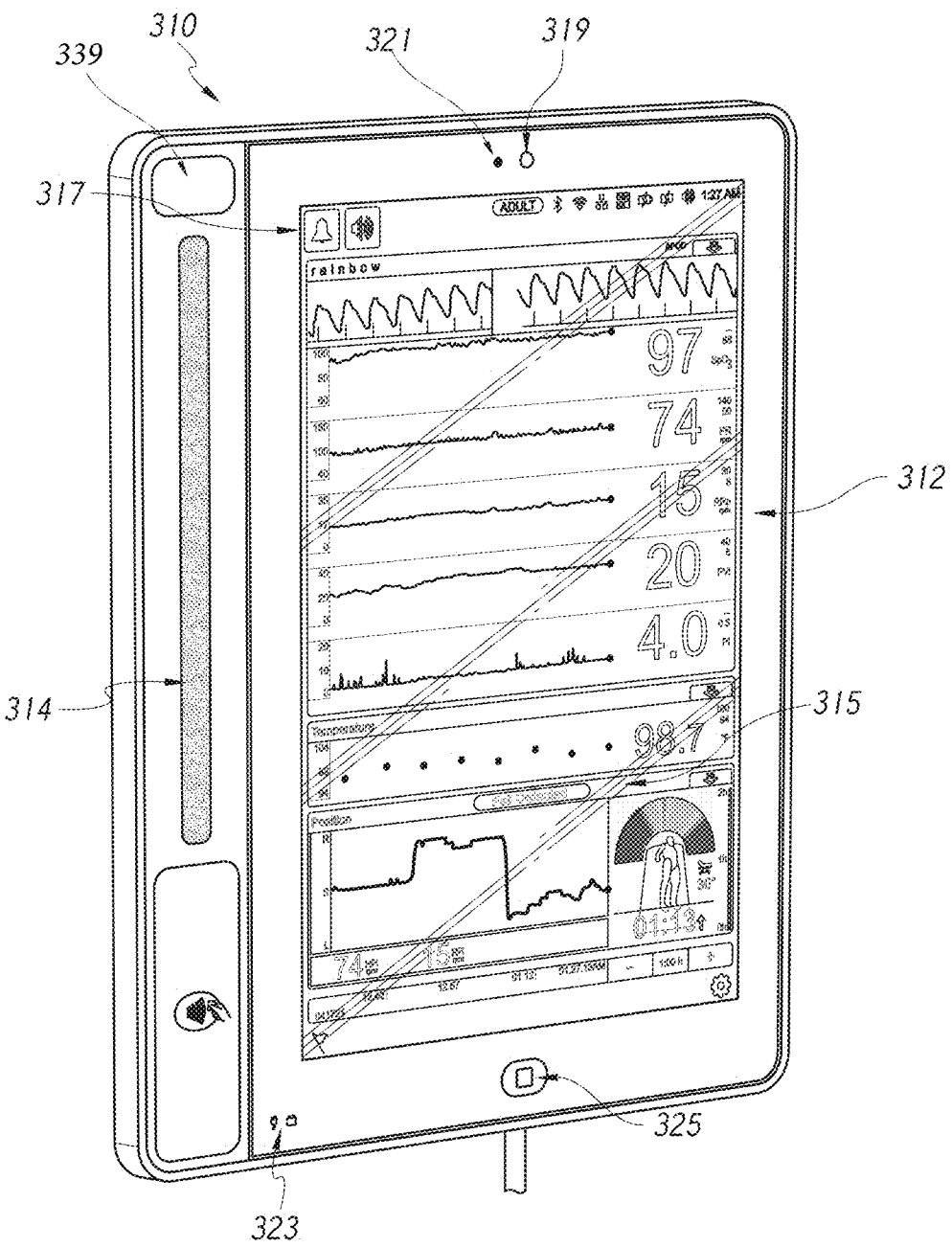

FIG. 3B is a perspective view of an example monitoring hub 310. Monitoring hub 310 can include similar structural and/or operational features as any of the other example monitoring hubs shown and/or described herein. Monitoring hub 310 can include a light sensor 319, a microphone 321, one or more indicators 323, a display 312, and/or a button 325. The light sensor 319 can be configured to detect an ambient light. The monitoring hub 310 may change a display brightness of the display 312 based on the ambient light detected by the light sensor 319. The microphone 312 can be configured to detect sound. In some implementations, the monitoring hub 310 may receive user input such as a transfer request as a voice command via a microphone 321. In some implementations, the monitoring hub 310 may implement voice recognition on sounds detected by the microphone 321. The indicator(s) 323 may include one or more LEDs. The indicator(s) 323 may indicate a status and/or operational state of the monitoring hub 310 such as power level, state of wireless connection, or the like. A user may operate the button 325 to control operation of the monitoring hub 310.

In this example implementation, the monitoring hub 310 is in alarm mode. During alarm mode, a status indicator 314 may illuminate (e.g., red). During alarm mode, a display 312 of the monitoring hub 310 may display one or more badges, icons, banners, symbols, indicators, or the like to indicate the monitoring hub 310 is in alarm mode. During this example alarm mode, the display 312 can include a "Fall Detected" banner 315. During this example alarm mode, the display 312 illuminates an alarm icon 317.

In some implementations, monitoring hub 310 can include an alarm toggle button 339. A user may press the alarm toggle button 339 to silence an alarm. A user may press the alarm toggle button 339 to change a state of an alarm. The alarm toggle button 339 can comprise a capacitive sensor. The alarm toggle button 339 can comprise one or more mechanical actuators.

Figure 4:
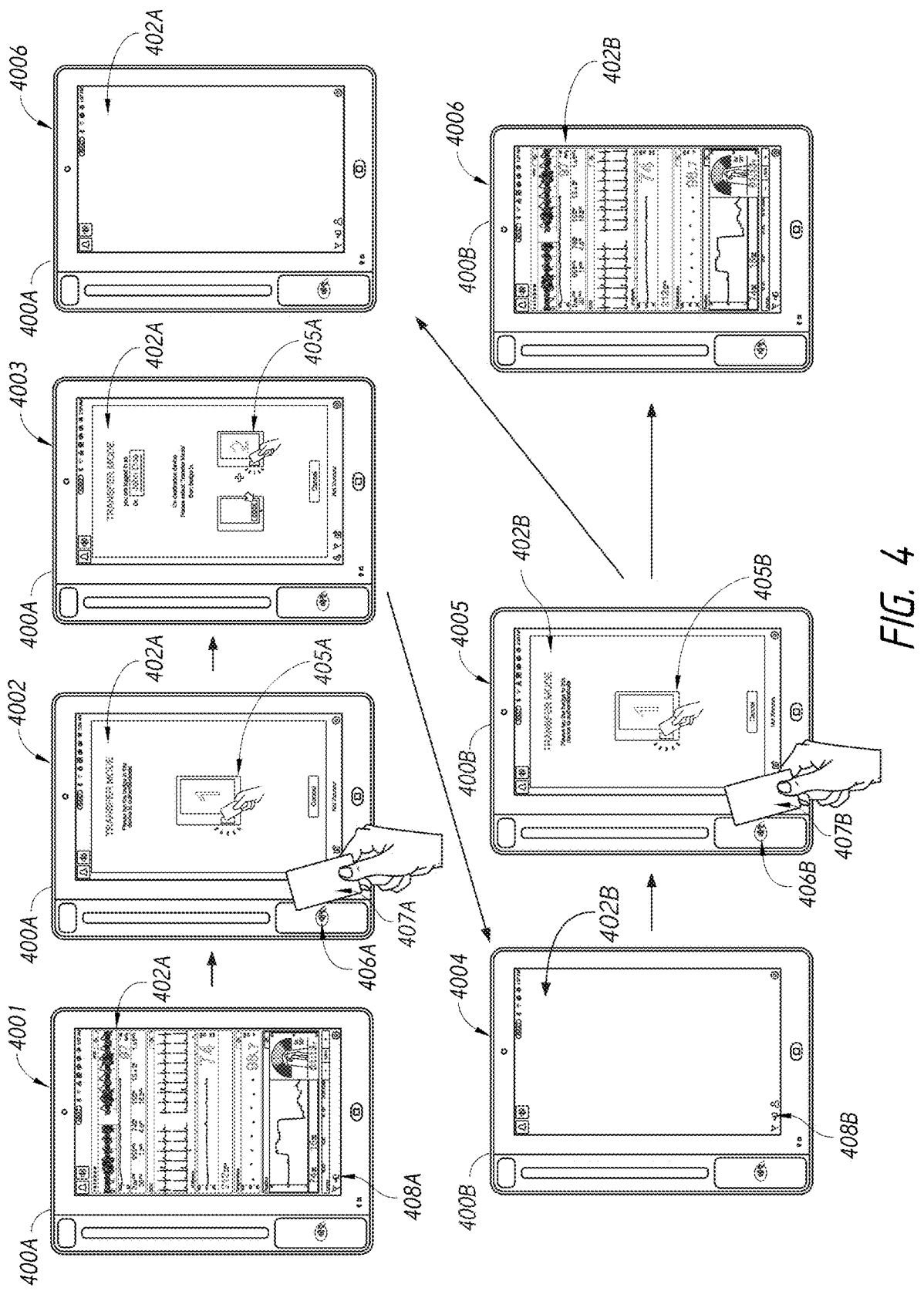
FIG. 4 illustrates an example process for transferring physiological monitoring from one monitoring hub to another monitoring hub.

FIG. 4 illustrates an example process for transferring physiological monitoring from one monitoring hub (e.g., origin hub) to another monitoring hub (e.g., destination hub)

within a physiological monitoring system (PMS). Advantageously, as described herein, a PMS can facilitate faster, simpler, and more efficient transfer of physiological monitoring from one monitoring hub to another monitoring hub. For example, a PMS provides an intuitive and easy-to-use system (e.g., user interfaces of monitoring hubs) for transferring physiological monitoring which can reduce time a health care provider must spend to oversee the subject's physiological monitoring and which can improve the quality of health care services provided to the subject. The process shown in FIG. 4 is provided as an example and is not intended to be limiting of the present disclosure. In some implementations, certain portions (e.g., steps) may be added, removed, and/or rearranged.

At step 4001, monitoring hub 400A (e.g., origin monitoring hub) monitors physiological data of a subject. For example, monitoring hub 400A can be in communication with one or more physiological sensors and receives physiological data therefrom. The monitoring hub 400A displays indicia of the physiological data on the display 402A. To initiate transferring monitoring from the monitoring hub 400A, a user can press the transfer request button 408A.

At step 4002, the display 402A may cease displaying physiological data and indicates that the monitoring hub 400A has entered a "transfer mode" operation. The display 402A can include instructions to the user to enter the identification data (e.g., "please tap the badge to this device to authenticate"). The display 402A can include graphical depictions 405A relating to the instructions and the actions to be taken by the user.

At step 4002, a user inputs identification data to the monitoring hub 400A. In this example, as shown, a user moves a user ID device 407A in proximity to the communication interface 406A. The communication interface 406A communicates with the user ID device 407A using a wireless communication protocol (e.g., NFC and/or RFID) to receive identification data from the user ID device 407A including an identification of the user. For example, the identification data can include a unique user ID (e.g., serial number, data sequence, etc.) associated with the user. In this example, the user ID device 407A can include a card or badge. In some implementations, the user ID device 407A can include a phone, a mobile device, a tablet, a smartwatch, or the like. In some implementations, the user may manually enter (e.g., via the display 402A) identification data, including an identification, in the monitoring hub 400A. In some implementations, the identification data may include one or more biomarkers of the user (e.g., facial recognition, fingerprint recognition, eye recognition, voice recognition) and the monitoring hub 400A may include one or more devices configured to receive and identify the biomarkers.

Figure 5A:
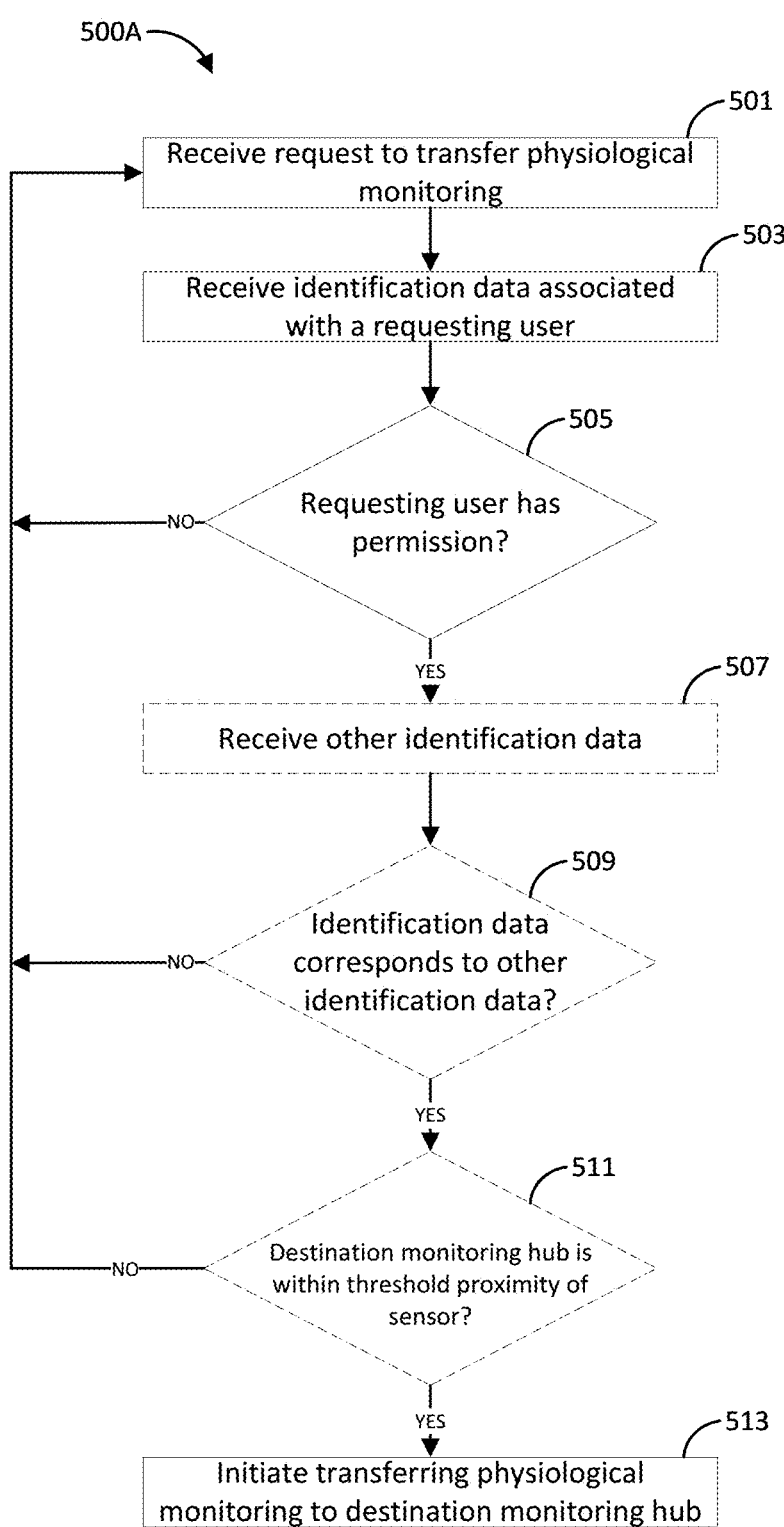

In some implementations, in response to receiving the identification data at the monitoring hub 400A, the PMS may determine whether the user has permission to perform the transfer, for example, as shown and/or discussed with respect to FIG. 5A. Receiving the identification data at step 4002 may cause the monitoring hub 400A to terminate a wireless communication connection, such as a Bluetooth connection, with one or more sensors. In some implementations, receiving the identification data at step 4002 may cause the monitoring hub 400B to establish a wireless communication connection, such as a Bluetooth connection, with one or more sensors.

At step 4003, the display 402A can indicate the identity of the user requesting the transfer (e.g., "you are logged in as Dr. John Doe."). The display 402A can indicate instructions to the user to request transfer to a second monitoring hub and to provide identification data at the second monitoring hub (e.g., "On destination device: please select 'Transfer Mode' then badge in."). The display 402A can include graphical depictions 405A relating to the instructions and the actions to be taken by the user.

At step 4004, monitoring hub 400B (e.g., destination monitoring hub) may not be monitoring physiological data of a subject. For example, monitoring hub 400B may not be in communication with one or more physiological sensors and may not receive physiological data therefrom. The monitoring hub 400B may not display physiological data on the display 402B. To initiate transferring monitoring to the monitoring hub 400B, a user can press the transfer request button 408B, for example, in response to the instructions provided on display 402A at step 4003.

At step 4005, the display 402B indicates that the monitoring hub 400B has entered a "transfer mode" operation. The display 402B can include instructions to the user to enter the identification data (e.g., "please tap the badge to this device to authenticate"). The display 402B can include graphical depictions 405B relating to the instructions and the actions to be taken by the user.

At step 4005, the user can input identification data to the monitoring hub 400B. For example, the user moves a user ID device 407B in proximity to the communication interface 406B such that the communication interface 406B communicates with the with the ID device 407B using a wireless communication protocol (e.g., NFC and/or RFID) to receive identification data from the user ID device 407B indicating an identification of the user. In some implementations, the user may input the identification data using other devices or processes as described herein. In some implementations, the user ID device 407B can be the same as the user ID device 407A.

In some implementations, in response to receiving the identification data at the monitoring hub 400B, the PMS may determine whether the user has permission to perform the transfer, for example, as shown and/or discussed with respect to FIG. 5A. Receiving the identification data at step 4005 may cause the monitoring hub 400A to terminate a wireless communication connection, such as a Bluetooth connection, with one or more sensors. Receiving the identification data at step 4005 may cause the monitoring hub 400B to establish a wireless communication connection, such as a Bluetooth connection, with one or more sensors. Receiving the identification data at step 4005 may cause the monitoring hub 400B to initiate a paging process to establish a Bluetooth connection with one or more sensors.

After receiving the identification data at the monitoring hub 400B, the PMS can determine whether the transfer request is approved. Determining that the transfer request is approved can include comparing the identification data received at the monitoring hub 400A with the identification data received at the monitoring hub 400B. Determining that the transfer request is approved can include comparing a user ID of the identification data received at the monitoring hub 400A with a user ID of the identification data received at the monitoring hub 400B. In some implementations, the PMS may determine that the transfer request is approved if the identification data received at the monitoring hub 400A matches the identification data received at the monitoring hub 400B. In some implementations, the PMS may determine that the transfer request is approved if the identification data received at the monitoring hub 400A corresponds to the identification data received at the monitoring hub 400B. Identification data may correspond without matching or being identical such as if identification data correspond to two users within a same group, assigned to a same task, assigned to a same patient, on a same schedule, or the like. For example, one user may input their identification data at an origin monitoring hub and another user may input their identification data at a destination monitoring hub if the two users are working together to care for a patient and the PMS may determine that the two identification data correspond (although they may not match identically). Additional details regarding determining transfer request approval are shown and/or discussed with respect to FIG. 5A.

In response to receiving the identification data and determining that the request to transfer is approved, the PMS can establish wireless communication, such as a Bluetooth connection, between the monitoring hub 400B and one or more of the physiological sensor(s) previously in communication with the monitoring hub 400A. Establishing a wireless communication can include initiating a paging process of a Bluetooth protocol. Establishing a wireless communication may not include a pairing process of a Bluetooth protocol. Additional details regarding establishing a communication between the monitoring hub 400B and the phycological sensors are shown and/or discussed with respect to FIGS. 5A-5E.

In some implementations, the PMS may establish a communication between the monitoring hub 400A and the monitoring hub 400B. Establishing communication between the monitoring hubs 400A and 400B can facilitate communication of information therebetween including, for example, communication data (e.g., device addresses of physiological sensors), physiological data (e.g., historical physiological data), or the like.

At step 4006, the monitoring hub 400A may discontinue displaying indicia of physiological data and/or other data via display 402A. The monitoring hub 400B may commence displaying indicia physiological data and/or other data via display 402B. In some implementations, the monitoring hub 400B may begin displaying data after the monitoring hub 400A has ceased displaying data. In some implementations, the monitoring hub 400B may begin displaying data before the monitoring hub 400A has ceased displaying data. In some implementations, the monitoring hub 400B may begin displaying data at a same time as the monitoring hub 400A ceases to display data.

At step 4006, the monitoring hub 400B can display physiological data via the display 402B. The physiological data displayed on display 402B can include real-time physiological data received from the sensors in communication with the monitoring hub 400B. The physiological data displayed on display 402B can include historical physiological data that was collected by the sensors at a time preceding establishing communication between the sensor(s) and the monitoring hub 400B. For example, the monitoring hub 400B may receive historical physiological data from the monitoring hub 400A and/or from a server of the PMS that was collected by the sensor(s) and/or received at the monitoring hub 400A prior to the monitoring hub 400B establishing communication with the sensor(s). Historical physiological data may not have been received at the monitoring hub 400A directly from the sensor(s). Advantageously, by displaying historical physiological data in combination with real-time physiological data (e.g., received from the sensor(s)), the monitoring hub 400B may display physiological data as if the monitoring hub 400B had been monitoring the physiological data (e.g., receiving data obtained from the sensor(s)) at a time preceding when the monitoring hub 400B began monitoring the physiological data. Advantageously, transferring monitoring from one hub to another, may not result in a loss of data or inability to view data because the destination monitoring hub (e.g., monitoring hub 400B) may display data prior to the transfer. A user may advantageously view physiological data after transferring monitoring from one monitoring hub to another with few or no discontinuities, breaks, losses in data, or the like. Advantageously, a PMS may be configured to continuously monitor the physiology of the subject while transferring physiological monitoring from one monitoring hub to another monitoring hub.

In some implementations, the PMS may transfer physiological monitoring as shown and/or described with reference to FIG. 4 without receiving a physical user input, such as a button press, at steps 4001 and/or 4004. For example, a user may not press a button, such as button 408A, on monitoring hub 400A to request a transfer. As another example, user may not press a button on monitoring hub 400B, such as button 408A, to place the monitoring hub 400B in a transfer mode. In some implementations, a user may request to transfer physiological monitoring by inputting identification data, such as via NFC/RFID, as described step 4002. In some implementations, a user may place monitoring hub 400B in transfer mode by inputting identification data, such as via NFC/RFID, as described step 4005. Accordingly, the devices and systems described herein may provide a method for transferring physiological monitoring by implementing non-contact user input. For example, a user may transfer physiological monitoring without physically contacting a monitoring hub such as to press a button. Other examples include transferring physiological monitoring without requiring the user to unplug or replug devices, turn devices on or off, or change a mode of operation of devices, such as to place a device in pairing mode, discovery mode, or connection mode. Reducing physical contact may improve sanitation, improve speed and efficiency of transferring physiological monitoring, and reduce complexities of transferring physiological monitoring such as by reducing the number of steps needed to transfer physiological monitoring. Non-contact input can comprise near field communication (NFC) and/or radio frequency identification (RFID). Non-contact input can comprise facial recognition, eye recognition, fingerprint recognition, gesture recognition, voice recognition, or the like. Non-contact input can comprise minimal-contact input. Moreover, the devices and systems described herein may provide a method for a user-controlled transfer of physiological monitoring. For example, a user may control when to transfer physiological monitoring, such as by providing user input to the system, which can include non-contact user input. Controlling transferring physiological monitoring by user input may reduce erroneous or undesirable transfers, which may occur as a result of devices being in proximity to one another, for example. In some implementations, the system may automatically transfer physiological monitoring without requiring user input, such as by implementing proximity-based wireless communication connections.

In some implementations, the PMS may transfer physiological monitoring as shown and/or described with reference to FIG. 4 between monitoring hubs and a plurality of sensors. The PMS may transfer wireless communication connections of a plurality of sensors at a single time. The PMS may transfer wireless communication connections of a plurality of sensors in response to a single user input. The PMS may transfer wireless communication connections of a plurality of sensors in response to a single request to transfer physiological monitoring. Advantageously, transferring physiological monitoring of a plurality of sensors at a single time may improve the speed and efficiency of transferring physiological monitoring such as by not having to implement a similar transfer procedure repeatedly for each sensor.

Example Methods

FIG. 5A is a flowchart illustrating an example process 500A of transferring physiological monitoring from an origin monitoring hub to a destination monitoring hub. One or more hardware processors can execute process 500A, or portions thereof. Process 500A, or portions thereof, can be implemented on one or more computing devices described herein, such as an origin monitoring hub, a destination monitoring hub, a server, etc. Process 500A, or portions thereof, may be executed by one or more hardware processors of a single computing device. Process 500A, or portions thereof, may be executed by one or more hardware processors of multiple computing devices such as computing devices that are remote to each other and/or in wireless communication with each other. In some implementations, one or more hardware processors associated with a server, such as server 106 shown and/or described herein, may execute process 500A, or portions thereof. Process 500A is provided as an example and is not intended to be limiting of the present disclosure. In some implementations, one or more hardware processors executing the process 500A may omit portions of the process 500A, may add additional operations, and/or may rearrange an order in which the operations of the process 500A are executed.

At block 501, one or more hardware processors can receive a request to transfer physiological monitoring from one monitoring hub (e.g., origin monitoring hub) to another monitoring hub (e.g., destination monitoring hub). In some implementations, the origin monitoring hub and/or the destination monitoring hub may receive the request to transfer, for example, as shown and/or described with respect to FIG. 4. The one or more hardware processors may receive the request via a user input at a monitoring hub. The user input can comprise pressing a button on the monitoring hub. In some implementations, the process 500 may not include block 501. For example, the computing device(s) may receive identification data as discussed at block 503 without receiving a request to transfer at block 501. In some implementations, the request to transfer physiological monitoring may comprise a request to establish initial physiological monitoring at a monitoring hub without terminating physiological monitoring at another monitoring hub such as if physiological monitoring is being established for the first time or if physiological monitoring has not occurred recently prior to the request.

At block 503, the one or more hardware processors can receive identification data. The identification data may be associated with a user requesting the transfer. The one or more hardware processors may receive the identification data via a monitoring hub such as an origin monitoring hub and/or a destination monitoring hub. The identification data may be associated with a monitoring hub at which it received. In some implementations, the origin monitoring hub may receive the identification data, for example, as shown and/or described with respect to FIG. 4. In some implementations, receiving the identification data may serve as receiving the request to transfer physiological monitoring described at block 501. For example, process 500A may not implement block 501 or may implement block 501 as part of block 503.

At decision block 505, the one or more hardware processors may determine whether the user requesting to transfer physiological monitoring has appropriate permission to perform the transfer. In some implementations, the one or more hardware processors may determine whether the requesting user has permission based on at least the identification data received at block 503.

In some implementations, the one or more hardware processors may determine whether the requesting user has appropriate permission based on one or more of an identification of the user, job title of the user, role of the user, task assigned to the user, or the like, which may be determined by the identification data. For example, a doctor (e.g., as identified by a user ID include in the identification data) may have permission to perform the transfer whereas a nurse may not. As another example, a certain type of doctor (e.g., cardiologist) may have permission to perform the transfer whereas another type of doctor (e.g., surgeon) may not. As another example, a healthcare provider assigned to a patient may have permission to perform the transfer whereas a healthcare provider not assigned to the patient may not.

In some implementations, the one or more hardware processors may determine whether the requesting user has appropriate permission based on a time of the request. For example, a user may not have permission to transfer physiological monitoring between monitoring hubs while a subject being monitored is undergoing surgery, or sleeping, or during a scheduled meal time, or the like. In some implementations, the one or more hardware processors may determine whether the requesting user has appropriate permission based on a reason provided by the user which may be inputted at a monitoring hub by the user (e.g., as part of identification data). In some implementations, the one or more hardware processors may determine whether the requesting user has appropriate permission based on a location of the subject being monitored and/or a location of monitoring hub. For example, a user may not have permission to transfer physiological monitoring from a monitoring hub that is stationed in a particular hospital room to a mobile monitoring hub if the subject is supposed to remain in the particular hospital room. As another example, a user may not have permission to transfer physiological monitoring from a mobile monitoring hub to a monitoring hub that is stationed in a particular hospital room (e.g., surgical operating room) if the subject is not supposed to be in the particular hospital room (e.g., the subject is not scheduled for surgery).

Advantageously, verifying permissions associated with a user can improve quality of health care such as by ensuring that a PMS only transfers physiological monitoring under appropriate circumstances which can ensure that a subject is receiving proper healthcare (e.g., a subject is not relocated to a different room in a hospital if not appropriate).

In response to determining that the requesting user has permission to perform the transfer, the one or more hardware processors may proceed to block 507. In response to determining that the requesting user does not have permission to perform the transfer, the one or more hardware processors may return to block 501.

At block 507, the one or more hardware processors can optionally receive other identification data. The other identification data may be associated with a user requesting the transfer. The one or more hardware processors may receive the other identification data via a monitoring hub such as an origin monitoring hub and/or a destination monitoring hub. The other identification data may be associated with a monitoring hub at which it received. In some implementations, the destination monitoring hub may receive the other identification data, for example, as shown and/or described with respect to FIG. 4.

At decision block 509, the one or more hardware processors can determine whether the identification corresponds to the other identification data. The one or more hardware processors may compare the identification data. For example, the one or more hardware processors may compare identification data received by an origin monitoring hub with identification data received by a destination monitoring hub. In some implementations, comparing identification data can include determining whether the identification data received at the origin monitoring hub corresponds with identification data received at the destination monitoring hub. In some implementations, comparing identification data can include determining whether the identification data received at the origin monitoring hub matches identification data received at the destination monitoring hub. In some implementations, comparing identification data can include comparing user identifications included in the identification data.

In some implementations, the one or more hardware processors may determine that identification data correspond if the identification data (or portions thereof) in each of the respective identification data match each other, such as if they are identical or substantially similar. This may indicate for example that the user requesting transfer at the origin monitoring hub is the same user requesting transfer at the destination monitoring hub. In some implementations, the one or more hardware processors may determine that identification data do not correspond if the identification data (or portions thereof) in each of the respective identification data do not match each other. This may indicate that the user requesting transfer at the origin monitoring hub is not the same user requesting transfer at the destination monitoring hub.

In some implementations, the one or more hardware processors may determine that identification data correspond if the respective identification are associated with each other. This may indicate that a user requesting transfer at the origin monitoring hub is associated with the user requesting transfer at the destination monitoring hub. For example, a user requesting transfer at an origin monitoring hub may be associated with a user requesting transfer at a destination monitoring hub if the users are working together (e.g., providing healthcare services at a same time to a patient being monitored by the PMS). In some implementations, the one or more hardware processors may determine that a first user's identification is associated with a second user's identification if the first and second users are within the same group, for example, healthcare providers in the same or a similar group and/or location (such as a floor or a care unit).

Advantageously, comparing the identification data (e.g., that they correspond) can improve fidelity of transferring physiological monitoring from one monitoring hub to a proper monitoring hub. For example, determining that identification data correspond to each other may ensure that the PMS transfers physiological monitoring to the correct monitoring hub rather than to an incorrect monitoring hub which may have identification data that does not correspond to the identification data received at the origin monitoring hub. Advantageously, verifying that identification data correspond can facilitate accurately transferring physiological monitoring between desired monitoring hubs in a PMS that includes numerous monitoring hubs and/or that includes numerous requests to transfer physiological monitoring between various monitoring hubs occurring at or near the same time. For example, by verifying that identification data of origin and destination monitoring hubs correspond, a PMS can accurately transfer physiological monitoring between appropriate pairs of monitoring hubs (e.g., between origin and destination monitoring hubs) at a same or similar time such as between monitoring hub pair A, between monitoring hub B, and between monitoring hub pair C, without incorrectly transferring physiological monitoring between the hubs of different pairs (e.g., from a hub in pair A to a hub in pair B).

In some implementations, in response to determining that the identification data correspond, the one or more hardware processors may proceed to block 511. In some implementations, in response to determining that the identification data do not correspond, the one or more hardware processors may return to block 501.

At decision block 511, the one or more hardware processors can optionally determine whether a destination monitoring hub is within a threshold proximity of a sensor. The one or more hardware processors may determine the proximity of a monitoring hub to a sensor based on at least a wireless signal strength between the monitoring hub and the sensor. In response to determining that the destination monitoring hub is within a threshold proximity of the sensor, the one or more hardware processors may proceed to block 513. In response to determining that the destination monitoring hub is not within a threshold proximity of the sensor, the one or more hardware processors may return to block 501.

At block 513, the one or more hardware processors can initiate transferring physiological monitoring to the destination monitoring hub. Transferring physiological monitoring can include establishing wireless communication between one or more sensors and a destination monitoring hub. Transferring physiological monitoring can include terminating wireless communication between one or more sensors and an origin monitoring hub. In some implementations, terminating communication with origin monitoring hub may precede establishing communication with destination monitoring hub. In some implementations, terminating the communication may occur automatically as a result of establishing the communication. Transferring physiological monitoring can include transferring physiological monitoring associated with all of the sensors in communication with the origin monitoring hub to the destination monitoring hub. Transferring physiological monitoring can include transferring physiological monitoring associated with less than all of the sensors in communication with the origin monitoring hub to the destination monitoring hub.

Advantageously, process 500A can provide a system for transferring physiological monitoring from one monitoring hub to another monitoring hub (e.g., establishing and/or terminating communication between monitoring hubs and sensors) without having to unplug, plug, and/or replug cables, wiring, etc. of the monitoring hubs and/or physiological sensors.

FIG. 5B is a flowchart illustrating an example process 500B associated with transferring physiological monitoring from an origin monitoring hub to a destination monitoring hub. One or more hardware processors can execute process 500B, or portions thereof. Process 500B, or portions thereof, can be implemented on one or more computing devices described herein, such as an origin monitoring hub, a destination monitoring hub, a server, etc. Process 500B, or portions thereof, may be executed by one or more hardware processors of a single computing device. Process 500B, or portions thereof, may be executed by one or more hardware processors of multiple computing devices such as computing devices that are remote to each other and/or in wireless communication with each other. In some implementations, one or more hardware processors associated with a server, such as server 106 shown and/or described herein, may execute process 500B, or portions thereof. Process 500B is provided as an example and is not intended to be limiting of the present disclosure. In some implementations, one or more hardware processors executing the process 500B may omit portions of the process 500B, may add additional operations, and/or may rearrange an order in which the operations of the process 500B are executed.

At block 521, one or more hardware processors can receive wireless configuration data from an origin monitoring hub. The one or more hardware processors can receive the wireless configuration data via wireless transmission including one or more wireless communication protocols. The one or more hardware processors can receive the wireless configuration data via WiFi. The wireless configuration data can facilitate wireless communication with one or more sensors. The wireless configuration data can be associated with one or more sensors. the wireless configuration data can include one or more device addresses. The wireless configuration data can include one or more link keys.

At block 523, the one or more hardware processors can receive physiological data from an origin monitoring hub. The physiological data can include physiological data received at the origin monitoring and originating from one or more sensors. The physiological data can include historical physiological data previously received at the monitoring hub during a time frame. The physiological data can include historical physiological data previously generated by the one or more sensors during a time frame. In some implementations, the physiological data include real-time physiological data. The real-time physiological data can include data generated by the one or more sensors and transmitted the origin monitoring hub at a substantially similar time as transmitted from the origin monitoring hub to the one or more hardware processors. In some implementations, the one or more hardware processors can receive the physiological data as a continuous stream of data from the origin monitoring hub as the origin monitoring hub receives the data from the one or more sensors. In some implementations, the one or more hardware processors can receive the physiological data in response to an event, such as in response to a request to transfer physiological monitoring. In some implementations, the one or more hardware processors can receive the physiological data as a packet of data. For example, the one or more hardware processors can receive a transmission of physiological data from the origin monitoring hub which can include physiological data originating from the one or more sensors during a time frame.

In some implementations, the one or more hardware processors may receive data associated with the physiological data. Data associated with the physiological data can include user interface data for rendering a user interface comprising display indicia of the physiological data. Data associated with the physiological data can include signals correspond to alarms or alerts generated in response to the physiological data. Data associated with the physiological data can include a status associated with the subject corresponding to the physiological data.

At block 525, the one or more hardware processors can store the wireless configuration data and/or the physiological data. The one or more hardware processors can store the data in memory. The one or more hardware processors can store the wireless configuration data as associated with one or more sensors. The one or more hardware processors can store the physiological data associated with a monitoring hub, as associated with one or more sensors, and/or as associated with a subject.

At block 527, the one or more hardware processors may receive a request to establish physiological monitoring at a destination monitoring hub. The request to establish physiological monitoring at the destination monitoring hub may be included as part of a request to transfer physiological monitoring from an origin monitoring hub to the destination monitoring hub. The request to establish physiological monitoring may indicate one or more sensors with which the destination monitoring hub is to establish wireless communication. The one or more hardware processors may receive the request via one or more monitoring hubs such as shown and/or described herein such as with reference to FIG. 4 and/or FIG. 5A. In some implementations, the one or more hardware processors may execute block 527 prior to executing block 521 and/or block 523. For example, the one or more hardware processors may execute block 521 and/or block 523 in response to receive the request at block 527.

At block 529, the one or more hardware processors can transmit the wireless configuration data to a destination monitoring hub. The one or more hardware processors can access the wireless configuration data to be transmitted from memory. The wireless configuration data may be associated with one or more sensors with which the destination monitoring hub is to establish wireless communication. For example, the wireless configuration data may include one or more device addresses associated with one or more sensors. The wireless configuration data may include one or more link keys associated with one or more sensors. In some implementations, the wireless configuration data may be associated with the destination monitoring hub. For example, the wireless configuration data may include one or more link keys associated with the destination monitoring hub. The one or more hardware processors can transmit the wireless configuration data via one or more wireless communication protocols. The one or more hardware processors can transmit the wireless configuration data via WiFi. Transmitting the wireless configuration data to the destination monitoring hub may cause the destination monitoring hub to establish wireless communication with one or more sensors associated with the wireless configuration data.

At block 531, the one or more hardware processors can transmit the physiological data to the destination monitoring hub. The physiological data can include physiological data previously generated by one or more sensors and/or previously received at the origin monitoring hub. The physiological data can include data that has become historical physiological data at the time of transmission at block 529. For example, the physiological data can include data that was generated by one or more sensors and communicated to an origin monitoring hub prior to receiving the request to establish physiological monitoring at the destination monitoring hub and/or prior to establishing physiological monitoring at the destination monitoring hub. Transmitting the physiological data to the destination monitoring hub may cause the destination monitoring hub to render a user interface including display indicia corresponding to the physiological data. The one or more hardware processors can transmit the physiological data as a single transmission and/or at a single time. The one or more hardware processors can transmit the physiological data as a packet of data. The one or more hardware processors can transmit physiological data corresponding to a time frame in which the physiological was generated by the one or more sensors and can transmit the physiological data corresponding to the time frame as a single transmission, data packet, and/or at a substantially same time.

In some implementations, the one or more hardware processors can transmit data associated with the physiological data. Data associated with the physiological data can include user interface data for rendering a user interface comprising display indicia of the physiological data. Data associated with the physiological data can include signals corresponding to alarms or alerts generated in response to the physiological data. Data associated with the physiological data can include a status associated with the subject corresponding to the physiological data. As an example, the one or more hardware processors can transmit a signal associated with an alarm, alert, status, etc. to the destination monitoring hub that may have been generated at the origin monitoring hub based on the physiological data. Accordingly, the destination monitoring hub can continue with a same alarm, alert, status, etc. that was occurring on the origin monitoring hub which can preserve a continuity of physiological monitoring.

The one or more hardware processors can transmit the physiological data via one or more wireless communication protocols. The one or more hardware processors can transmit the physiological data via WiFi.

Figure 5C:
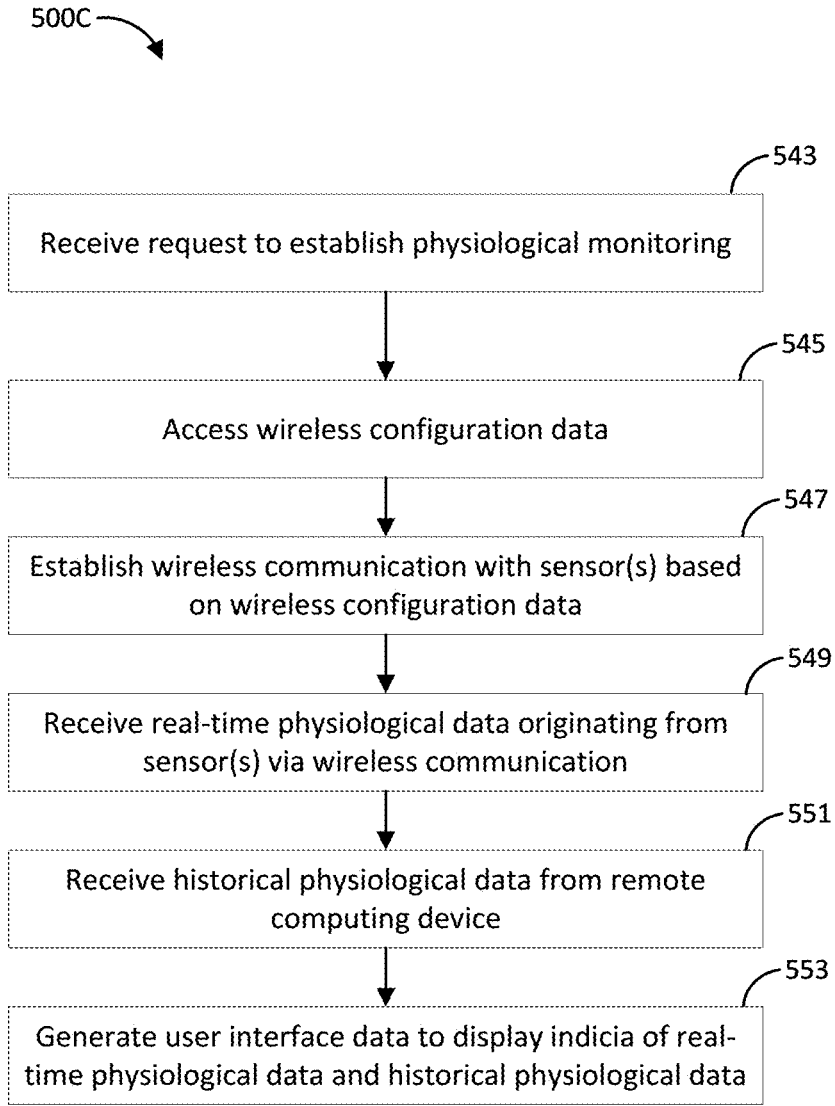

FIG. 5C is a flowchart illustrating an example process 500C associated with transferring physiological monitoring from an origin monitoring hub to a destination monitoring hub. One or more hardware processors can execute process 500C, or portions thereof. Process 500C, or portions thereof, can be implemented on one or more computing devices described herein, such as an origin monitoring hub, a destination monitoring hub, a server, etc. Process 500C, or portions thereof, may be executed by one or more hardware processors of a single computing device. Process 500C, or portions thereof, may be executed by one or more hardware processors of multiple computing devices such as computing devices that are remote to each other and/or in wireless communication with each other. In some implementations, one or more hardware processors associated with a destination monitoring hub may execute process 500C, or portions thereof. Process 500C is provided as an example and is not intended to be limiting of the present disclosure. In some implementations, one or more hardware processors executing the process 500C may omit portions of the process 500C, may add additional operations, and/or may rearrange an order in which the operations of the process 500C are executed.

At block 543, one or more hardware processors may receive a request to establish physiological monitoring at a destination monitoring hub. The request to establish physiological monitoring at the destination monitoring hub may be included as part of a request to transfer physiological monitoring from an origin monitoring hub to the destination monitoring hub. The request to establish physiological monitoring may indicate one or more sensors with which the destination monitoring hub is to establish wireless communication. The one or more hardware processors may receive the request via one or more monitoring hubs such as shown and/or described herein such as with reference to FIG. 4 and/or FIG. 5A. In some implementations, the one or more hardware processors may additionally verify a permission of a requesting user such as based on at least identification data.

At block 545, the one or more hardware processors can access wireless configuration data. The one or more hardware processors can access the wireless configuration data by receiving the wireless configuration data from a remote computing device such as a server. The one or more hardware processors can receive the wireless configuration data indirectly from the origin monitoring hub via an intermediary device. For example, the one or more hardware processors may receive the wireless configuration data from a server after server has received the wireless configuration data from the origin monitoring hub. The one or more hardware processors can access the wireless configuration data from memory. For example, the one or more hardware processors can access the wireless configuration data from memory stored on the destination monitoring hub. Wireless configuration data stored in memory may have been previously received from a remote computing device. In some implementations, the one or more hardware processors may receive the wireless configuration data from the origin monitoring hub via wired or wireless communication. In some implementations, the one or more hardware processors may not directly receive the wireless configuration data from the origin monitoring hub. In some implementations, the one or more hardware processors may receive the wireless configuration data from one or more sensors. In some implementations, the one or more hardware processors may generate at least a portion of the wireless configuration data. For example, the one or more hardware processors may generate and/or receive at least a portion of the wireless configuration data from one or more sensors during a pairing process with the one or more sensors. In some implementations, the one or more hardware processors may not generate and/or receive the wireless configuration data during a pairing process.

At block 547, the one or more hardware processors may establish wireless communication between the destination monitoring hub and one or more sensors. The one or more hardware processors can establish wireless communication according to one or more wireless communication protocols. The one or more hardware processors can establish wireless communication according to a Bluetooth communication protocol. Establishing wireless communication can comprise establishing a Bluetooth connection (e.g., subsequent to a paging process). The one or more hardware processors can establish wireless communication based on at least the wireless configuration data. The one or more hardware processors can establish wireless communication by initiating a paging process. The one or more hardware processors can establish wireless communication based on at least communicating at least a portion of the wireless configuration data to the one or more sensors. The one or more hardware processors can establish wireless communication without initiating a pairing process and/or an inquiry process. In some implementations, the destination monitoring hub may be considered as bonded to the one or more sensors such as by virtue of having access to the wireless configuration data. In some implementations, the destination monitoring hub may have never previously established wireless communication with the one or more sensors. Establishing communication can include establishing communication between the destination monitoring hub and all of the sensors previously in communication with the origin monitoring hub. Establishing communication can include establishing communication between the destination monitoring hub and less than all of the sensors previously in communication with the origin monitoring hub.

Advantageously, accessing the wireless configuration data at block 545, such as receiving the wireless configuration data from a remote computing device such as a server may facilitate establishing wireless communication such as by eliminating the need to perform a pairing process (which can include an inquiry process), which can take up to 10 seconds to complete and can involve non-trivial data processing and communication between remote devices.

Accordingly, accessing the wireless configuration data at block 545 may reduce processing requirements to establish a wireless communication at block 547, which can improve efficiency, reduce the time needed to establish a wireless communication, and reduce processing power required to establish wireless configuration data at block 545 which may improve energy conservation and prolong battery life. Moreover, reducing the time needed to establish wireless communication may reduce data loss. For example, data collected by a physiological sensor may be lost while waiting to establish wireless communication between the sensor and a monitoring hub (such as during a pairing process). Reducing data loss can improve physiological monitoring of the subject which can improve health care provided to the subject. Reducing data loss can improve continuous physiological monitoring of the subject while transferring physiological monitoring between monitoring hubs. For example, the monitoring hubs may continuously monitor the subject with a gap in data resulting during the transfer of less than 10 seconds, less than 5 seconds, less than 1 second, less than 0.5 seconds, less than 0.1 seconds, less than 0.05 seconds, less than 0.01 seconds, or the like. Moreover, eliminating the need to perform a pairing process (e.g., by accessing wireless configuration data at block 545) may avoid the need to place a sensor in a discovery mode, or may avoid the inability to establish wireless communication if the sensor is not in discovery mode. Advantageously, a user may be able to establish communication between sensors and a destination hub without having to turn off and/or turn on the sensors, the destination hub, and/or the origin hub. Advantageously, a user may be able to establish communication between sensors and a destination hub without having to change a connectivity state or mode of the sensors, the destination hub, and/or the origin hub.

The one or more hardware processors can establish a wireless communication at block 547 automatically, such as without requiring a user input. For example, the one or more hardware processors may establish wireless communication based on a proximity of the one or more sensors with the destination monitoring hub. The one or more hardware processors can establish a wireless communication at block 547 responsive to a user input. For example, a user may provide input to confirm the one or more hardware processors are to establish wireless communication. In some implementations, the user may provide non-contact user input to initiate establishing wireless communication. Non-contact user input can comprise near field communication (NFC) and/or radio frequency identification (RFID). Non-contact user input can comprise facial recognition, eye recognition, fingerprint recognition, gesture recognition, voice recognition, or the like. Non-contact user input can comprise minimal-contact user input, such as input that may not require contact but may nevertheless result in contact which can be minimal, unsubstantial, unintended, or inconsequential. Reducing physical contact may improve sanitation, improve speed and efficiency of transferring physiological monitoring, and reduce complexities of transferring physiological monitoring such as by reducing the number of steps needed to transfer physiological monitoring. In some implementations, the one or more hardware processors may establish wireless communication at block 547 based on a proximity of a destination monitoring hub to one or more sensors in combination with a user input.

The one or more hardware processors can establish a wireless communication at block 547 between a destination monitoring hub and a plurality of sensors. The one or more hardware processors can establish wireless communication with a plurality of sensors at a single time. The one or more hardware processors can establish wireless communication with a plurality of sensors in response to a single user input. The one or more hardware processors can establish wireless communication with a plurality of sensors in response to a single request to transfer physiological monitoring.

At block 549, the one or more hardware processors can receive real-time physiological data originating from one or more sensors. The one or more hardware processors can receive the real-time physiological data via the wireless communication established at block 547. The real-time physiological data can include data generated by the one or more sensors and transmitted to the one or more hardware processors in real-time. For example, the one or more hardware processors may receive the physiological data at a substantially same time as the one or more sensors generate the physiological data. As another example, the one or more hardware processors may receive the physiological data with a minimal time delay after the one or more sensors generate the physiological data which time delay may be imperceptible to humans. The one or more hardware processors may receive the real-time physiological data continuously. For example, the real-time physiological data may include a continuous stream of data. The one or more hardware processors may receive the real-time physiological data periodically. For example, the real-time physiological data may include data generated periodically by the one or more sensors.

At block 551, the one or more hardware processors can receive historical physiological data from a remote computing device, such as a server, such as server 106 shown and/or described herein. The one or more hardware processors can receive the historical physiological data via one or more wireless communication protocols such as WiFi. The historical physiological data can include physiological data previously generated by the one or more sensors. The historical physiological data can include data generated by the one or more sensors prior to establishing wireless communication between the destination monitoring hub and the one or more sensors at block 547. The historical physiological data can include data communicated from the one or more sensors to an origin monitoring hub, such as prior to establishing wireless communication between the destination monitoring hub and the one or more sensors at block 547. The historical physiological data can include data corresponding to a time frame of less than 6 hours, less than 1 hour, less than 30 minutes, less than 10 minutes, less than 5 minutes, less than 1 minute, less than 30 seconds, less than 10 seconds, or less than 1 second. The one or more hardware processors can receive the historical physiological data as a single transmission or packet of data. The one or more hardware processors can receive the historical physiological data at a single moment of time. The one or more hardware processors can receive the historical physiological data over a time frame that is shorter than the time frame corresponding to which the historical physiological data was generated by the one or more sensors. As an example, the one or more hardware processors can receive a packet of data comprising the historical physiological data as a single transmission and/or at a single moment of time.

In some implementations, the one or more hardware processors can receive data associated with the physiological data. Data associated with the physiological data can include user interface data for rending a user interface comprising display indicia of the physiological data. Data associated with the physiological data can include signals correspond to alarms or alerts generated in response to the physiological data. Data associated with the physiological data can include a status associated with the subject corresponding to the physiological data. As an example, the one or more hardware processors can receive a signal associated with an alarm, alert, status, etc. that may have been generated at the origin monitoring hub based on the physiological data. Accordingly, the destination monitoring hub can continue with a same alarm, alert, status, etc. that was occurring on the origin monitoring hub which can preserve a continuity of physiological monitoring. Moreover, the destination monitoring hub may be able to more rapidly initiate an alarm or alert or show a status at least because the destination monitoring hub may not have to re-process the historical physiological data to determine whether to initiate the alarm or alert or determine the status which may reduce processing time and energy requirement which may improve computational efficiencies as well as physiological healthcare monitoring. In one illustrative example, an origin monitoring hub may have generated an alarm corresponding to a critical patient condition based on at least analyzing physiological data received from sensors. Pursuant to transferring physiological monitoring to a destination monitoring hub, the destination monitoring hub may receive, such as from a server, a signal corresponding to the alarm. The destination monitoring hub may immediately initiate the alarm without having to process (historical) physiological data received from the origin monitoring hub, such as via the server. Accordingly, physiological monitoring of the patient may continue with reduced gaps or discontinuities.

In some implementations, the one or more hardware processors may analyze the historical physiological data received at block 551 to determine one or more physiological statuses or trends in physiological data. The one or more hardware processors may analyze the historical physiological data received at block 551 to generate one or more alarms, alerts, or the like, corresponding to the physiological data. Advantageously, because the one more hardware processors may have access to historical physiological data, such as received at block 551, the one or more hardware processors may be able to more accurately analyze physiological data at least because the one or more hardware processors may have access to more physiological data including historical physiological data and real-time physiological data.

At block 553, the one or more hardware processors can generate user interface data to render a display including indicia of physiological data which can include real-time physiological data and/or historical physiological data. The one or more hardware processors can render the display via the destination monitoring hub. The one or more hardware processors can transmit the user interface data to a remote computing device, such as smartwatch, smartphone, tablet, PC, wearable device, monitoring device which can render a display. Advantageously, the one or more hardware processors may have access to both real-time physiological data as well as historical physiological data (which may have been generated by the one or more sensors prior to establishing wireless communication with the one or more sensors) which may improve physiological monitoring such as by reducing data loss and providing a more comprehensive view of physiological data of a subject. The one or more hardware processors can generate user interface data to render a display that combines real-time physiological data in combination with historical physiological data with minimal or no breaks or discontinuities appearing in the display of the physiological data. The one or more hardware processors can generate user interface data to render a display as if the one or more hardware processors had been receiving physiological data from the sensor(s) at a time prior to establishing wireless communication at block 547.

In some implementations, at block 553, the one or more hardware processors may not generate user interface data corresponding to the historical physiological data. For example, at block 551, the one or more hardware processors may receive user interface data corresponding to the historical physiological data. User interface data received at block 551 may have been generated by an origin monitoring hub which may be similar or of a same type as a destination monitoring hub. Accordingly, user interface data generated by an origin monitoring hub and received at a destination monitoring hub may be compatible with the destination monitoring hub such that the destination monitoring hub may not need to re-generate user interface data for rendering a display corresponding to the historical physiological data. Advantageously, eliminating the need to generate redundant user interface data can reduce processing requirements, improve processing speed and efficiency, and reduce the time needed to render a display including indicia of physiological data which may improve physiological monitoring and healthcare provided to a subject. In some implementations, an origin monitoring hub and a destination monitoring hub may be different types and/or comprise non-similar displays such that user interface data generated at an origin monitoring hub may not be compatible with a destination monitoring hub. In such implementations, a destination monitoring hub can generate user interface data corresponding to historical physiological data as described at block 553.

Figure 5D:
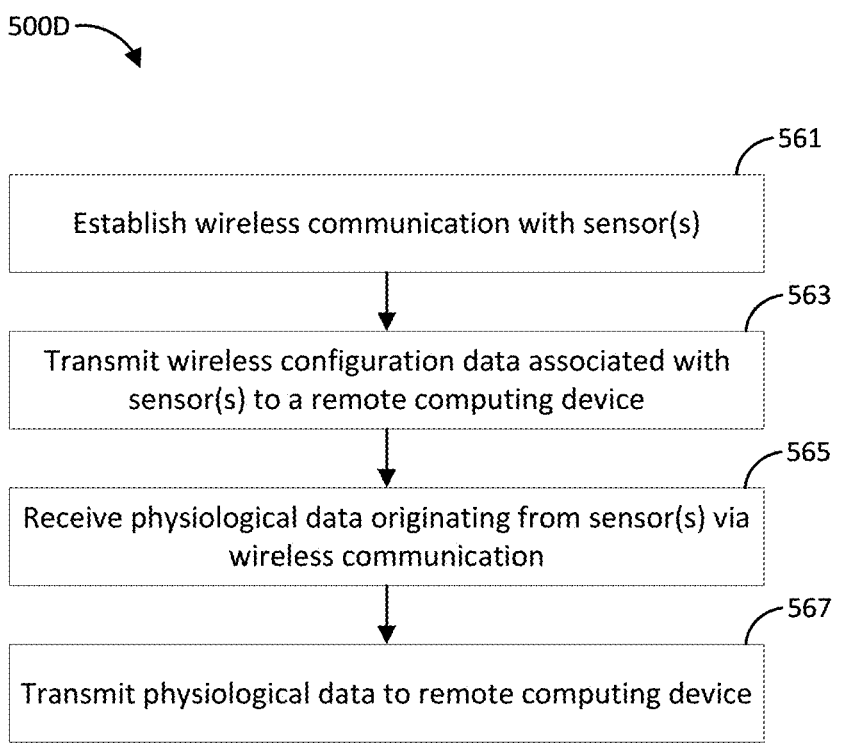

FIG. 5D is a flowchart illustrating an example process 500D associated with transferring physiological monitoring from an origin monitoring hub to a destination monitoring hub. One or more hardware processors can execute process 500D, or portions thereof. Process 500D, or portions thereof, can be implemented on one or more computing devices described herein, such as an origin monitoring hub, a destination monitoring hub, a server, etc. Process 500D, or portions thereof, may be executed by one or more hardware processors of a single computing device. Process 500D, or portions thereof, may be executed by one or more hardware processors of multiple computing devices such as computing devices that are remote to each other and/or in wireless communication with each other. In some implementations, one or more hardware processors associated with an origin monitoring hub may execute process 500D, or portions thereof. Process 500D is provided as an example and is not intended to be limiting of the present disclosure. In some implementations, one or more hardware processors executing the process 500D may omit portions of the process 500D, may add additional operations, and/or may rearrange an order in which the operations of the process 500D are executed.

At block 561, one or more hardware processors may establish wireless communication between a monitoring hub, such as an origin monitoring hub, and one or more sensors. The wireless communication can include one or more wireless communication protocols including Bluetooth.

At block 563, the one or more hardware processors can transmit wireless configuration data associated with the one or more sensors to a remote computing device. The one or more hardware processors may transmit the wireless configuration data to a server, such as server 106 shown and/or described herein. The wireless configuration data can include data used to establish the wireless communication at block 561. The wireless configuration data can include device addresses associated with the one or more sensors. The wireless configuration data can include link keys associated with the one or more sensors. The one or more hardware processors can transmit the wireless configuration data via one or more wireless communication protocols such as WiFi. In some implementations, the one or more hardware processors may communicate wireless configuration data to the one or more sensors. For example, the one or more hardware processors may wirelessly transmit wireless configuration data associated with a destination monitoring hub to the one or more sensors. In some implementations, the one or more hardware processors may transmit the wireless configuration data in response to a request to transfer physiological monitoring. In some implementations, the one or more hardware processors may transmit the wireless configuration data automatically such as upon generation and/or receipt of the wireless configuration data from the one or more sensors.

At block 565, the one or more hardware processors can receive physiological data originating from the one or more sensors. The one or more hardware processors can receive the physiological data via wireless communication such as Bluetooth.

At block 567, the one or more hardware processors can transmit physiological data to a remote computing device. The one or more hardware processors may transmit the physiological data to a server, such as server 106 shown and/or described herein. The one or more hardware processors can transmit the physiological data via one or more wireless communication protocols such as WiFi. In some implementations, the one or more hardware processors may transmit the physiological data in response to an event, such as a request to transfer physiological monitoring. In some implementations, the one or more hardware processors may transmit the physiological data automatically such as upon receipt of the physiological data from the one or more sensors. The one or more hardware processors may transmit the physiological data continuously. The one or more hardware processors may transmit the physiological data periodically. The one or more hardware processors can transmit physiological data originating from the one or more sensors during a time frame as a single transmission.

In some implementations, the one or more hardware processors can transmit data associated with the physiological data. Data associated with the physiological data can include user interface data for rending a user interface comprising display indicia of the physiological data. Data associated with the physiological data can include signals correspond to alarms or alerts generated in response to the physiological data. Data associated with the physiological data can include a status associated with the subject corresponding to the physiological data.

Figure 5E:
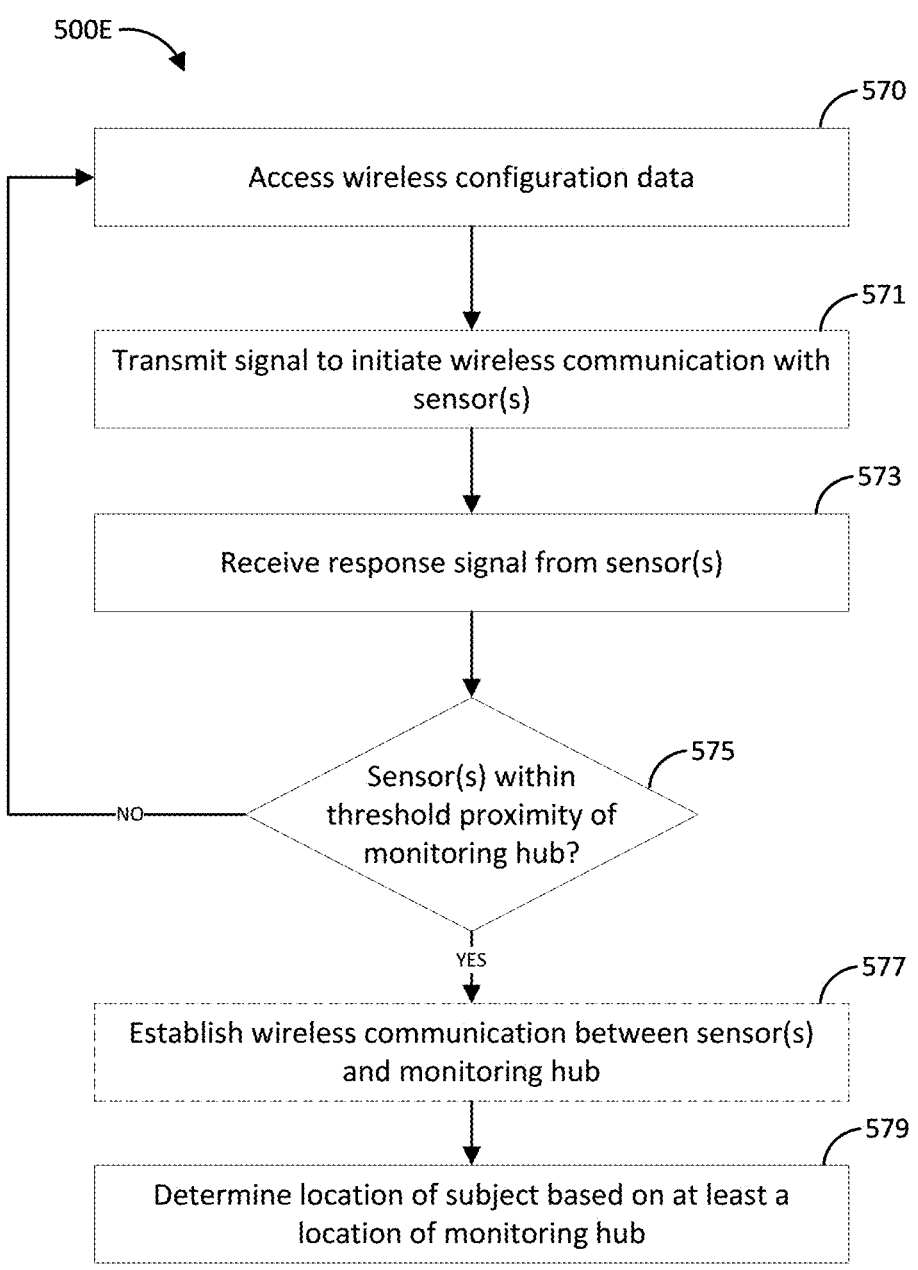
FIG. 5E is a flowchart illustrating an example process of monitoring a location of a subject.

FIG. 5E is a flowchart illustrating an example process 500E associated with monitoring a location of a subject. One or more hardware processors can execute process 500E, or portions thereof. Process 500E, or portions thereof, can be implemented on one or more computing devices described herein, such as an origin monitoring hub, a destination monitoring hub, a server, etc. Process 500E, or portions thereof, may be executed by one or more hardware processors of a single computing device. Process 500E, or portions thereof, may be executed by one or more hardware processors of multiple computing devices such as computing devices that are remote to each other and/or in wireless communication with each other. In some implementations, one or more hardware processors associated with a monitoring hub may execute process 500E, or portions thereof.

Process 500E is provided as an example and is not intended to be limiting of the present disclosure. In some implementations, one or more hardware processors executing the process 500E may omit portions of the process 500E, may add additional operations, and/or may rearrange an order in which the operations of the process 500E are executed.

Process 500E can facilitate monitoring a location of a subject. One or more sensors may be coupled to the subject. For example, the subject may don one or more sensors comprised as one or more wearable devices. Accordingly, a location of the one or more sensors may indicate a location of the subject. Devices and systems can monitor the location of the subject by determining the location of the one or more sensors. An environment, such as a hospital may comprise one or more monitoring dispersed at various locations throughout the environment. As a subject moves about the environment while wearing one or more sensors, the one or more monitoring hubs within the environment can detect the presence of the sensors using one or more wireless communication protocols such as Bluetooth. The monitoring hubs may determine a proximity of the one or more sensors to the monitoring hub, such as based on signal strength of a wireless signal. In some implementations, the monitoring hubs within the environment may establish wireless communication with the one or more sensors worn by the subject. The monitoring hubs may establish wireless communication based on a proximity of the one or more sensors to the monitoring hubs. For example, a monitoring hub that is closest to the one or more sensors may establish wireless communication with the one or more sensors rather than a monitoring hub that is further from the one or more sensors. Accordingly, as a subject wearing one or more sensors moves about an environment, one or more monitoring hubs within the environment may automatically terminate and establish wireless communication with the one or more sensors based on their proximity to the one or more sensors. Accordingly, systems and devices may monitor a location of the subject based on at least a proximity of one or more sensors worn by the subject to monitoring hubs and/or whether the one or more sensors are in wireless communication with the monitoring hubs.

At block 570, one or more hardware processors can access wireless configuration data. The one or more hardware processors can access the wireless configuration data by receiving the wireless configuration data from a remote computing device such as a server. The one or more hardware processors can access the wireless configuration data from memory. For example, the one or more hardware processors can access the wireless configuration data from memory stored on a monitoring hub. Wireless configuration data stored in memory may have been previously received from a remote computing device. In some implementations, the one or more hardware processors may receive the wireless configuration data from another monitoring hub via wired or wireless communication. In some implementations, the one or more hardware processors may receive the wireless configuration data from one or more sensors. In some implementations, the one or more hardware processors may generate at least a portion of the wireless configuration data. For example, the one or more hardware processors may generate and/or receive at least a portion of the wireless configuration data from one or more sensors during a pairing process with the one or more sensors. In some implementations, the one or more hardware processors may not generate and/or receive the wireless configuration data during a pairing process.

At block 571, the one or more hardware processors can transmit a signal to initiate wireless communication between a monitoring hub and one or more sensors. The one or more processors can transmit the signal according to a wireless communication protocol such as Bluetooth. The signal may be based on at least the wireless configuration data received at block 570. For example, the signal can comprise a device access code which can be based on a device address of the wireless configuration data. The device address can be associated with one or more of the one or more sensors. The signal may correspond to a paging process of a Bluetooth protocol. In some implementations, the signal may correspond to a pairing process of a Bluetooth protocol. For example, the signal may comprise an inquiry access code corresponding to an inquiry process. In some implementations, the signal may not correspond to a pairing process.

At block 573, the one or more hardware processors may receive a response signal from the one or more sensors. The one or more processors can receive the response signal according to a wireless communication protocol such as Bluetooth. The response signal may correspond to a paging process of a Bluetooth protocol. In some implementations, the response signal may correspond to a pairing process of a Bluetooth protocol, such as an inquiry process. In some implementations, the response signal may not correspond to a pairing process.

Advantageously, the one or more hardware processors may discover the existence of one or more sensors within a proximity of the one or more sensors based on at least sending and receiving signals according to blocks 571 and 573.

Advantageously, accessing the wireless configuration data at block 570, such as receiving the wireless configuration data from a remote computing device such as a server may facilitate discovering the existence and/or proximities of the one or more sensors such as by allowing the one or more hardware processors to implement a paging process to discover the existence of the one or more sensors. Accordingly, because the one or more hardware processors may have access to the wireless configuration data, the one or more hardware processors may not need to implement a pairing process to discover the existence of the one or more sensors. A pairing process may take longer than a paging process, may consume more energy, may require more hardware processing, and may require the one or more sensors to be discoverable in a discovery mode. Accordingly, by accessing the wireless configuration data, the one or more hardware processors may discover the existence and/or proximities of the one or more sensors in a shorter amount of time, using less energy and hardware processing, and may do so regardless of whether the one or more sensors are set to be discoverable in a discovery mode.

At decision block 575, the one or more hardware processors can determine whether the one or more sensors are within a threshold proximity of the monitoring hub. The one or more hardware processors can determine the proximity of the one or more sensors to the monitoring hub based on at least a signal strength associated with the one or more sensors, such as a signal strength of the response signal received at block 573. A stronger signal strength may correspond to closer proximity. A weaker signal strength may correspond to further proximity. In response to determining that the one or more sensors are within a threshold proximity, the one or more hardware processors may proceed to block 577. In response to determining that the one or more sensors are not within the threshold proximity, the one or more hardware processors may return to block 570.

At block 577, the one or more hardware processors can optionally establish wireless communication with the one or more sensors. The one or more hardware processors can establish wireless communication according to one or more wireless communication protocols. The one or more hardware processors can establish wireless communication according to a Bluetooth communication protocol. Establishing wireless communication can comprise establishing a Bluetooth connection (e.g., subsequent to a paging process). The one or more hardware processors can establish wireless communication based on at least the wireless configuration data. The one or more hardware processors can establish wireless communication based on at least sending a signal at block 571 and receiving a response signal at block 573.

At block 579, the one or more hardware processors can determine a location of a subject based on at least determining a location of the monitoring hub. The one or more hardware processors can access location data associated with the monitoring hub. The one or more hardware processors can access the location data by retrieving the location data from memory. The one or more hardware processors can access the location data by receiving the location data from one or more sensors, such as a sensor configured to generate location data, such as a GPS. In some implementations, the location data may be set by a user and stored in a memory associated with the monitoring hub. The location data can indicate a location of the monitoring hub. The location data can indicate a location of the monitoring hub relative to an environment. As an example, the location data can indicate that the monitoring hub is location is a specific region of a building, such as a hospital, such as in a specific floor level or room. The location data may also indicate a location of the one or more sensors (and the subject wearing the sensors) because the one or more sensors may be in proximity to the monitoring hub as determined at block 575.

In some implementations, one or more hardware processors executing on the monitoring hub may determine the location of the subject. For example, the one or more hardware processors can access location data of the monitoring hub and/or determine the location of the subject and transmit said location to a remote computing device. The one or more hardware processors may transmit the location data to a server, such as server 106 shown and/or described herein. The one or more hardware processors can transmit the location data via one or more wireless communication protocols such as WiFi.

In some implementations, one or more hardware processors executing on a computing device remote to the monitoring hub, such as a server, may determine the location of the subject. For example, the one or more hardware processors can receive an indication that the one or more sensors are within a proximity of the monitoring hub and/or may receive an indication that the monitoring hub has established wireless communication with the one or more sensors. In response, the one or more hardware processors can determine a location of the subject based at least on determining a location of the monitoring hub such as by retrieving location data of the monitoring from memory and/or receiving location data of the monitoring hub from the monitoring hub and/or from one or more sensors configured to generate location data.

Advantageously, in some implementations the one or more hardware processors may not determine the location unless the one or more hardware processors have established wireless communication (such as a Bluetooth connection) between the monitoring hub and the one or more sensors.

Determining location in response to establishing wireless communication may improve location monitoring by ensuring that using valid location data. For example, the one or more sensors may establish wireless communication with the closest monitoring hub of a plurality of monitoring hubs within an environment. Accordingly, the location of the monitoring hub that has established wireless communication with the one or more sensors (which may also be the closest to the one or more sensors) may be used to determine a location of the one or more sensors and subject. Accordingly, determining location in response to establishing wireless communication may improve an accuracy of monitoring a location of a subject.

Various methods are disclosed herein which relate to transferring wireless connectivity and/or physiological data (e.g., previously collected data) from a first monitoring hub to a second monitoring hub (and, in some cases, additionally to a third monitoring hub). Any of such disclosed methods and/or features described with respect to any of the monitoring hubs described herein can be applicable to other types of monitoring devices, such as monitoring devices that are configured to secure to a user and receive physiological data from one or more physiological sensors that obtain physiological data of the user. For example, any of the disclosed methods can be utilized to transfer wireless connectivity and/or physiological data (e.g., previously collected data) from a first monitoring device configured to be secured to a portion of a user's body and receive physiological data from physiological sensor(s) to a second similar monitoring device. Such monitoring devices can be worn by a user (for example, on a wrist, arm, or on another portion of the user's body) and can be configured to wirelessly (and/or via wired connection) receive physiological data from physiological sensor(s) and further configured to wirelessly (and/or via wired connection) communicate with other devices.

Example Monitoring Hubs

Figure 6:
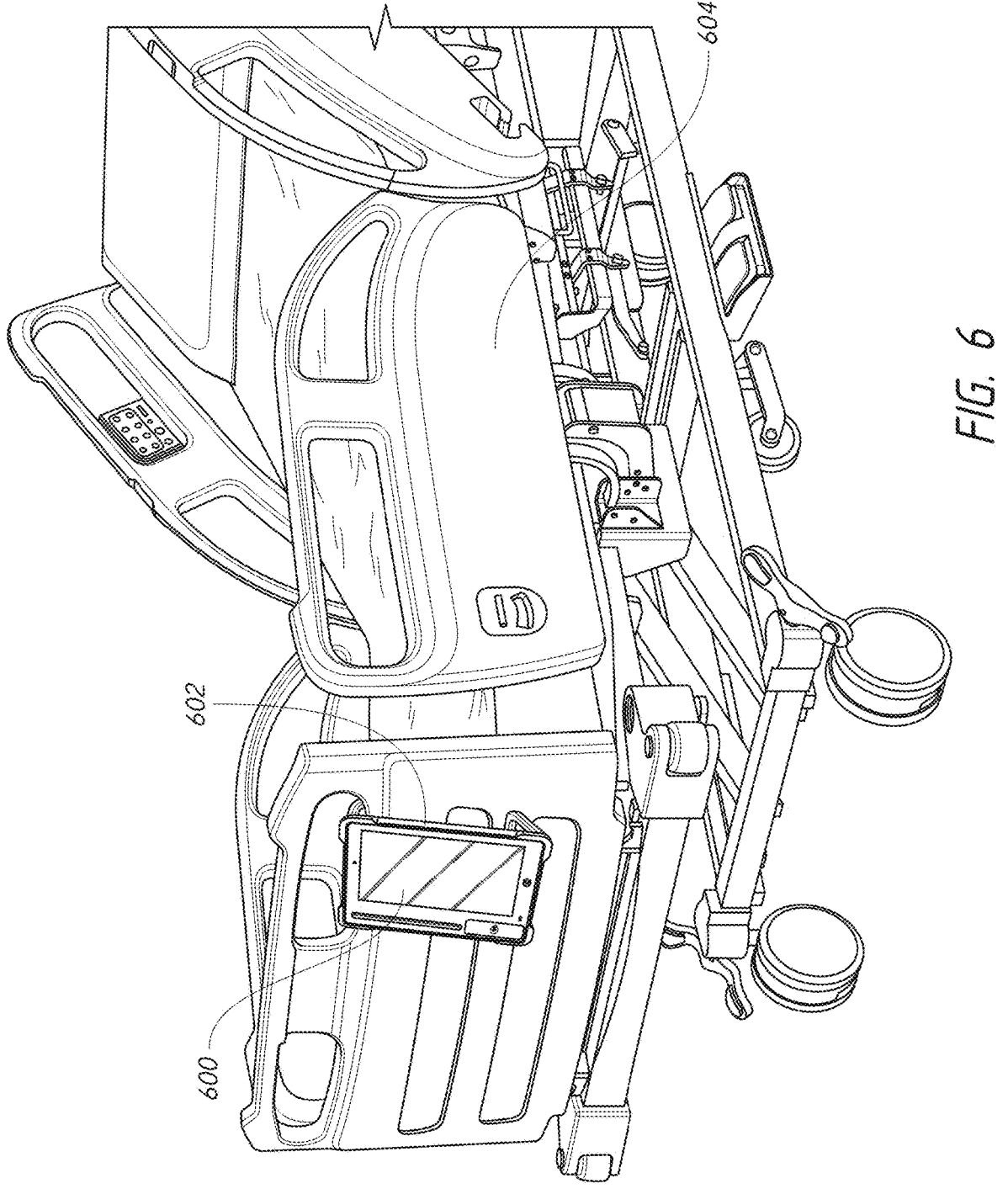
FIG. 6 illustrates an example implementation of a monitoring hub.

FIG. 6 illustrates an example monitoring hub 600. Monitoring hub 600 may include similar structural and/or operational features as any of the other monitoring hubs discussed herein. In some implementations, monitoring hub 600 may operate in a manner similar to any of the origin monitoring hubs disclosed herein. In some implementations, monitoring hub 600 may operate in a manner similar to any of the destination monitoring hubs disclosed herein.

In some implementations, monitoring hub 600 is portable device. Monitoring hub 600 may communicate with one or more computing devices (e.g., sensors, servers, other monitoring hubs, etc.) via a wireless connection such as via one or more wireless communication protocols (e.g., any of the wireless communication protocols disclosed herein). Monitoring hub 600 may include a battery to allow components of the monitoring hub 600 to operate. Monitoring hub 600 may be configured for wired communication with other devices (e.g., sensors, servers, other monitoring hubs, or the like). Monitoring hub 600 may be configured to receive power via a wired connection to an external power source.

FIG. 6 illustrates monitoring hub 600 housed within a holder 602. Monitoring hub 600 may be removably housed within holder 602. For example, monitoring hub 600 may be removably mechanically mated (e.g., via friction fit) with holder 602. Advantageously, holder 602 may improve portability and/or mobility of monitoring hub 600. For example, a user may more easily hold and carry monitoring hub 600 when housed within holder 602. Holder 602 may also serve to protect monitoring hub 600 or portions thereof. As another example, as shown in FIG. 6, the holder 602 can secure the monitoring hub 600 to a bed 604 to facilitate relocating monitoring hub 600 and the bed 604 together. For example, a user may be able to move the bed 604 and monitoring hub 600 together by pushing the bed 604 without having to simultaneously hold the monitoring hub 600. Advantageously, the portability of the monitoring facilitates continuous physiological monitoring and/or subject mobility. For example, monitoring hub 600 may continuously monitor the physiological data of a subject laying in the bed 604 while the subject is being transported to a new location such as a different room in a hospital. Monitoring hub 600 can maintain wireless communication with sensors on the subject in the bed 604 as well as with a server via a network as monitoring hub 600 and bed 604 are relocated without the need to unplug and/or replug any connections with monitoring hub 600. Each of monitoring hub 600, 700, and/or 1100, which are described further below, can include similar or identical operational and/or structural features. Holder 602 can include similar or identical operational and/or structural features as holder 800 discussed further below.

FIGS. 7A-7K illustrate various views of a monitoring hub 700. Monitoring hub 700 can be similar or identical in some or many respects to any of the monitoring hubs discussed elsewhere herein. For example, monitoring hub 700 can include any features described with respect to any of the other monitoring hubs described herein and/or monitoring hub 700 can be configured to operate in any manner as that described elsewhere herein with respect to any of the other monitoring hubs described herein. Furthermore, monitoring hub 700 can be an implementation of any of the monitoring hubs described herein.

Figures 7A, 7B, 7C:
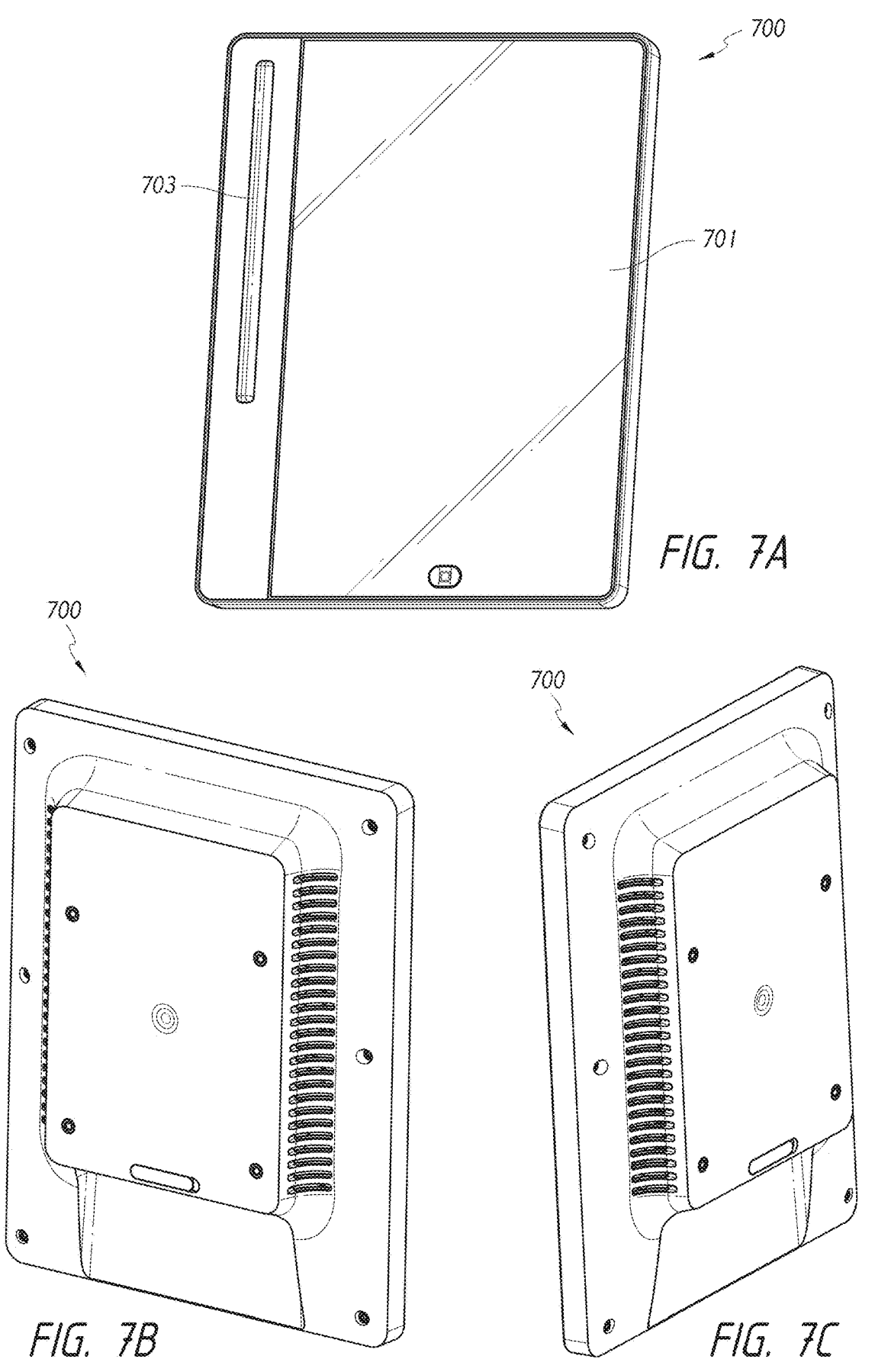
FIG. 7A illustrates a front perspective view of a monitoring hub in accordance with aspects of this disclosure.
FIGS. 7B-7C illustrate rear, top perspective views of the monitoring hub of FIG. 7A in accordance with aspects of this disclosure.

Monitoring hub 700 can include a display 701, for example, on a front portion of the monitoring hub 700 (see FIG. 7A). Display 701 can include any of the features and/or functionality of any of the other displays shown or described elsewhere herein. In some implementations, monitoring hub 700 includes a status indicator 703 which can be similar or identical to any or all of status indicators 304, 314 described elsewhere herein.

Figure 7D:
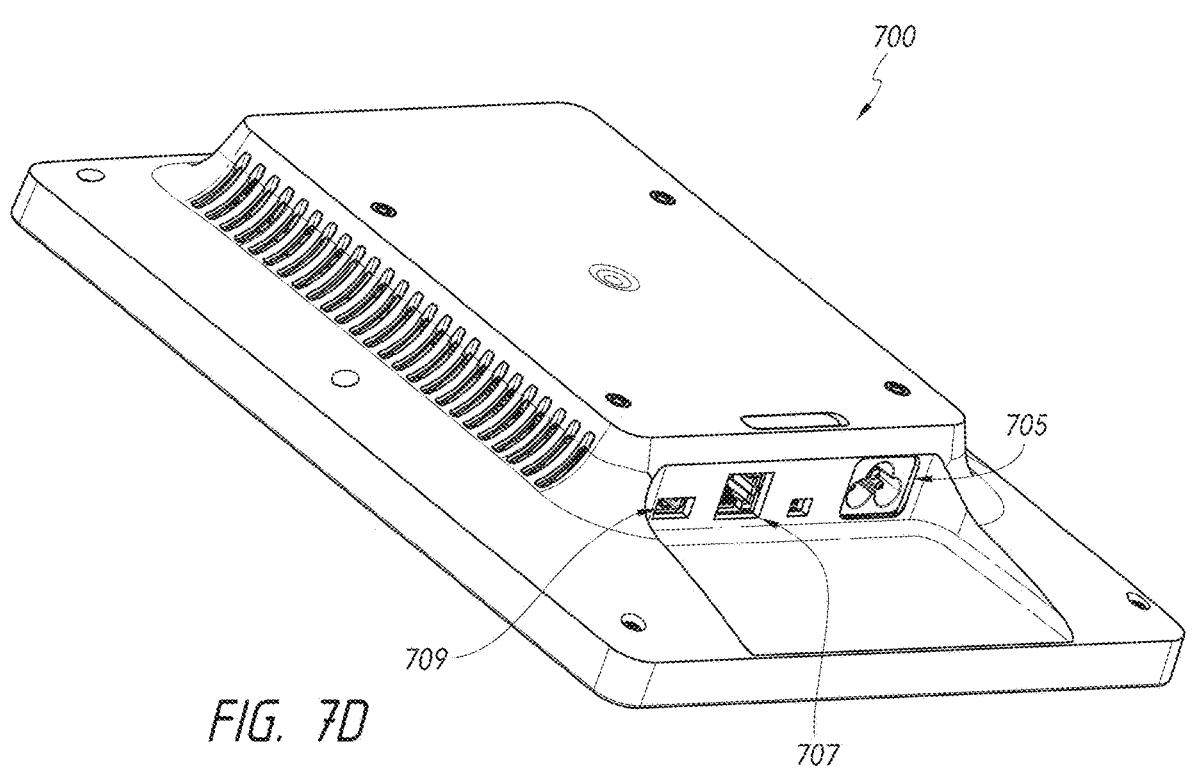
FIGS. 7D-7E illustrate rear, bottom perspective views of the monitoring hub of FIG. 7A in accordance with aspects of this disclosure.
Figure 7E:
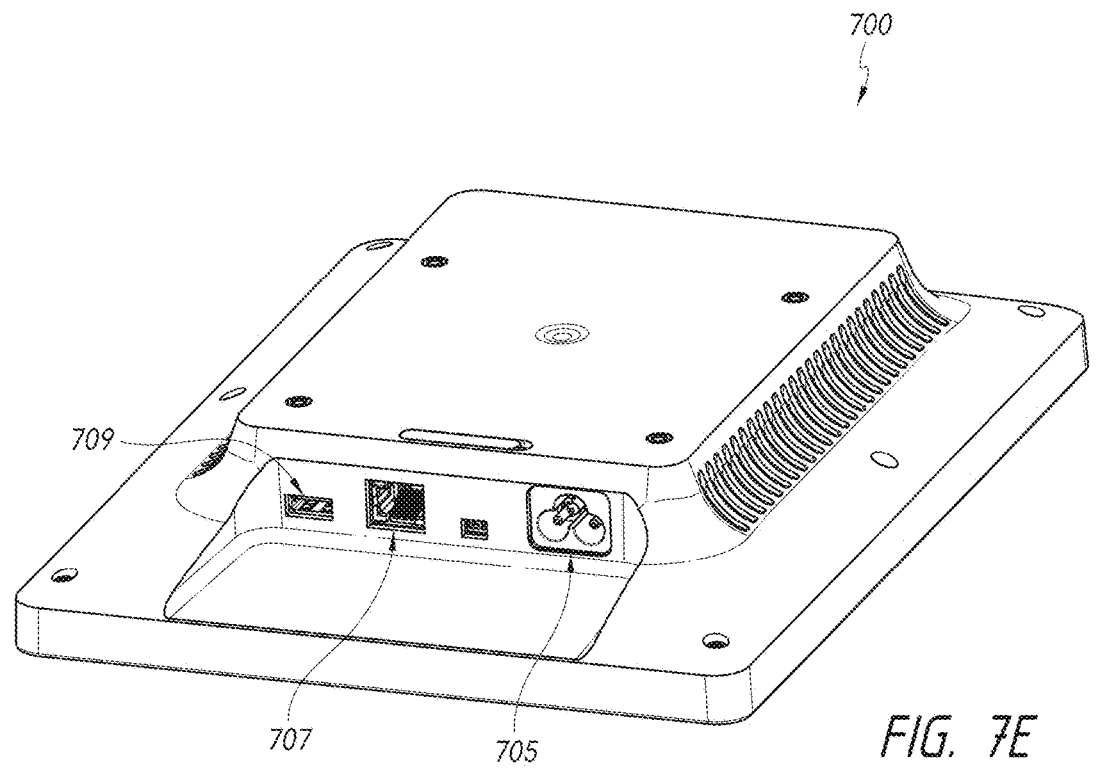

In some implementations, monitoring hub 700 is configured to receive power from an external power source, for example, via a power cable that can be connected to a connector port of monitoring hub 700, such as connector port 705 illustrated in at least FIGS. 7D-7E. In some implementations, monitoring hub 700 includes an internal power source (for example, a battery) contained within a portion of monitoring hub 700 (for example, a housing of monitoring hub 700). In some implementations, monitoring hub 700 includes an internal power source and also includes a connector port (such as connector port 705). Such implementations can advantageously allow: monitoring hub 700 to draw power necessary for operation from the internal power source despite not being connected to an external power source (for example, via a cable connected to connector port 705); monitoring hub 700 to draw power from (for example, only from) an external power source when connected via a cable; and/or can allow an internal power source of the monitoring hub 700 to be charged by an external power source. In some implementations in which monitoring hub 700 includes an internal power source, monitoring hub 700 can be configured to enable such internal power source to be charged via inductive charging. Monitoring hub 700 can be configured to operate upon AC and/or DC power. In some implementations, monitoring hub 700 includes an AC power connector port and a DC power connector port separate from the AC power connector port. In some implementations in which monitoring hub 700 includes an internal power source, such internal power source can have a charge life equal to or greater than 2 hours, 3 hours, or 4 hours. In some implementations, monitoring hub 700 includes one or more speakers for emitting sound, for example, alarms, communication from a caregiver (for example, inquiring as to user/patient condition, or otherwise communicating with the user/patient), among other things. Monitoring hub 700 can include a USB port configured to connect to a USB cable (such as USB port 709 as shown in FIGS. 7D-7E) and/or can include an Ethernet port configured to connect to an Ethernet cable (such as Ethernet port 707 as shown in FIGS. 7D-7E).

Figures 7F, 7G:
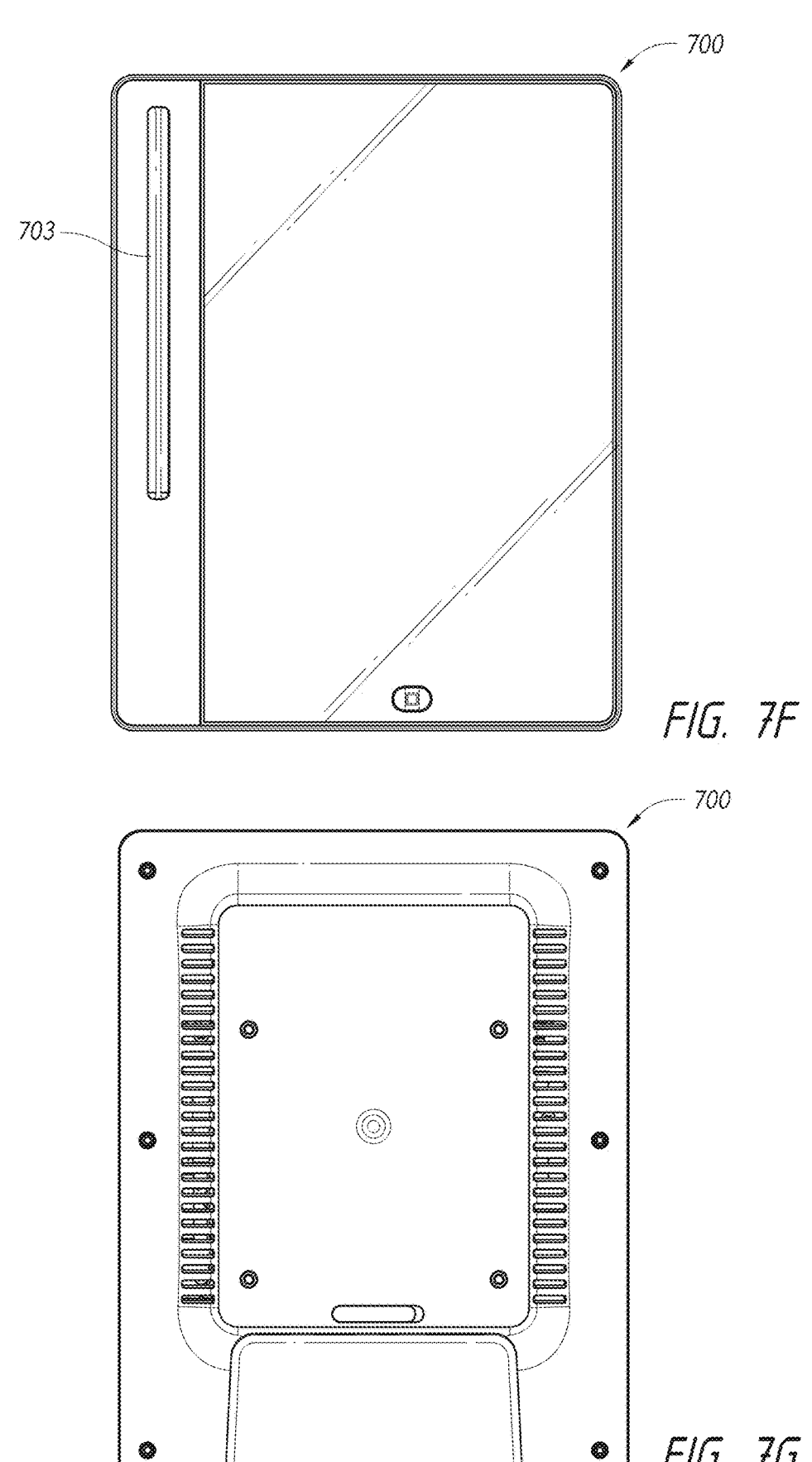
Figure 7H:
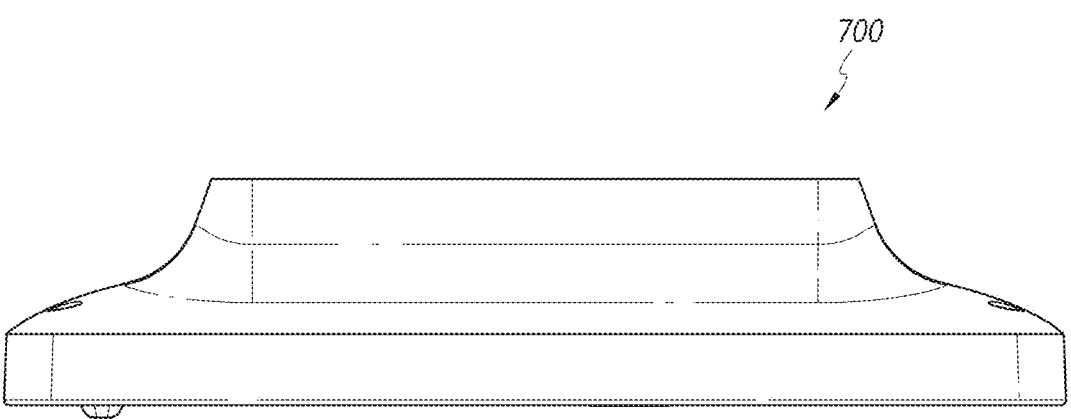
Figure 7I:
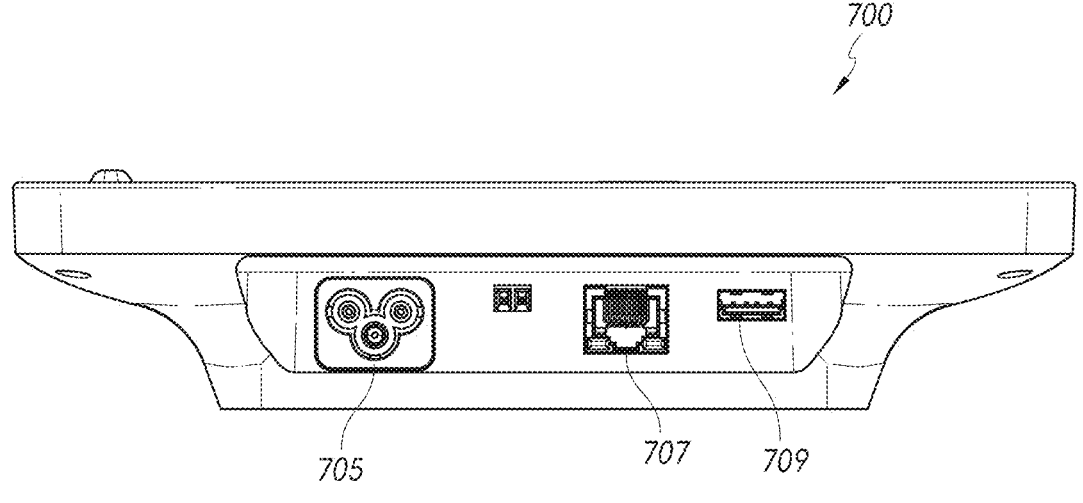

As illustrated, for example, in FIG. 7F, monitoring hub 700 can have a height of about 10 inches (measured vertically with respect to the page). In some implementations, monitoring hub 700 may have a height of greater than 10 inches, such as 12 inches, 14 inches, or greater. In some implementations, monitoring hub 700 may have a height of less than 10 inches, such as less than 9 inches, less than 8 inches, or less than 6 inches. Monitoring hub 700 can have a width of about 8 inches (measured horizontally with respect to the page). In some implementations, monitoring hub 700 may have a width of greater than 8 inches, such as 9 inches, 10 inches, or greater. In some implementations, monitoring hub 700 may have a width of less than 8 inches, such as less than 7 inches, less than 6 inches, or less than 5 inches. Display 701 can have a height of about 9 inches. In some implementations, display 701 may have a height of greater than 9 inches, such as 10 inches, 11 inches, or greater. In some implementations, display 701 may have a height of less than 9 inches, such as less than 8 inches, less than 7 inches, or less than 6 inches. Display 701 can have a width of about 6 inches. In some implementations, display 701 may have a width of greater than 6 inches, such as 7 inches, 8 inches, or greater. In some implementations, display 701 may have a width of less than 6 inches, such as less than 5 inches, less than 4 inches, or less than 3 inches.

FIGS. 11A-11C illustrate front, rear, and side views (respectively) of another implementation of a monitoring hub 1100. Monitoring hub 1100 can be an implementation of any of the other monitoring hubs discussed elsewhere herein. In some implementations, monitoring hub 1100 is configured to be received and/or supported by holder 800. As shown in FIG. 11B, monitoring hub 1100 can include openings 1101 that can receive a portion (for example, a head) of a fastener to allow hub 1100 to be mounted to a surface or object (for example, a wall). While FIGS. 11A-11C illustrates a cable connected to monitoring hub 1100, monitoring hub 1100 can be configured to receive power from an internal power source, for example, that can be charged without needing to connect to a cable (for example, via inductive charging). Moreover, monitoring hub 1100 can be configured to receive data via wireless transmission without needing to connect to a cable.

FIGS. 12A-12M illustrate various views of a monitoring hub 1200. Monitoring hub 1200 can be similar or identical in some or many respects to any of the monitoring hubs discussed elsewhere herein. For example, monitoring hub 1200 can include any features described with respect to any of the other monitoring hubs described herein and/or monitoring hub 1200 can be configured to operate in any manner as that described elsewhere herein with respect to any of the other monitoring hubs described herein. Furthermore, monitoring hub 1200 can be an implementation of any of the monitoring hubs described herein.

Figure 12A:
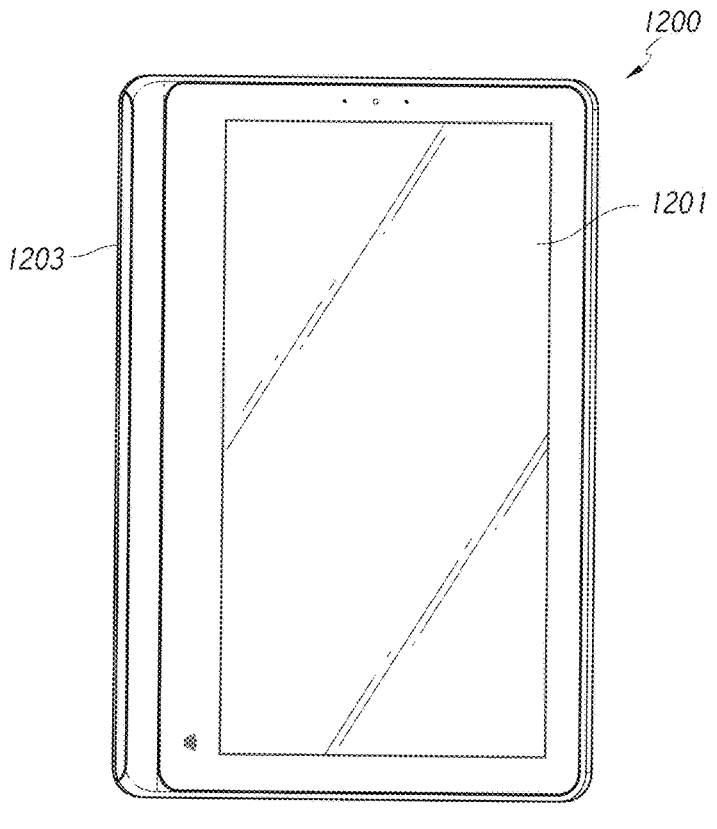
FIG. 12A illustrates a front perspective view of a monitoring hub in accordance with aspects of this disclosure.
Figure 12B:
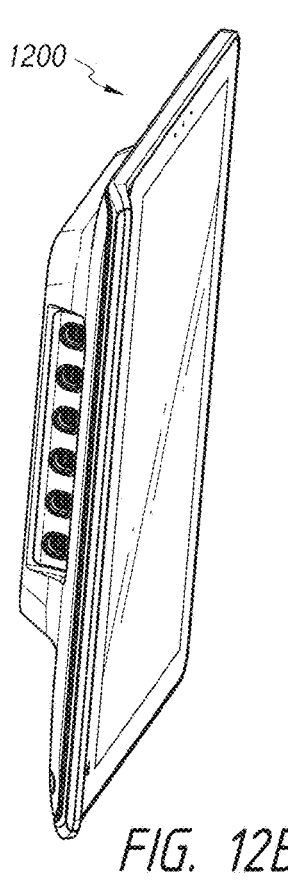
FIG. 12B illustrates a side perspective view of a monitoring hub in accordance with aspects of this disclosure.
Figure 12C:
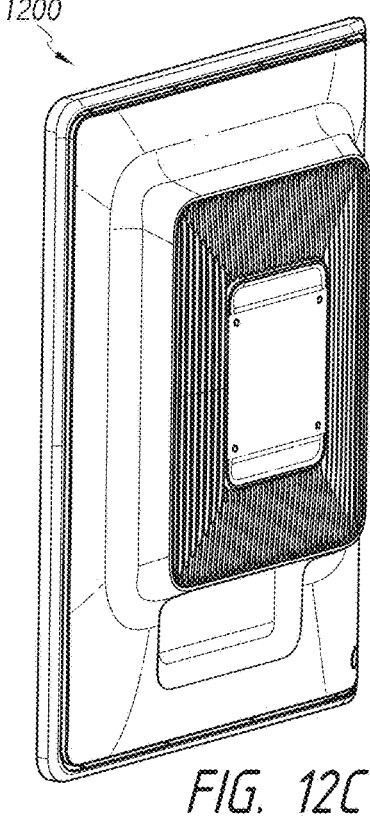
FIGS. 12C-12D illustrate rear, top perspective views of the monitoring hub of FIG. 12A in accordance with aspects of this disclosure.
Figure 12D:
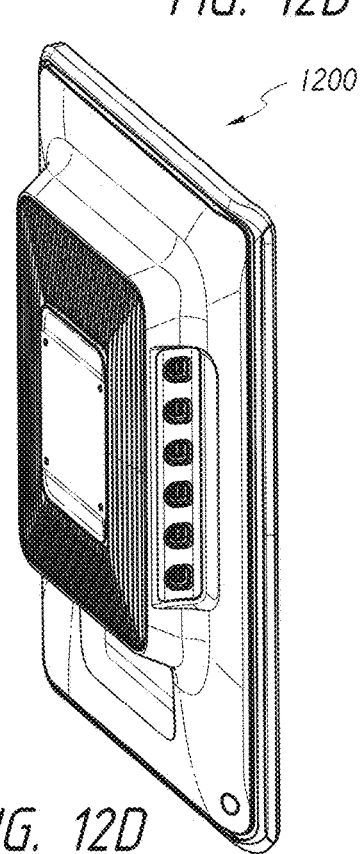

Monitoring hub 1200 can include a display 1201, for example, on a front portion of the monitoring hub 1200 (see FIG. 12A). Display 1201 can include any of the features and/or functionality of any of the other displays shown or described elsewhere herein. In some implementations, monitoring hub 1200 includes a status indicator 1203 which can be include similar structural and/or operational features as any or all of status indicators described elsewhere herein.

Figure 12E:
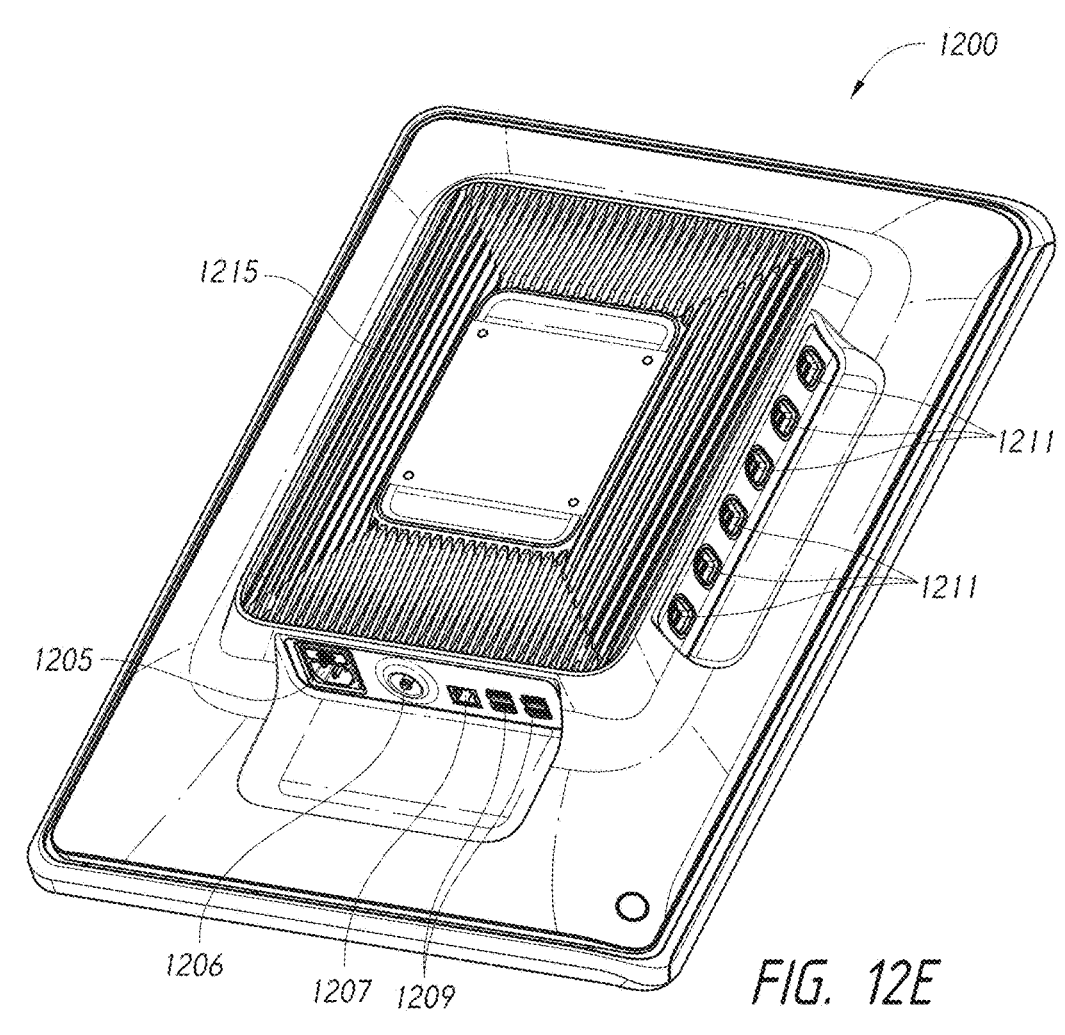
FIGS. 12E-12F illustrate rear, bottom perspective views of the monitoring hub of FIG. 12A in accordance with aspects of this disclosure.
Figure 12F:
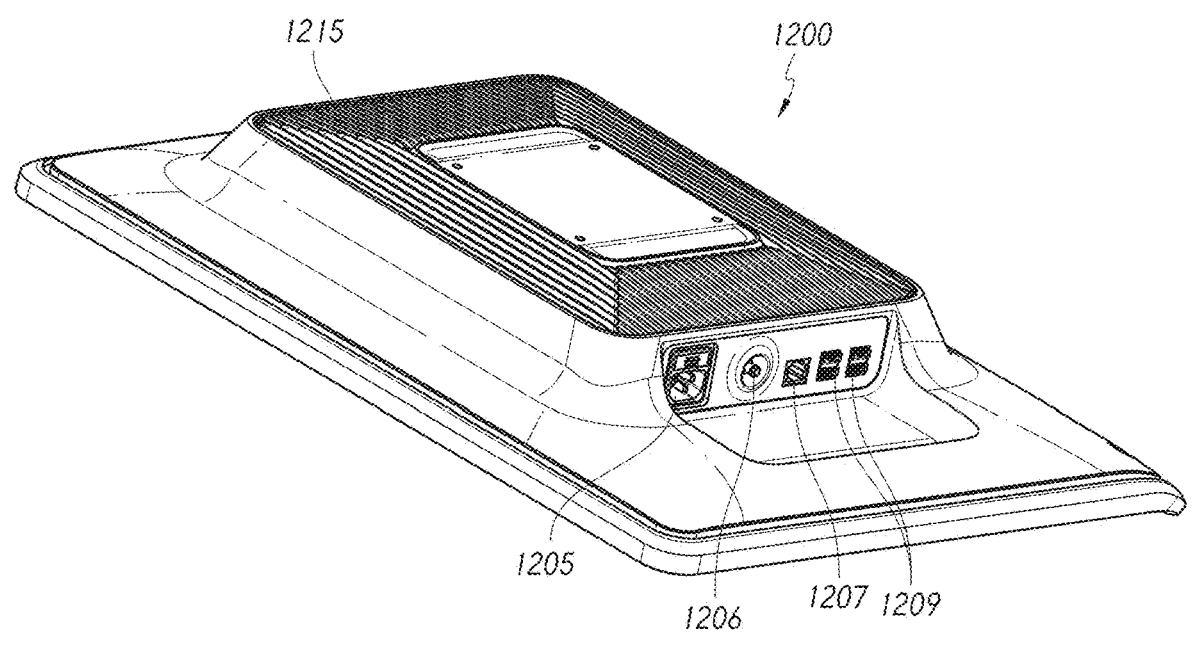
Figure 12G:
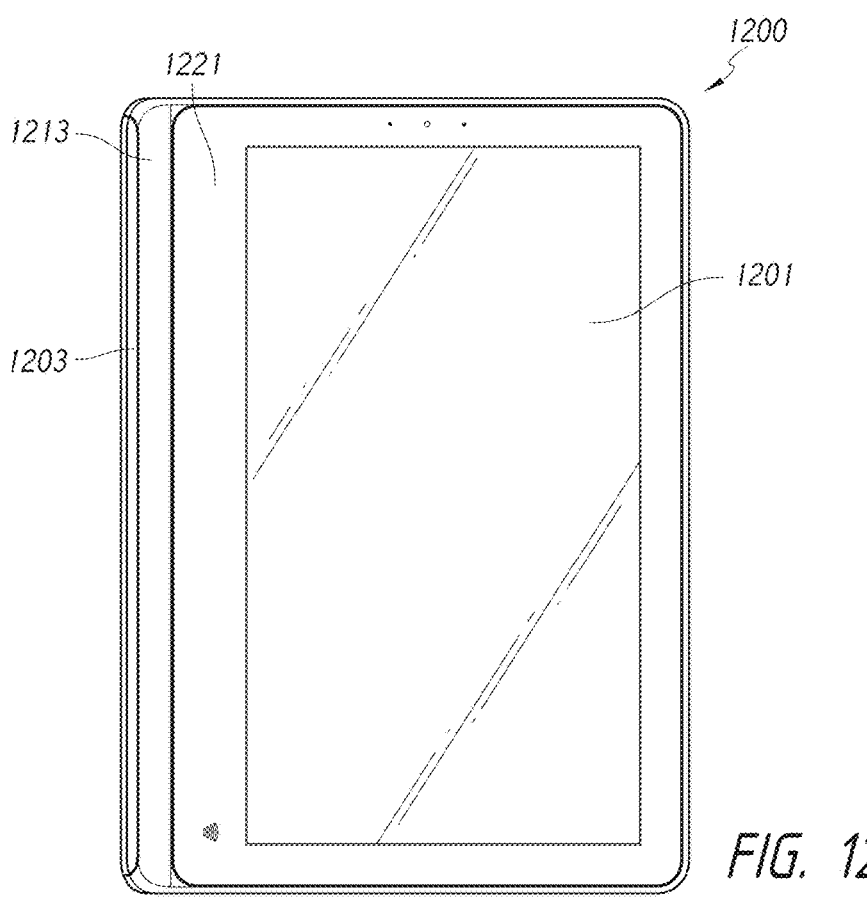
FIGS. 12G-12L illustrate front, rear, top, bottom, left side, and right side views (respectively) of the monitoring hub of FIG. 12A in accordance with aspects of this disclosure.
Figure 12H:
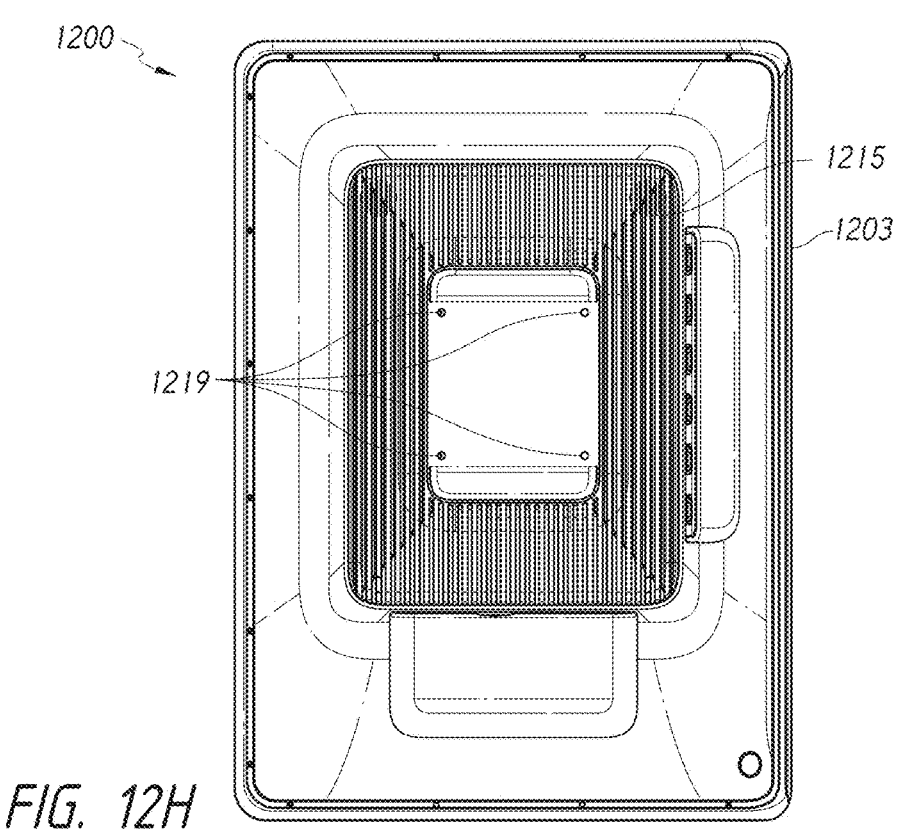
Figures 12I, 12J, 12K, 12L:
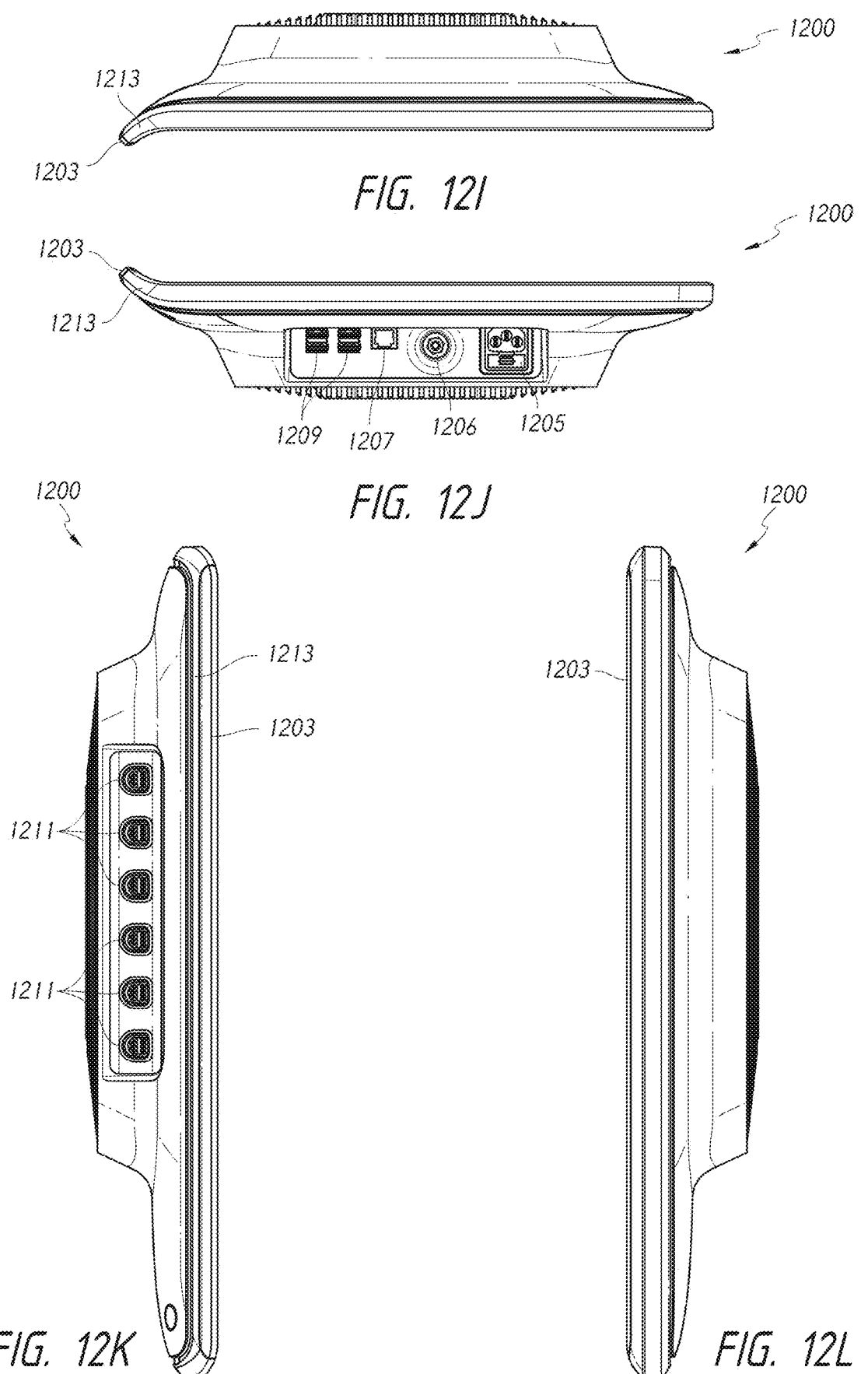

In some implementations, monitoring hub 1200 can receive power from an external power source, for example, via a power cable that can be connected to a connector port of monitoring hub 1200, such as connector port 1205 illustrated in at least FIGS. 12E, 12F, 12J. Monitoring hub 1200 can be configured to operate upon AC and/or DC power. In some implementations, monitoring hub 1200 includes an AC power connector port and a DC power connector port separate from the AC power connector port.

Monitoring hub 1200 can include a USB port configured to connect to a USB cable (such as USB ports 1209 as shown in at least FIGS. 12E, 12F, 12J) and/or can include an Ethernet port configured to connect to an Ethernet cable (such as Ethernet port 1207 as shown in at least FIGS. 12E, 12F, 12J).

Monitoring hub 1200 can include an auxiliary port 1206.

In some implementations, monitoring hub 1200 includes one or more speakers for emitting sound, for example, alarms, communication from a caregiver (for example, inquiring as to user/patient condition, or otherwise communicating with the user/patient), among other things.

Monitoring hub 1200 can include one or more sensor ports 1211. The monitoring hub can include more than three sensor ports 1211. The monitoring hub can include six sensor ports 1211. The monitoring hub 1200 can include one, two, three, four, five, six, seven, eight, nine, or more than nine sensor ports 1211. The sensor ports 1211 can be configured to connect to one or more sensors via a wired connection. The monitoring hub 1200 can receive physiological data originating from one or more sensors via the sensor ports 1211. The sensors ports 1211 can receive ECG data, heart rate data, blood oxygenation data, blood pressure data, EEG data, temperature data, respiration data, or the like. Each of the sensor ports 1211 may receive a different type of physiological data than the other sensor ports 1211. For example, a first sensor port 1211 can receive ECG data while another sensor port 1211 can receive SpO2 data. The sensor ports can receive a plurality of various types of physiological data simultaneously. A single sensor port 1211 may be configured to receive one or more types of sensors. A single sensor port 1211 may be configured to receive one or more types of physiological data. For example, a sensor port 1211 may receive blood pressure data via a wired connection with a blood pressure sensor and then the same sensor port 1211 may receive ECG data via a wired connection with an ECG sensor after unplugging and plugging respective sensors within the sensor port 1211.

As illustrated, for example in at least FIGS. 12G-12L monitoring hub 1200 can include a status indicator 1203. Status indicator 1203 can comprise one or more LEDs. Status indicator 1203 can emit light having one or more colors. Monitoring hub 1200 can include a curved portion 1213. Status indicator 1203 may be positioned on curved portion 1213. Curved portion 1213 can protrude from a portion of a housing of monitoring hub 1200. Curved portion 1213 may be non-planar with display 1201. Status indicator 1203 may be positioned on curved portion 1213 such that status indicator 1203 lies in a different plane than display 1201. Status indicator 1203 may be positioned on an end of curved portion 1213. Curved portion 1213 may comprise an edge of monitoring hub 1200. Status indicator 1203 may be positioned on an edge of monitoring hub 1200. Status indicator 1203 may be visible from a plurality of angles which may improve physiological monitoring of the patient as a caregiver may be able to view the status indicator 1203 from multiple positions around the monitoring hub 1200. Status indicator 1203 may be visible from a front or back of the monitoring hub 1200 (as shown for example in FIGS. 12G-12H). Status indicator 1203 may be visible from a top or bottom of the monitoring hub 1200 (as shown for example in FIGS. 121-12J). Status indicator 1203 may be visible from a left side or right side of the monitoring hub 1200 (as shown for example in FIGS. 12K-12L).

Figure 12M:
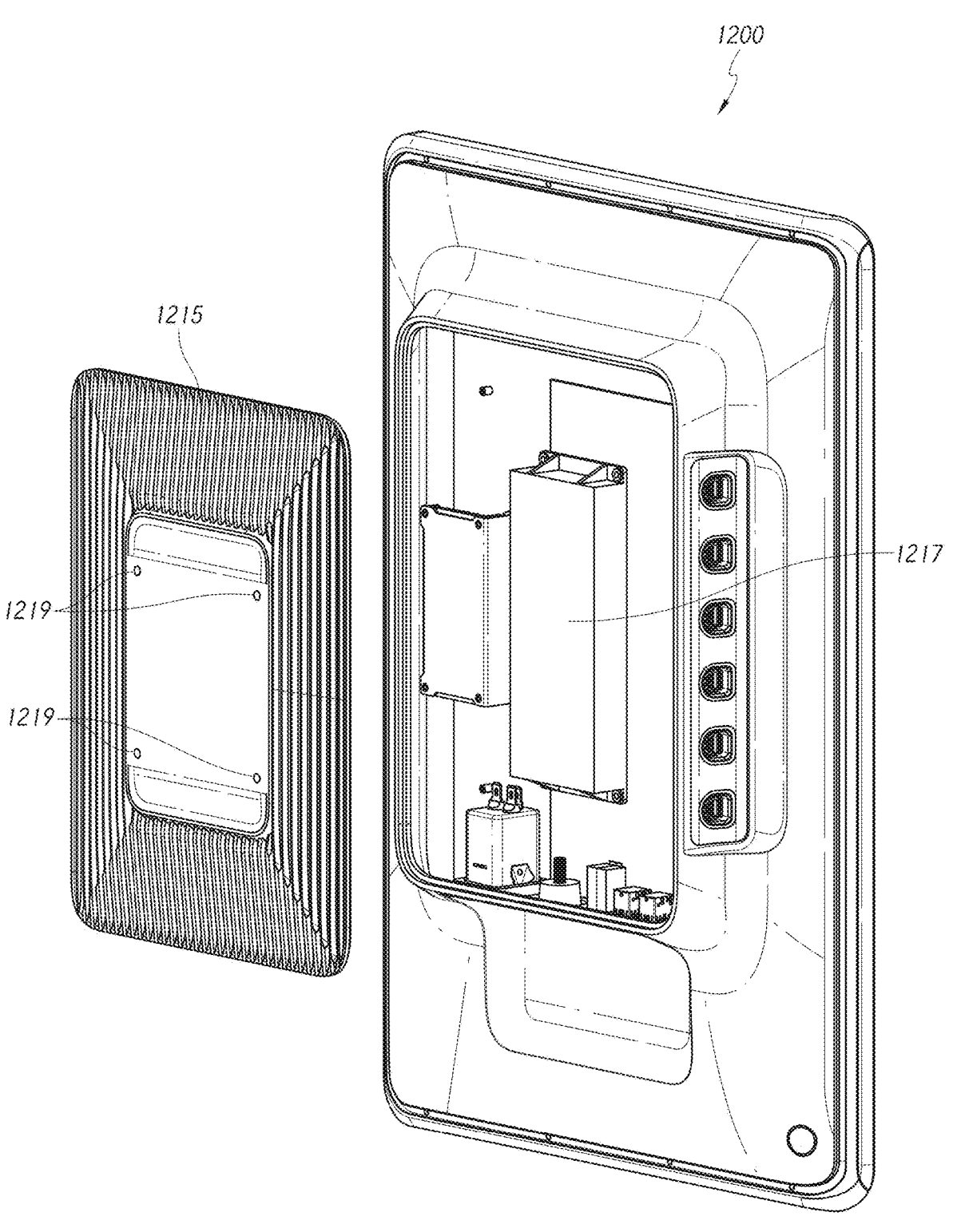
FIG. 12M illustrates a rear perspective exploded view of the monitoring hub of FIG. 12A in accordance with aspects of this disclosure.

As illustrated, for example in at least FIG. 12M, monitoring hub 1200 can include an internal power source (for example, a battery) contained within a portion of monitoring hub 1200 (for example, a housing of monitoring hub 1200). Monitoring hub 1200 can include a battery housing 1217 enclosing a battery within the monitoring hub 1200. In some implementations, monitoring hub 1200 includes an internal power source and also includes a connector port (such as connector port 1205). Such implementations can advantageously allow: monitoring hub 1200 to draw power necessary for operation from the internal power source despite not being connected to an external power source (for example, via a cable connected to connector port 1205); monitoring hub 1200 to draw power from (for example, only from) an external power source when connected via a cable; and/or can allow an internal power source of the monitoring hub 1200 to be charged by an external power source. In some implementations in which monitoring hub 1200 includes an internal power source, monitoring hub 1200 can be configured to enable such internal power source to be charged via inductive charging. In some implementations in which monitoring hub 1200 includes an internal power source, such internal power source can have a charge life equal to or greater than 2 hours, 3 hours, or 4 hours.

As illustrated, for example in at least FIG. 12M, monitoring hub 1200 can include a heat sink 1215. Heat sink 1215 may be formed of a metal and/or metal allow. Heat sink 1215 may dissipate heat from an interior region of monitoring hub 1200 to an exterior region of monitoring hub 1200. Heat sink 1215 may be positioned adjacent to an internal power source. Heat sink 1215 may be positioned adjacent to battery housing 1217. A portion of heat sink 1215 may be exposed to an exterior region of monitoring hub 1200. A portion of heat sink 1215 may not be exposed and/or may be disposed within an interior region of monitoring hub 1200. Heat sink 1200 may dissipate thermal energy from battery within battery housing 1217 to an exterior region of the monitoring hub 1200. Advantageously, the heat sink 1215 may provide passive cooling for the monitoring hub 1200. Advantageously, heat sink 1215 may obviate the need to implement an active cooling system, such as a fan, which may be noisy and consume more energy. In some implementations, heat sink 1215 may contact battery housing 1217. Heat sink 1215 may be removably coupled to the monitoring hub 1200. In some implementations, only the heat sink 1215 may enclose or cover the battery housing 1217 within an interior region of the monitoring hub 1200. In some implementations, the heat sink 1215 may form a portion of a housing of monitoring hub 1200. In some implementations, heat sink 1215 may cover or enclose an interior region of monitoring hub 1200.

Heat sink 1215 may include one or more through holes 1219. The heat sink 1215 may include less than five through holes 1219, less than four through holes 1219, less than three through holes 1219, or less than two through holes 1219. The heat sink 1215 may include four through holes 1219.

The through holes 1219 may receive one or more screws, nails, fasteners, or the like. The heat sink 1215 may secure to the monitoring hub 1200 by the through holes 1219. In some implementations, a user may remove the heat sink 1215 from the monitoring hub 1200 simply by removing screws from the through holes 1219. In some implementations, a user may couple the heat sink 1215 to the monitoring hub 1200 simply by placing screws into the through holes 1219. Advantageously, a user may easily remove and replace heat sink 1215 from monitoring hub 1200. Advantageously, a user may easily access battery housing 1217 by simply removing heat sink 1215. A user may desire to periodically replace an internal power source enclosed by battery housing 1217. A user can easily replace an internal power source simply by removing and replacing heat sink 1215, as described herein.

As illustrated, for example in at least FIG. 12G, monitoring hub 1200 can include a glass portion 1221. Glass portion 1221 can be positioned between the curved portion 1213 and the display 1201. Curved portion 1213 may be formed of metal. Curved portion 1213 may be formed of aluminum. Metal may affect operation of wireless components. For example, metal may detune antennas. Accordingly, positioning components configured for wireless communication in close proximity to metal may adversely affect operation of the wireless communication components. In some implementations, monitoring hub 1200 may include components configured for wireless communication, such as antennas, transceivers, radios, pairing devices, etc. which may be positioned within an interior region of the monitoring hub 1200 adjacent to glass portion 1221. Accordingly, wireless transmission from one or more wireless communication components may occur through glass portion 1221 which may improve quality of the wireless transmission. Moreover, positioning wireless communication components adjacent to glass portion 1221 may increase a distance between wireless communication components and metal such as metal of curved portion 1213 and/or metal within other portions of a frame or housing of monitoring hub 1200.

As illustrated, for example, in FIG. 12G, monitoring hub 1200 can have a height of about 21 inches (measured vertically with respect to the page). In some implementations, monitoring hub 1200 may have a height of greater than 21 inches, such as 23 inches, 26 inches, or greater. In some implementations, monitoring hub 1200 may have a height of less than 21 inches, such as less than 18 inches, less than 15 inches, or less than 12 inches. Monitoring hub 1200 can have a width of about 15 inches (measured horizontally with respect to the page). In some implementations, monitoring hub 1200 may have a width of greater than 15 inches, such as 17 inches, 19 inches, or greater. In some implementations, monitoring hub 1200 may have a width of less than 15 inches, such as less than 13 inches, less than 11 inches, or less than 9 inches. Display 1201 can have a height of about 19 inches. In some implementations, display 1201 may have a height of greater than 19 inches, such as 20 inches, 21 inches, or greater. In some implementations, display 1201 may have a height of less than 19 inches, such as less than 18 inches, less than 17 inches, or less than 16 inches. Display 1201 can have a width of about 11 inches. In some implementations, display 1201 may have a width of greater than 11 inches, such as 12 inches, 13 inches, or greater. In some implementations, display 1201 may have a width of less than 11 inches, such as less than 10 inches, less than 9 inches, or less than 8 inches.

Holder

Figures 8A, 8B:
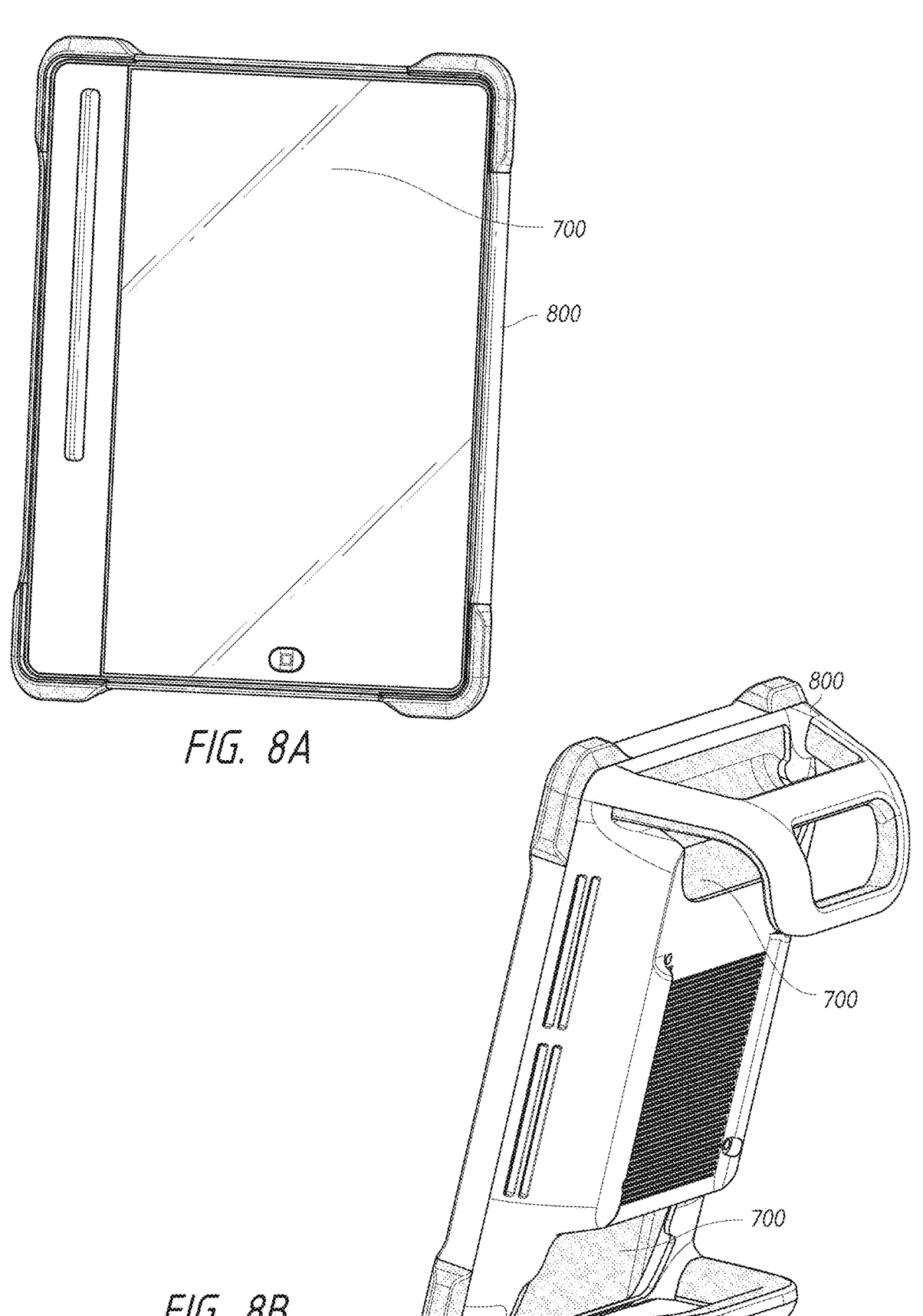
FIGS. 8A-8B illustrate views of the monitoring hub of FIG. 7A and a holder in accordance with aspects of this disclosure.

FIGS. 8A-8B illustrate monitoring hub 700 attached to a holder 800. Holder 800 can advantageously receive and surround portion(s) of monitoring hub 700 and can serve to protect monitoring hub 700. Holder 800 can also advantageously allow monitoring hub 700 to more easily be carried (for example, by a caregiver in a medical environment) and/or placed on a surface (for example, a table, bed, chair, desk) such that a display of monitoring hub 700 is viewable. Additionally, in some implementations, holder 800 can be configured to be secured to a portion of a hospital bed (and/or other objects), as further discussed below.

Figure 8C:
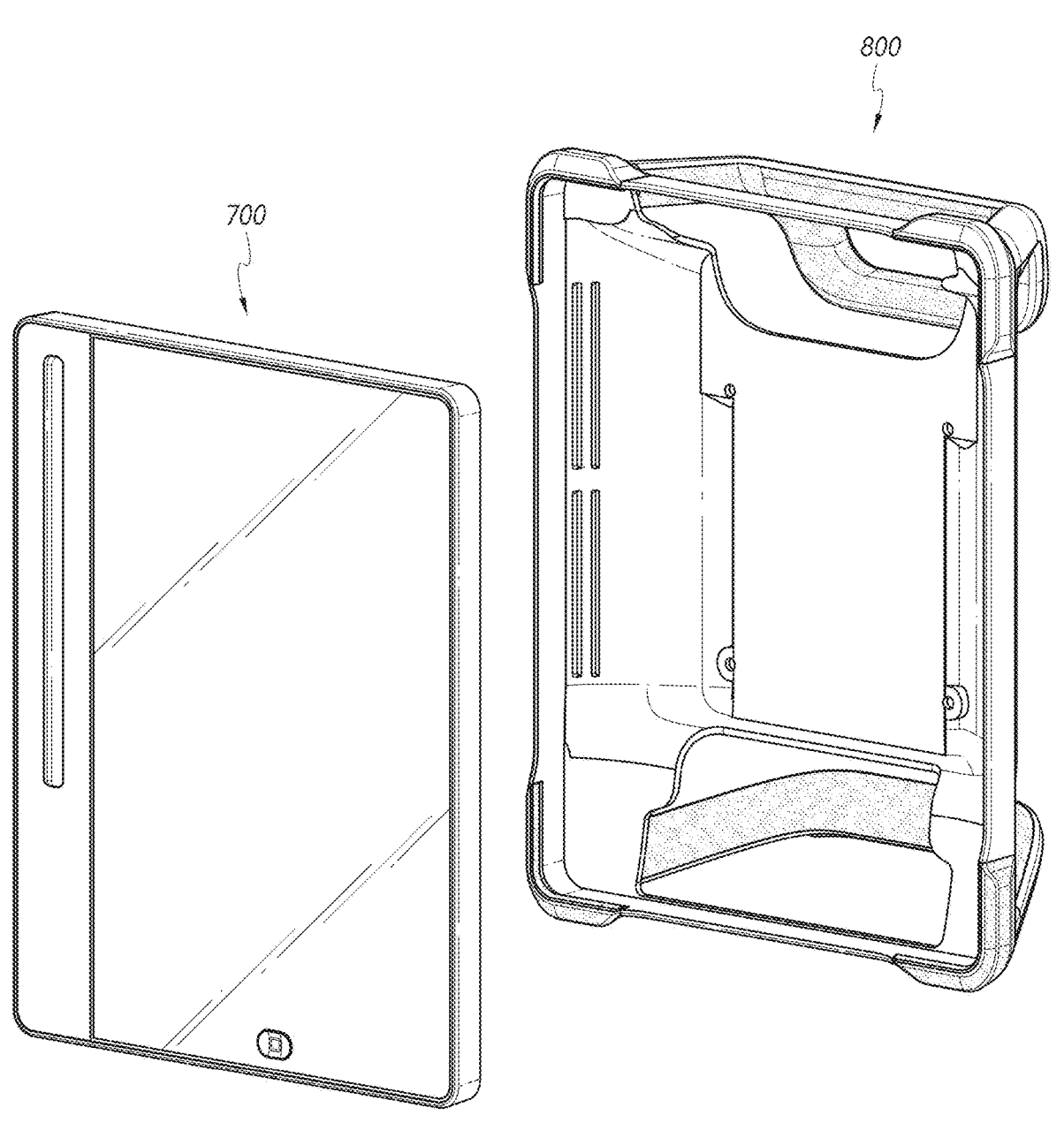
FIG. 8C illustrates the monitoring hub of FIG. 7A and the holder of FIGS. 8A-8B detached from one another in accordance with aspects of this disclosure.

FIG. 8C illustrates monitoring hub 700 and holder 800 detached from one another. Holder 800 can be sized to receive any of the example monitoring hubs shown and/or described herein.

Figures 8D, 8E:
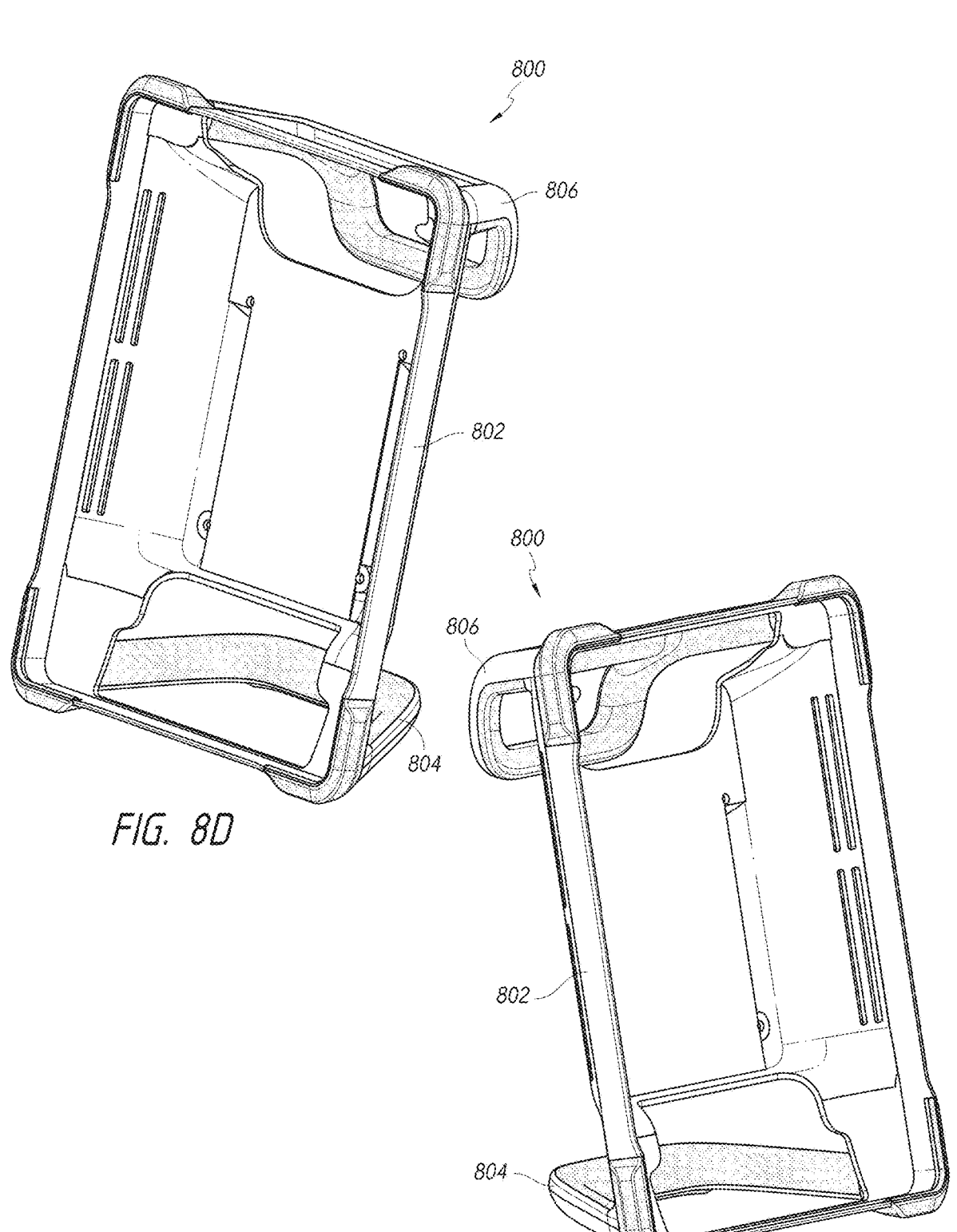
FIG. 8D-8E illustrate front, top perspective views of the holder of FIGS. 8A-8B in accordance with aspects of this disclosure.
Figures 8F, 8G, 8H, 8I:
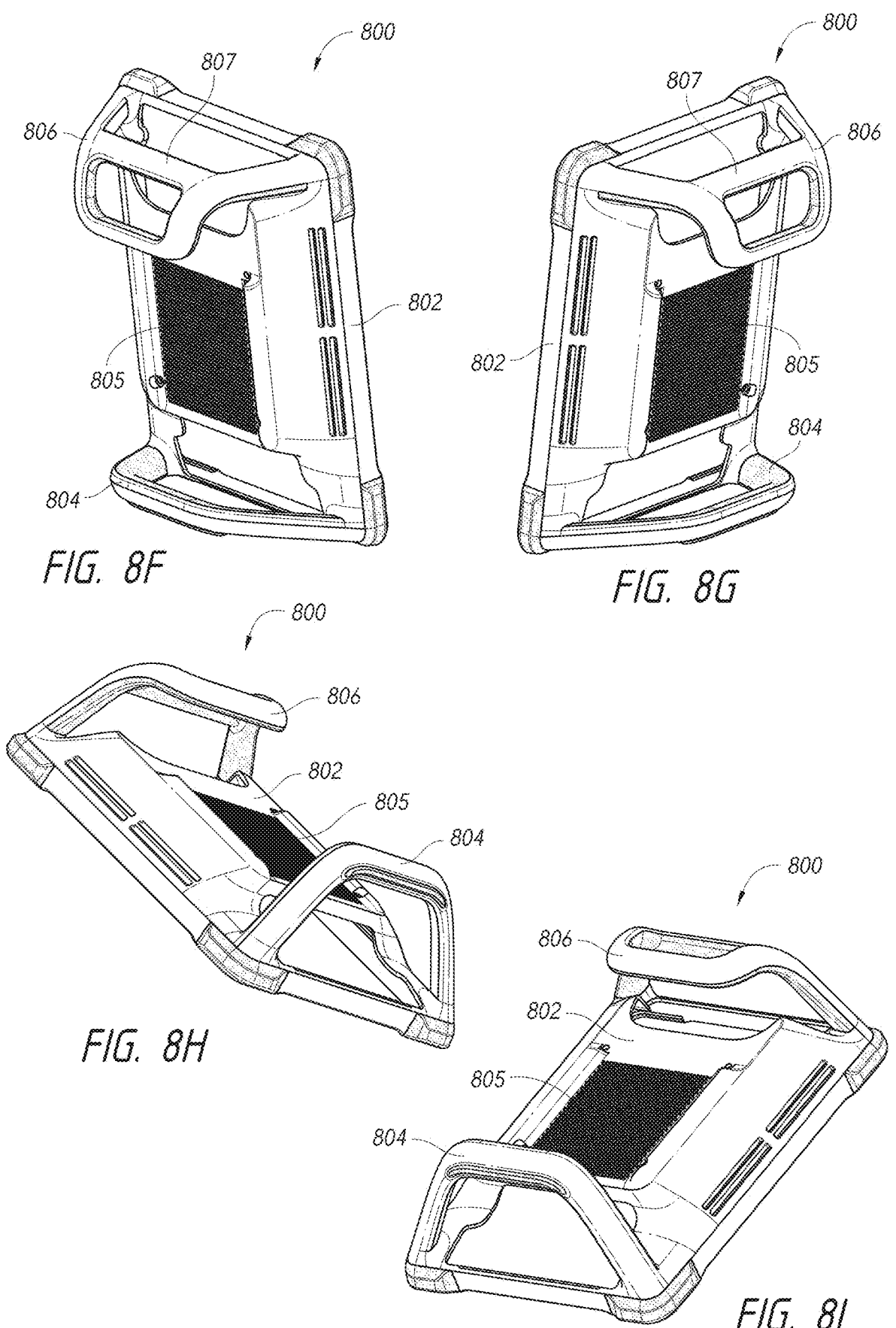
FIGS. 8F-8I illustrate rear perspective views of the holder of FIGS. 8A-8B in accordance with aspects of this disclosure.
Figures 8J, 8K:
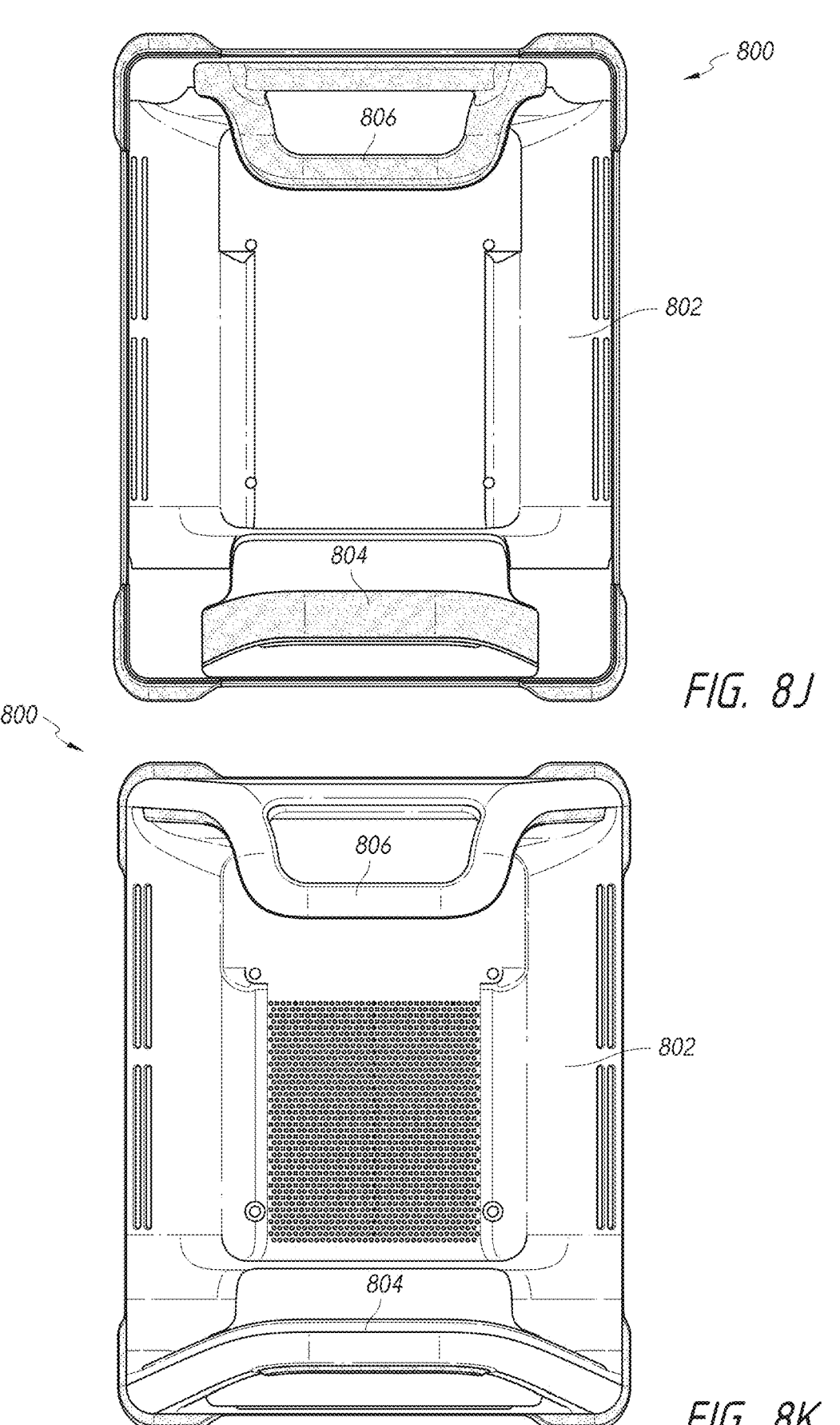
FIGS. 8J-8O illustrate front, rear, left side, right side, top, and bottom views (respectively) of the holder of FIGS. 8A-8B in accordance with aspects of this disclosure.
Figures 8L, 8M:
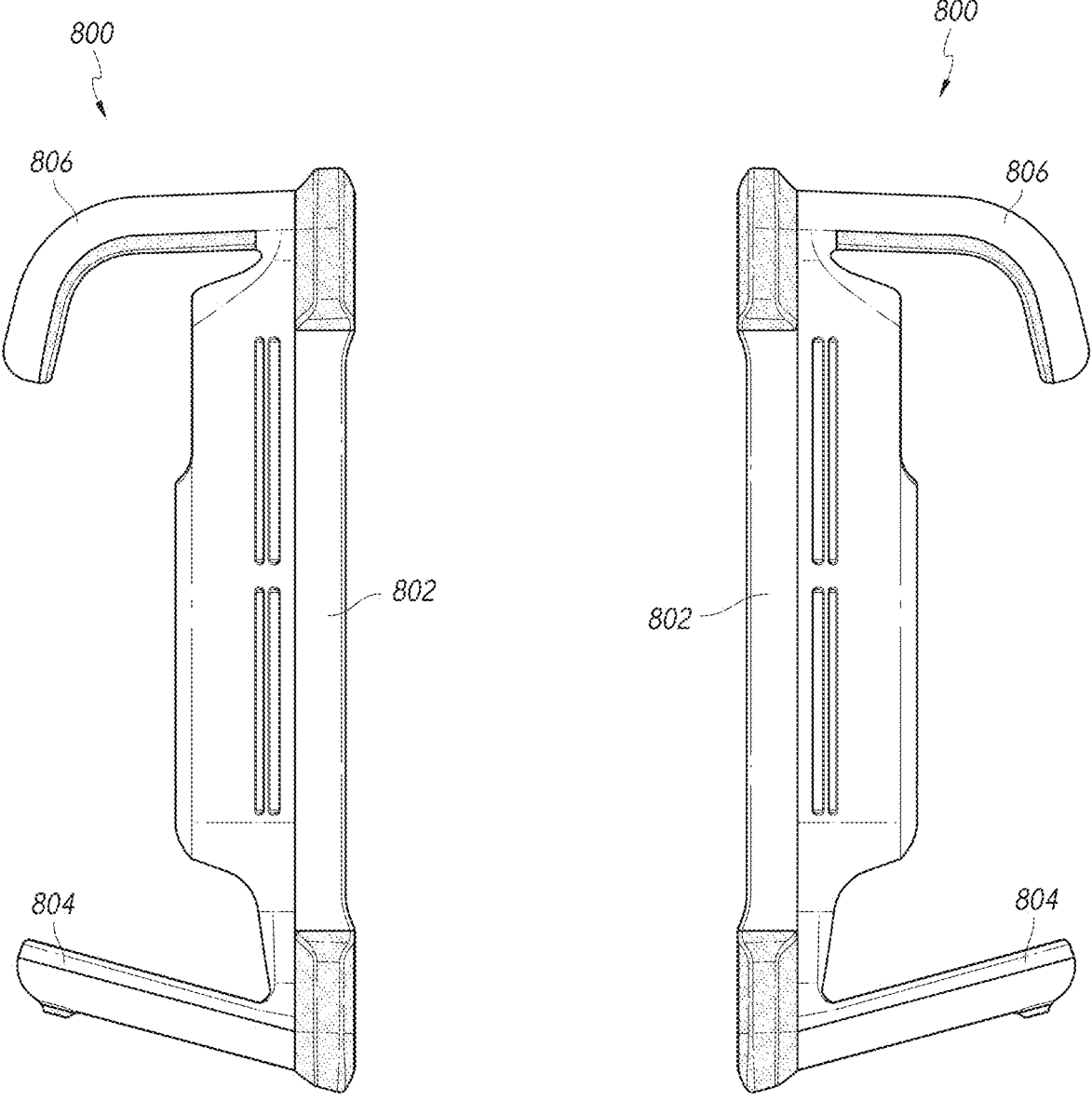
Figure 8N:
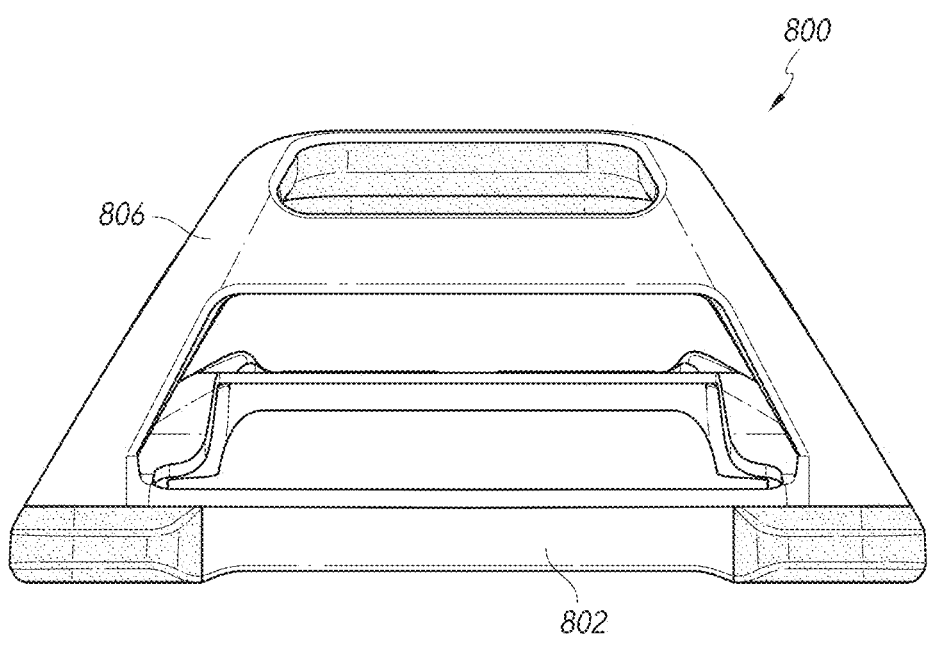
Figure 8O:
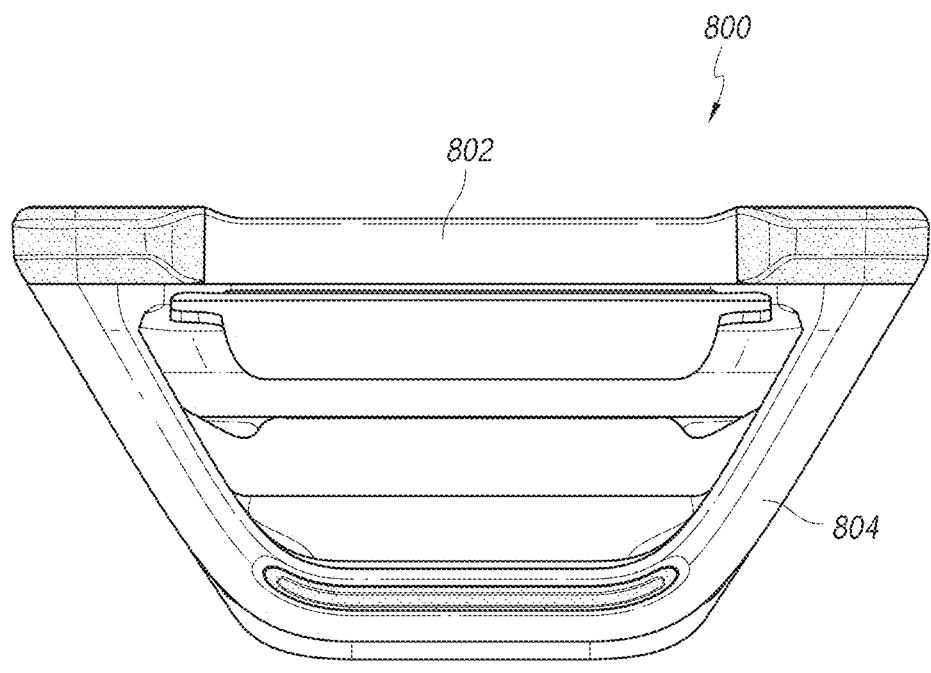

With reference to FIGS. 8D-80, holder 800 can include a base 802. Base 802 can be configured to receive and removably secure monitoring hub 700, for example, in a manner such that, when hub 700 is received and secured by base 802, a display of hub 700 is visible (see, e.g., FIG. 8A). Holder 800 can include one or more arms configured to interact with other objects and/or surfaces. For example, such one or more arms can be configured to: removably secure to a portion of a hospital bed or chair, among other objects such as poles, rails, among other things; and/or rest upon a surface so as to operably position the holder 800 (and monitoring hub 700, when positioned in holder 800), for example, such that a front of the holder 800 is positioned away from such surface (which can allow a display of hub 700 to be visible when secured in holder 800). For example, with reference to at least FIGS. 8D-80, holder 800 can include an arm 804 (which may be referred to as a "stand") extending outward from the base 802. Arm 804 can extend transverse (non-parallel) relative to base 802, which can allow the holder 800 to rest upon a surface (e.g., a table or desk) in a position. Arm 804 can be oriented nonparallel relative to base 802 such that, when arm 804 is positioned atop a support surface (such as a table, desk, among other things), base 802 is oriented nonparallel (and/or non-perpendicular) relative to such support surface. This can advantageously cause a hub 700 to be more accessible and/or a display of hub 700 to be more viewable when holder 800 rests atop a support surface.

As also shown in FIGS. 8D-80, holder 800 can include an arm 806. Arm 806 can be configured to removably secure to a portion of a hospital bed or chair. For example, arm 806 can be configured to "hook" onto a portion of a hospital bed as illustrated with respect to hub 600, holder 602 and bed 604 in FIG. 6. Arm 806 can include a first portion that extends outward from base 802 and a second portion connected to such first portion and that is transverse relative to such first portion. In some implementations, arms 804, 806 are integral with base 802. Arms 804, 806 may form a single integrated unit with the base 802. Arms 804, 806 may be fixed relative to the base 802. Arms 804, 806 may be non-adjustable. Arms 804, 806 may be configured to not be adjusted relative to the base 802. Arms 804, 806 may be rigid. In some alternative implementations, one or both of arms 804, 806 can be pivotably connected to base 802, which can allow an orientation of arm 804 and/or arm 806 to be changed relative to base 802 between a plurality of positions. Where arm 806 is pivotally connected to base 802, an inclination of a holder 800 relative to a surface which supports arm 806 can be changed, which can in turn adjust an inclination of monitoring hub 700 when attached to holder 800 (and, for example, a display of hub 700). Arms 804, 806 may facilitate orienting holder 800 at a plurality of orientations. For example, holder 800 may rest on a surface by resting on arms 804, or by resting on arms 806, or by resting on both arms 804 and 806 such as in a horizontal position.

In some implementations, arm 804 has a first end connected to a first portion of the base 802 and a second end connected to a second portion of the base 802, thereby forming a loop of holder 800, as can be seen in at least FIGS. 8F-8I. In some implementations, arm 806 includes a first end connected to a first portion of base 802 and a second end connected to a second portion of base 802, thereby forming a loop of holder 800. In some of such implementations, holder 800 includes a bar 807 extending between portions of the arm 806 which splits such loop formed by arm 806. Such bar 807 can be grasped by a user carrying the holder 800 (and hub 700 when received by holder 800). In some implementations, arm 806 comprises a hook that allows arm 806 to at least partially wrap around and/or rest atop an object and/or surface. For example, arm 806 can include a first portion that is connected to base 802 and a second portion that is connected to such first portion and which is transverse (nonparallel) relative to such first portion. Such configurations can advantageously allow arm 806 to secure to various support structures, such as a wall component at an end of a hospital bed as illustrated in FIG. 6, or a pole, rail, or other support structure.

In some implementations, the holder 800 is configured such that, when arm 806 is wrapped around and/or rests atop a top portion of a support structure (for example, a wall at an end of a hospital bed as shown in FIG. 6), arm 806 contacts the support structure (for example, a side surface of the support structure) and operably positions base 802 away from the support structure.

In some implementations, the holder 800 is configured such that, when arm 806 is wrapped around and/or rests atop a top portion of a support structure (for example, a wall at an end of a hospital bed as shown in FIG. 6), arm 806 contacts the support structure and operably positions the base 802 such that the base 802 is oriented substantially parallel relative to a plane extending along the support structure (for example, a plane extending along a side surface of the support structure). Such "support structures" can be generally perpendicular to a ground surface (for example, a floor of a hospital room or home). In some implementations, the holder 800 is configured such that, when arm 806 is wrapped around and/or rests atop a top portion of a support structure (for example, a wall at an end of a hospital bed as shown in FIG. 6), arm 806 contacts the support structure and operably positions the base 802 to be generally perpendicular to the ground surface, within 30 degrees of being perpendicular to the ground surface, within 20 degrees of being perpendicular to the ground surface, or within 10 degrees of being perpendicular to the ground surface.

Holder 800 can be made of a variety of materials, for example, rigid plastic among other materials. In some implementations, holder 800 includes an overmold of a soft material laid over a more rigid base material of the holder 800. In some implementations, portions of holder 800 can comprise a material that aids gripping (such as silicon and/or rubber), as illustrated by the shaded portions appearing in FIGS. 8A-80 (which contrast with the other unshaded portions of the holder 800). In some implementations, holder 800 includes one or more or a plurality of bumps 805 extending outward from a surface of base 802 which can help a user grip the holder 800 (for example, with the user's fingers), as illustrated in at least FIGS. 8F-8I and 8K.

Mounting Assemblies

Any of the monitoring hubs discussed herein can be mounted to a variety of objects and/or surfaces in a variety of ways. FIGS. 9A-9M illustrate a mounting assembly 900 (or portions thereof) that can allow monitoring hub 700 (or any of the other monitoring hubs shown and/or described herein) to be secured to a surface (such as a wall) or another object (such as a support arm that is itself mounted to a surface (such as a wall). FIGS. 10A-10K illustrate another implementation of a mounting assembly 1000 (or portions thereof) that can allow monitoring hub 700 (or any of the other monitoring hubs shown and/or described herein) to be secured to a surface (such as a wall) or another object (such as a support arm that is itself mounted to a surface (such as a wall). Mounting assemblies 900, 1000 can include a first portion that is configured to be secured to a portion of monitoring hub 700 (for example, a back portion of hub 700) and a second portion that is configured to be secured to a surface or object (such as a wall). Such first portion can be secured to the monitoring hub 700 via one or more fasteners (such as screws, or nails, or magnets) and such second portion can be secured to a surface or object (e.g., wall) via one or more fasteners (such as screws, or nails, or magnets). Advantageously, such first and second portions of the mounting assembly 900 can be secured (for example, removably secured) to one another without the need for one or more fasteners (such as screws or nails), which can allow for quick attachment and/or removal. Such quick attachment and/or removal of the first and second portions of the mounting assembly 900 can in turn advantageously allow for quick attachment and/or removal of monitoring hub 700 from an object or surface (for example, a wall). Such first portion can be mount 910 (with respect to mounting assembly 900 illustrated in FIGS. 9A-9M) or mount 1010 (with respect to mounting assembly 1000 illustrated in FIGS. 10A-10K). Such second portion can be mount 920 (with respect to mounting assembly 900 illustrated in FIGS. 9A-9M) or mount 1020 (with respect to mounting assembly 1000 illustrated in FIGS. 10A-10K). Each of mounts 910, 920, 1010, 1020 can also be referred to as "mounting portions". Mounting assemblies 900 and 1000 are discussed in turn below.

Figures 9A, 9B:
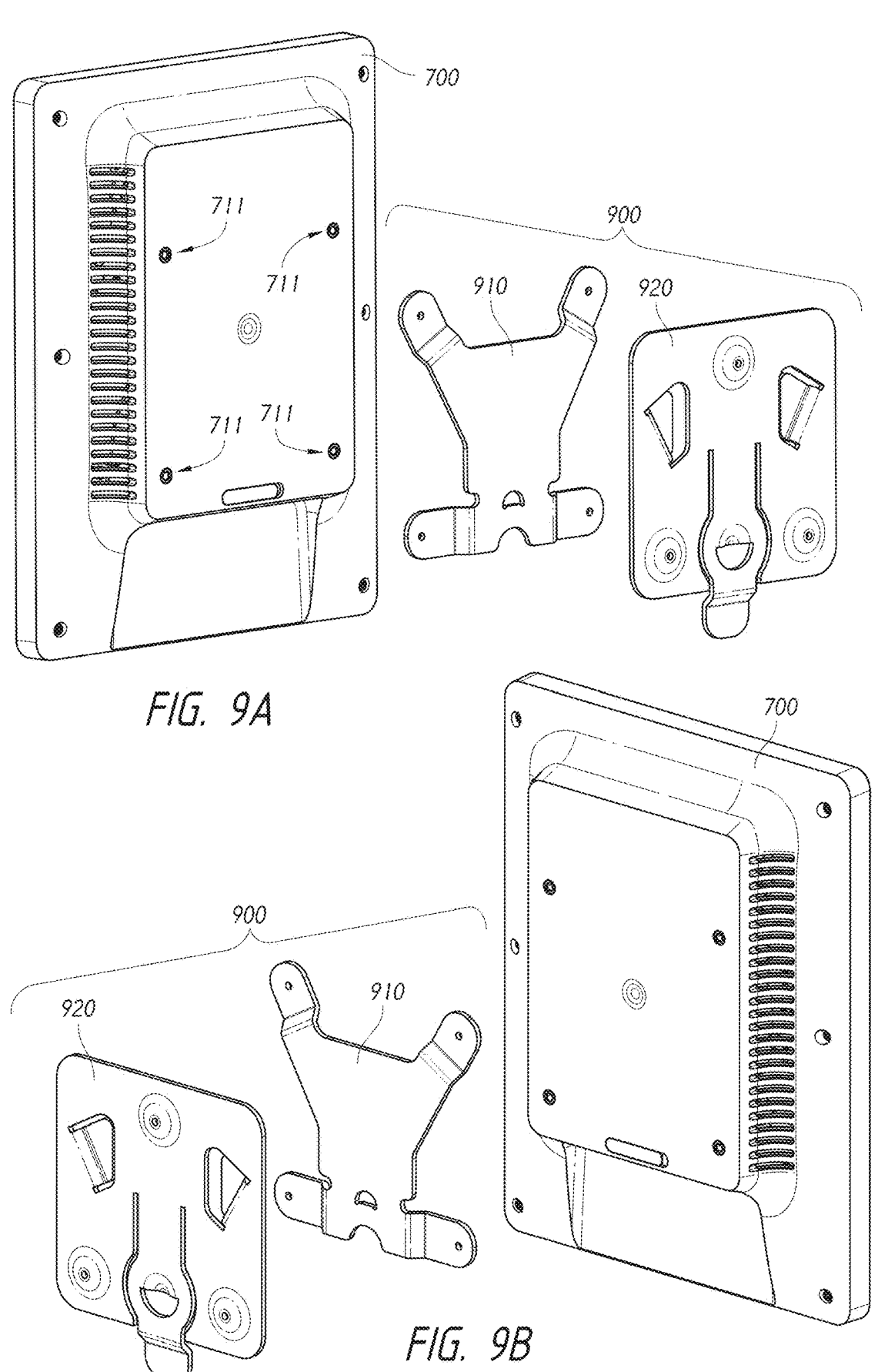
FIGS. 9A-9B illustrate the monitoring hub of FIG. 7A and a mounting assembly in accordance with aspects of this disclosure.
Figures 9C, 9D:
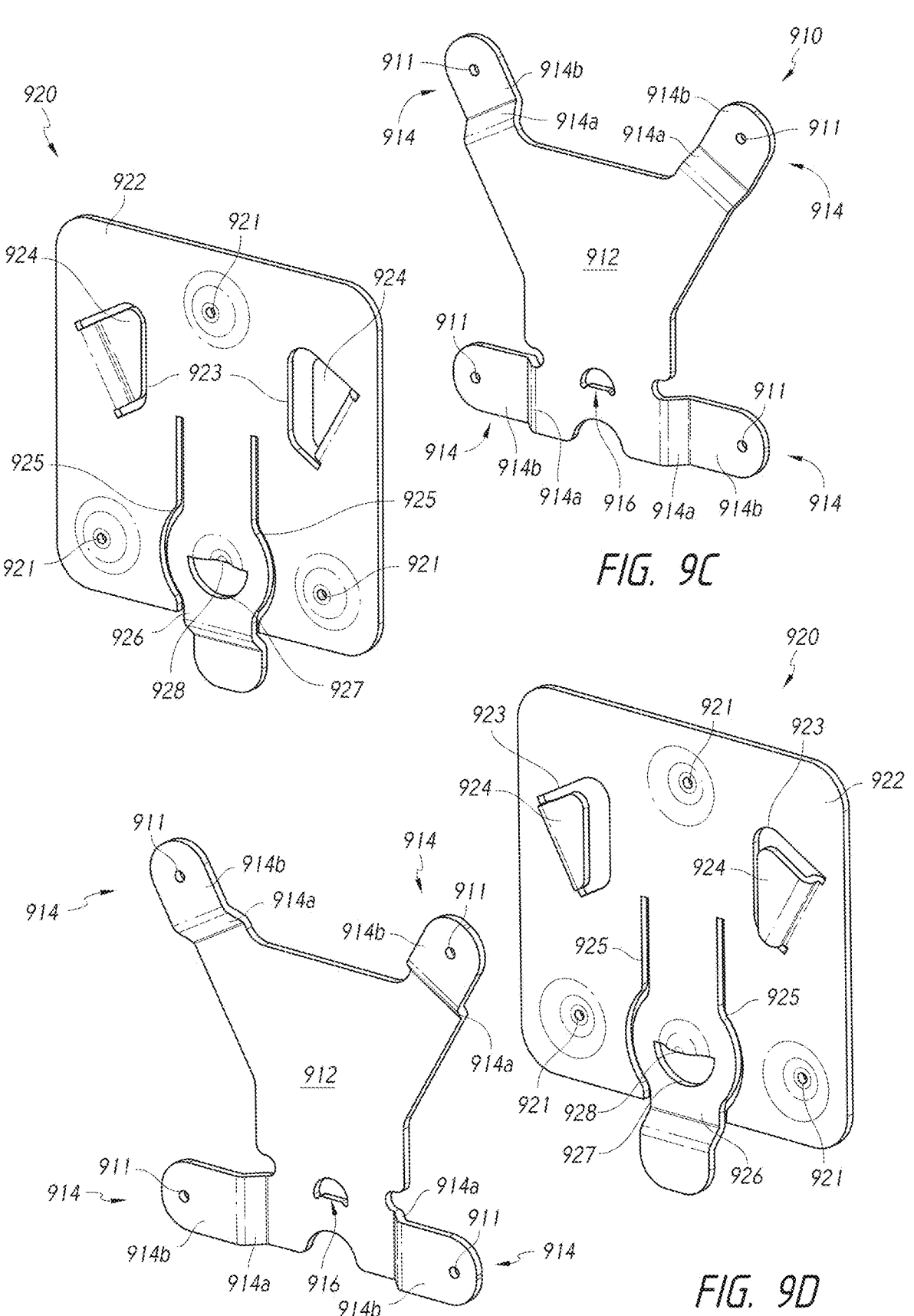
FIGS. 9C-9D illustrate the mounting assembly of FIGS. 9A-9B in accordance with aspects of this disclosure.
Figure 9E:
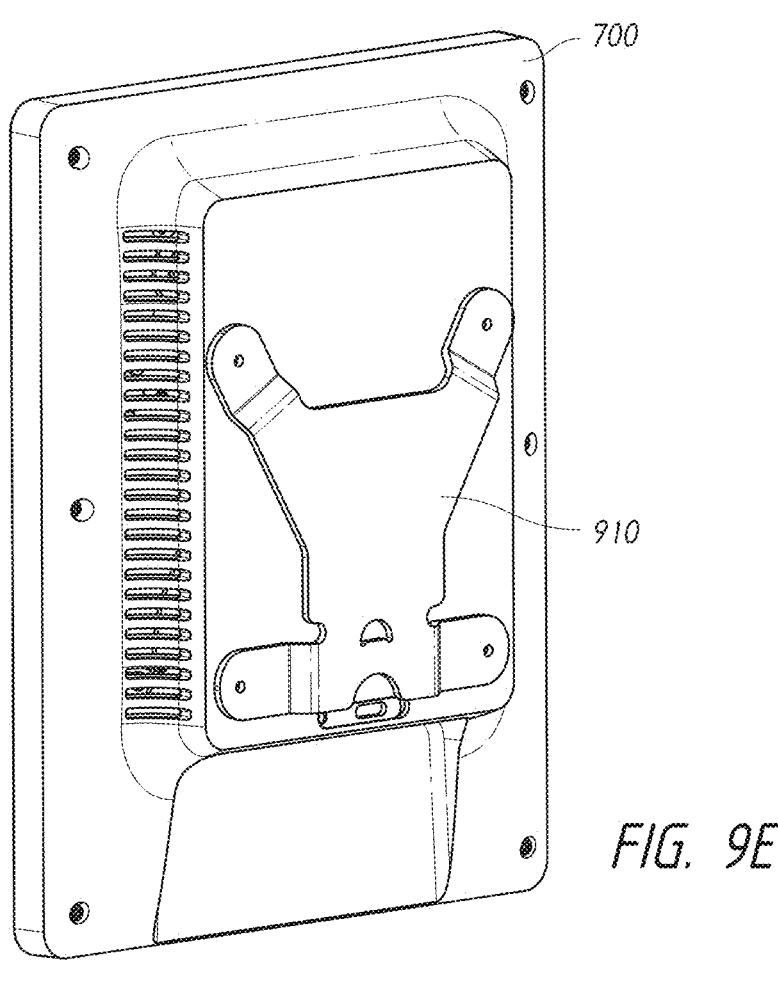
FIGS. 9E-9F illustrate rear perspective and rear views (respectively) of a mount of the mounting assembly of FIGS. 9A-9B connected to the monitoring hub of FIG. 7A in accordance with aspects of this disclosure.
Figure 9F:
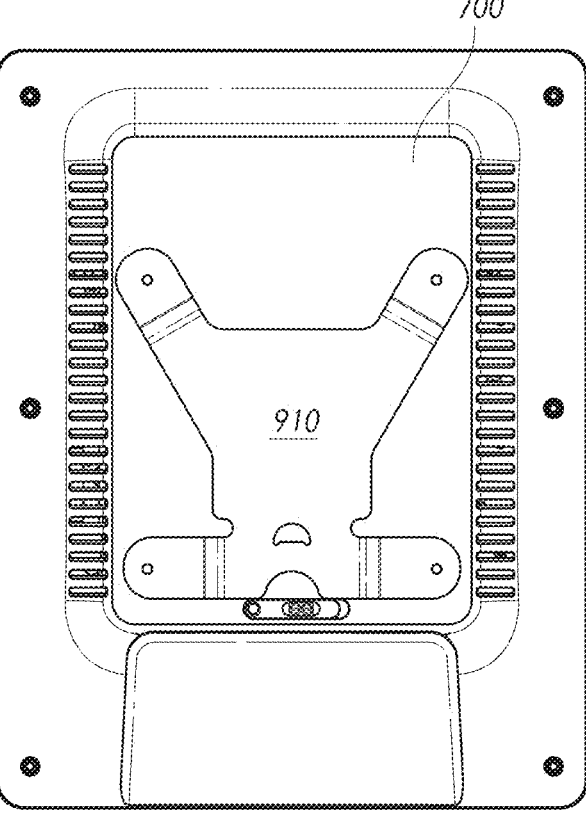
Figures 9G, 9H, 9I:
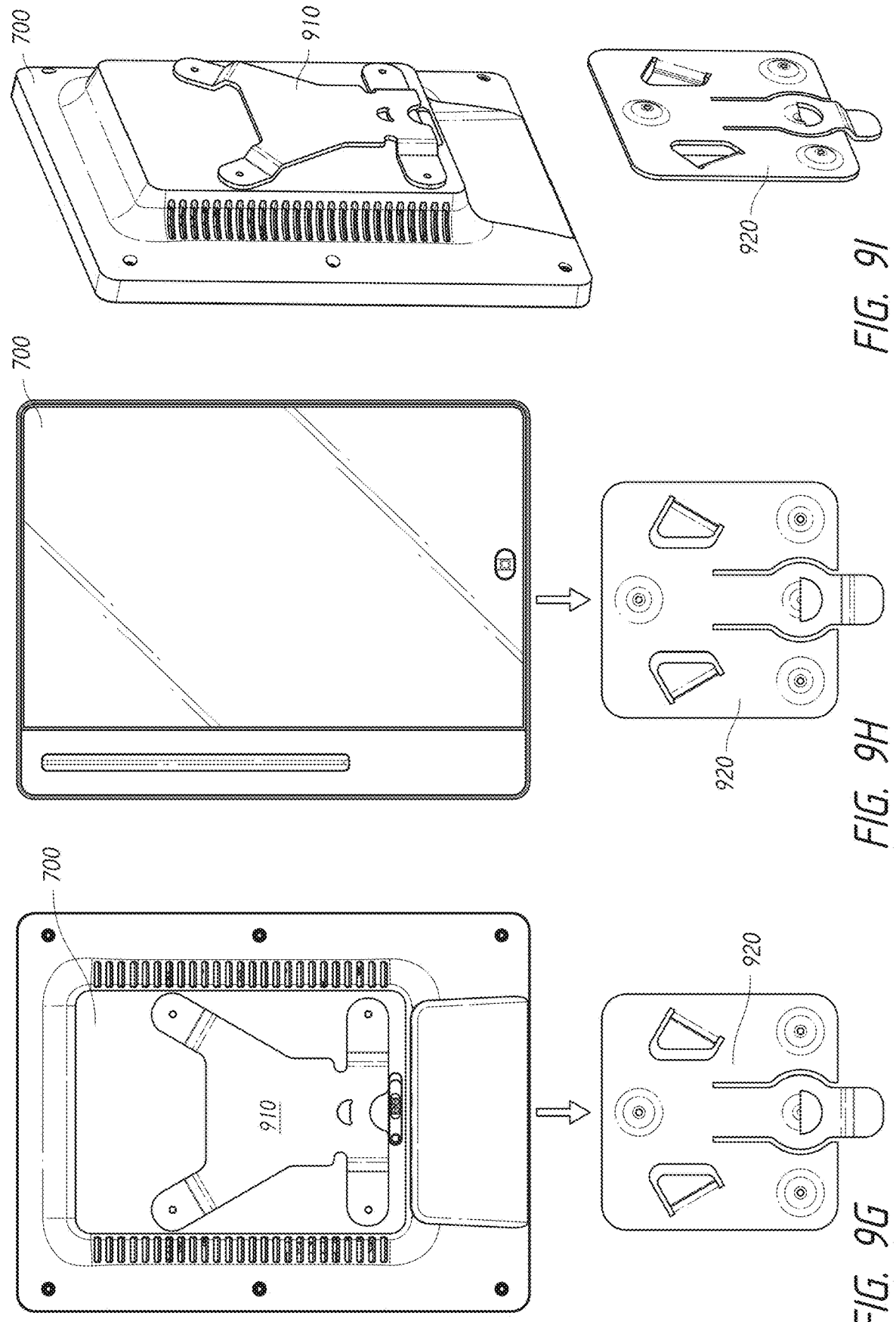
FIGS. 9G-9I illustrate how the monitoring hub and mounting assembly of FIGS. 9A-9B can be attached in accordance with aspects of this disclosure.
Figure 9J:
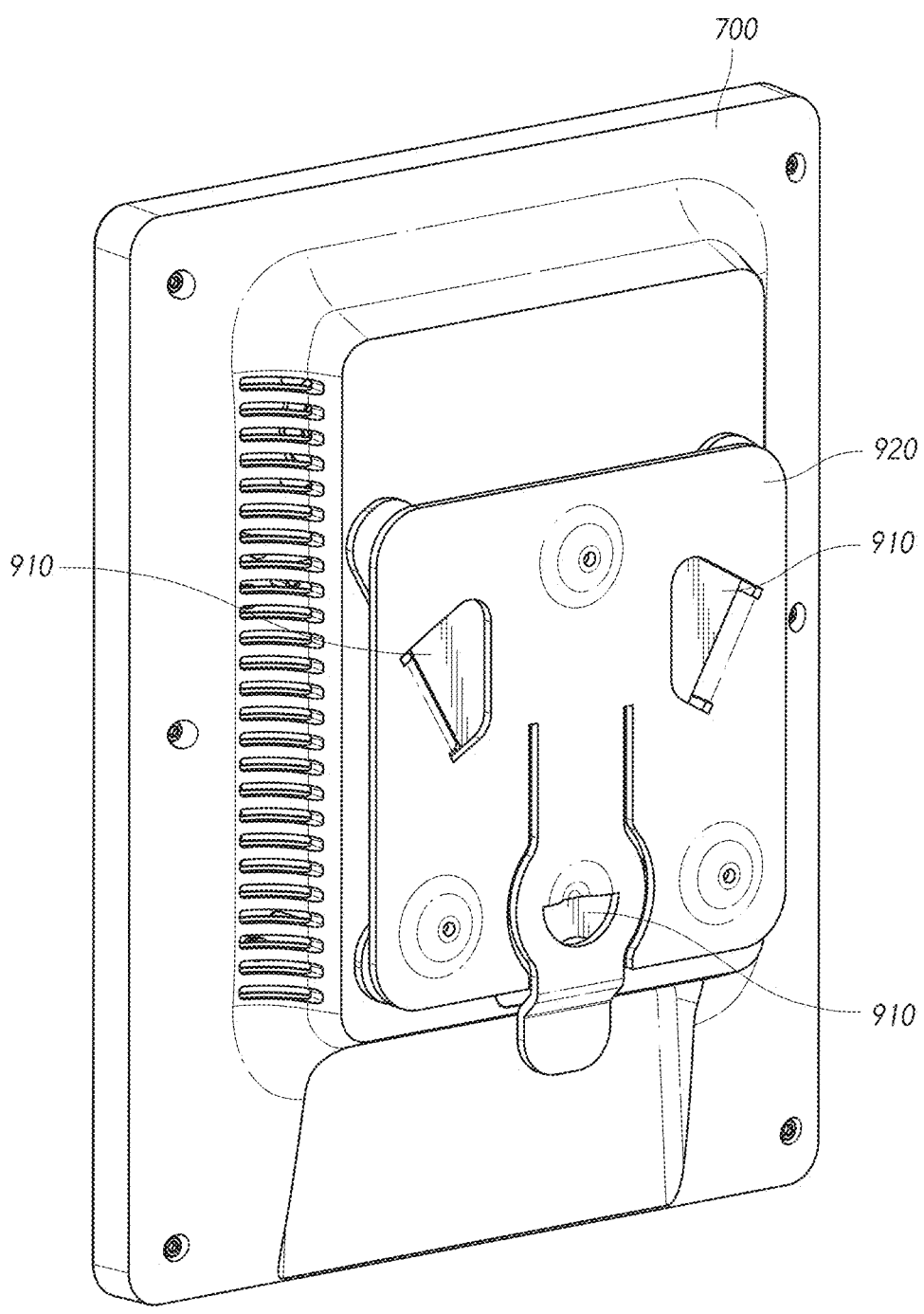
FIG. 9J illustrates the monitoring hub and mounting assembly of FIGS. 9A-9B attached together in accordance with aspects of this disclosure.

FIGS. 9C-9D illustrate rear and front (respectively) perspective views of mounts 910, 920 detached from one another. Mount 910 can include a base 912 (which may also be referred to as a "body" or "body portion") and one or more arms 914 extending outward from base 912. Where mount 910 includes a plurality of arms 914, such as is illustrated in the figures, such plurality of arms 914 can be separated and spaced from one another. In some implementations, mount 910 includes two arms at a first end of mount 910 and two additional arms at a second end of mount 910. In some implementations, as illustrated in the figures, arms 914 can each have a first portion 914a connected to base 912 and a second portion 914b connected to such first portion 914a and which is transverse relative to such first portion 924. This can allow base 912 to be spaced from a surface of hub 700 by a gap which is sized and/or shaped to allow fingers 924 of mount 920 to engage portions of base 912 and fit between base 912 and the hub 700 when mounts 910, 920 and hub 700 are attached together such that the second portion 914b is substantially parallel to base 912 (for example, a plane defined along base 912). Mount 910 can include one or more through-holes configured to accommodate fasteners (e.g., screws) to allow mount 910 to be secured to hub 700 (for example, via threaded holes 711 in hub 700). Such through-holes can be through-holes 911 located in arms 914. As shown in the figures, mount 910 can include an opening 916 that can interact with protrusion 928 of mount 920 as described in more detail below.

With continued reference to FIGS. 9C-9D, mount 920 can include a base 922 (which may also be referred to as a "body" or "body portion"). Mount 920 can further include one or more through-holes 921 configured to accommodate fasteners (e.g., screws) to allow mount 920 to be secured to a surface (for example, of a wall) and/or to another object (such as a wall-mounted support arm). In some implementations, portions of base 922 surrounding holes 921 are recessed with respect to a first surface of base 922 and/or protrude from a second, opposite surface of base 922. Such recessed portion can allow a fastener head to be hidden ("countersunk") and the protruding portions can provide more space between a mounting surface (for example, wall) which can in turn provide more space for a user to access lever 926 of mount 920 (to allow detachment of mounts 910, 920 from one another).

Mount 920 can include structure to allow mount 920 to removably attach to mount 910. For example, mount 920 can include one or more fingers 924 that can be configured to engage with portions of body 912. Finger(s) 924 can extend from base 922, for example, proximate openings 923. In some implementations, finger(s) 924 can be formed by cutting material from base 922 to form openings 923 and fingers 924. Fingers 924 can include a first portion that is connected and transverse to base 923 and a second portion that is transverse to such first portion, for example, such that the second portion of the fingers 924 is substantially parallel to base 922 (for example, a plane defined along base 922). Such second portion of the fingers 924 can be spaced from base 922 by a gap that is sized to receive portions of base 912 of mount 910.

Mount 920 can further include a lever 926. Lever 926 can be formed out of base 922 (for example, via cutting portions of base 922 to form opening 925) and/or connected to base 922. A first end of lever 926 (which may be referred to as a "connected end") can be connected to base 922 and a second end of lever 926 can be "free". Such "free" end of lever 926 can be operated (e.g., moved) by a user, which can allow for removal of mount 910 from mount 920 as described further below. Lever 926 can include a protrusion 928 configured to engage with an opening 916 in mount 910 and/or portions of base 912 proximate said opening 916. Lever 926 can be movable from a first position in which lever 926 engages a portion of mount 910 and a second position in which such engagement is removed. In some implementations, when lever 926 is in such first position, protrusion 928 of lever 926 engages portion(s) of base 912 proximate opening 916 and/or is at least partially positioned within and/or through opening 916. When protrusion 928 is positioned at least partially within and/or through opening 916 and/or contacts structure surrounding opening 916, the opening 916 and/or such surrounding structure can present a physical interference that inhibits (for example, prevents) mount 910 from detaching from mount 920. When lever 926 is moved to such second position, protrusion 928 can be removed from opening 916 and such physical interference can be removed, thereby allowing mount 910 to be detached from mount 920. In some implementations, lever 926 is biased such that as mount 910 is vertically inserted into mount 920 (for example, base 912 is inserted between fingers 924) protrusion 928 contacts a surface of base 912 and snaps into engagement with opening 916. As shown in at least FIGS.

9C-9D, in some implementations the "free" end of lever 926 (which may also be referred to as an "actuation end") is bent, for example, away from a surface or plane of a remaining portion of lever 926 and/or of base 922. Such implementation can advantageously provide more space for a user to access the lever 926 when mounts 910, 920 are attached to each other and/or to a surface (for example, a wall). In some implementations, protrusion 928 comprises a semi-circular shape. In some implementations, opening 927 comprises a semi-circular shape. In some implementations, opening 916 comprises a semi-circular shape. In some implementations, a portion of base 912 within opening 916 (for example, disposed along a straight side of a semi-circular shaped opening 916) is raised.

Figures 9K, 9L, 9M:
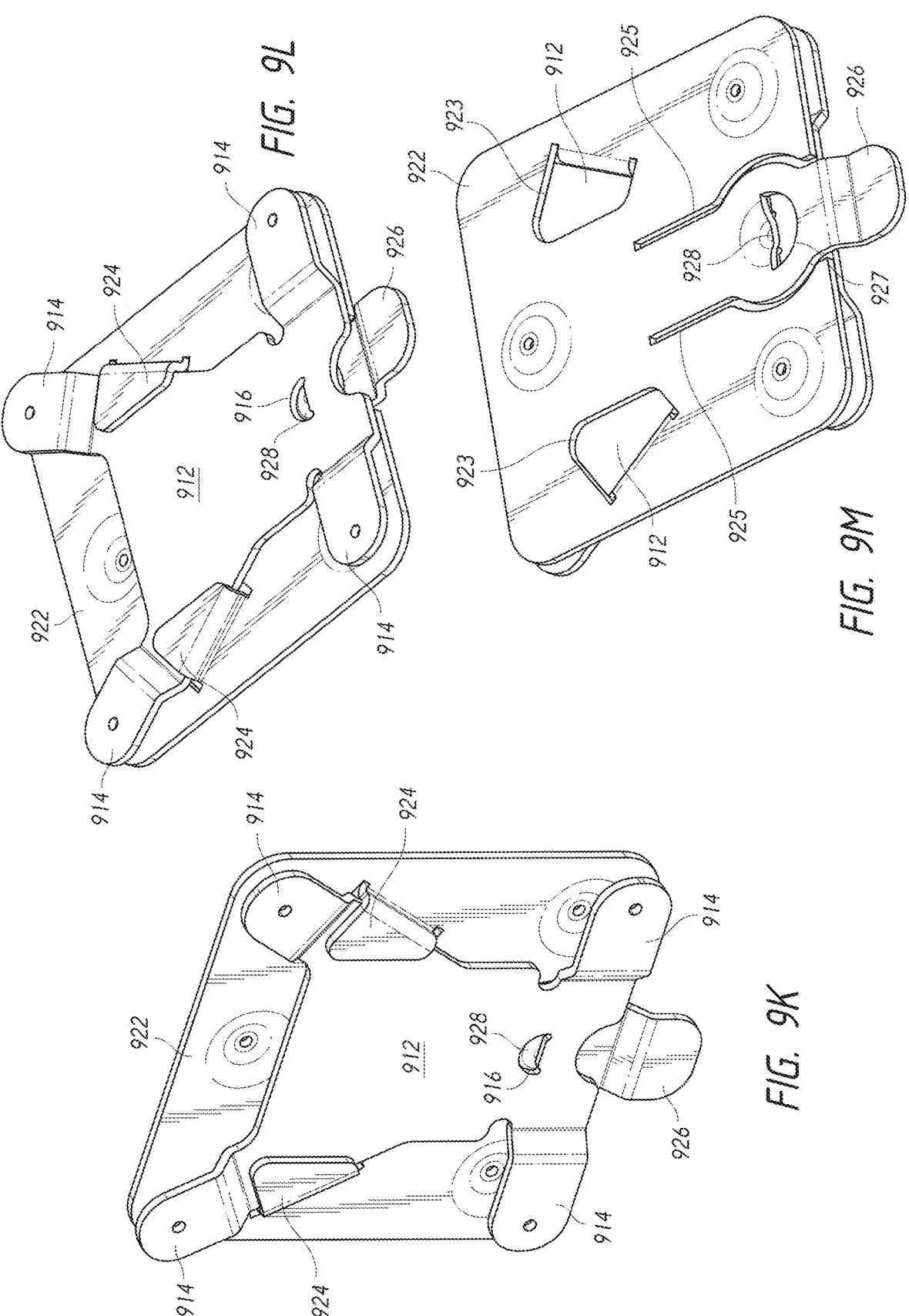
FIGS. 9K-9M illustrate the mounting assembly of FIGS. 9A-9B in an attached configuration without also showing a monitoring hub in accordance with aspects of this disclosure.

With continued reference to FIGS. 9C-9D, base 912 of mount 910 can have a width that tapers at least partially along a height thereof. For example, base 912 can have a width that is larger at or near a top end of mount 910 which tapers to a smaller width at or near a middle portion of mount 910 and/or a bottom end of mount 910 (given the orientation of FIGS. 9C-9D). As also shown in FIGS. 9C-9D, fingers 924 of mount 920 can be angled, for example, relative to vertical. Fingers 924 can form a pocket that can receive portion(s) of mount 910 (for example, base 912). In some implementations, fingers 924 form a funneled pocket configured to receive portion(s) of mount 910 (for example, base 912). Such configurations can advantageously allow mount 910 (which can be secured to hub 700) to be vertically secured to mount 912 by moving the base 912 downward within and/or between fingers 924, such that mounts 910, 920 can be connected as shown in FIGS. 9K-9M. It is noted that FIGS. 9K-9M illustrate mounts 910, 920 connected to one another without also showing hub 700 to more clearly illustrate how mounts 910, 920 can be positioned when secured to one another. In one example method: mount 910 is secured to hub 700, for example, via screws inserted through holes 911 in arms 914 (see FIGS. 9E-9F) and into threaded holes 711 in hub 700; mount 920 is secured to a wall or other object via screws inserted through holes 921; and hub 700 and mount 910 are secured to mount 920, for example, by vertically positioning base 912 within fingers 924 of mount 920. In some implementations, a portion of lever 926 can engage with a portion of mount 910 when mounts 910, 920 are connected to one another. For example, protrusion 928 can be positioned within opening 916 of mount 910 and/or can engage with structure surrounding opening 916. Such engagement of lever 926 with a portion of mount 910 can inhibit (for example, prevent) mounts 910, 920 from being disconnected from one another. When disconnection is desired, lever 926 can be actuated (for example, by moving a free end of lever 926 in a direction generally perpendicular to a surface or plane of base 922), which in turn can remove protrusion 928 from opening 916, thereby allowing mount 910 to be disconnected from mount 920. In some implementations, mount 910 is removed from mount 920 by moving mount 910 in a direction that is opposite to a direction that mount 910 was moved to insert mount 910 into mount 920. For example, in some implementations, mount 910 is connected to mount 920 by downwardly inserting mount 910 into mount 920 and mount 910 is disconnected from mount 920 by upwardly moving mount 910 relative to mount 920.

Figures 10A, 10B:
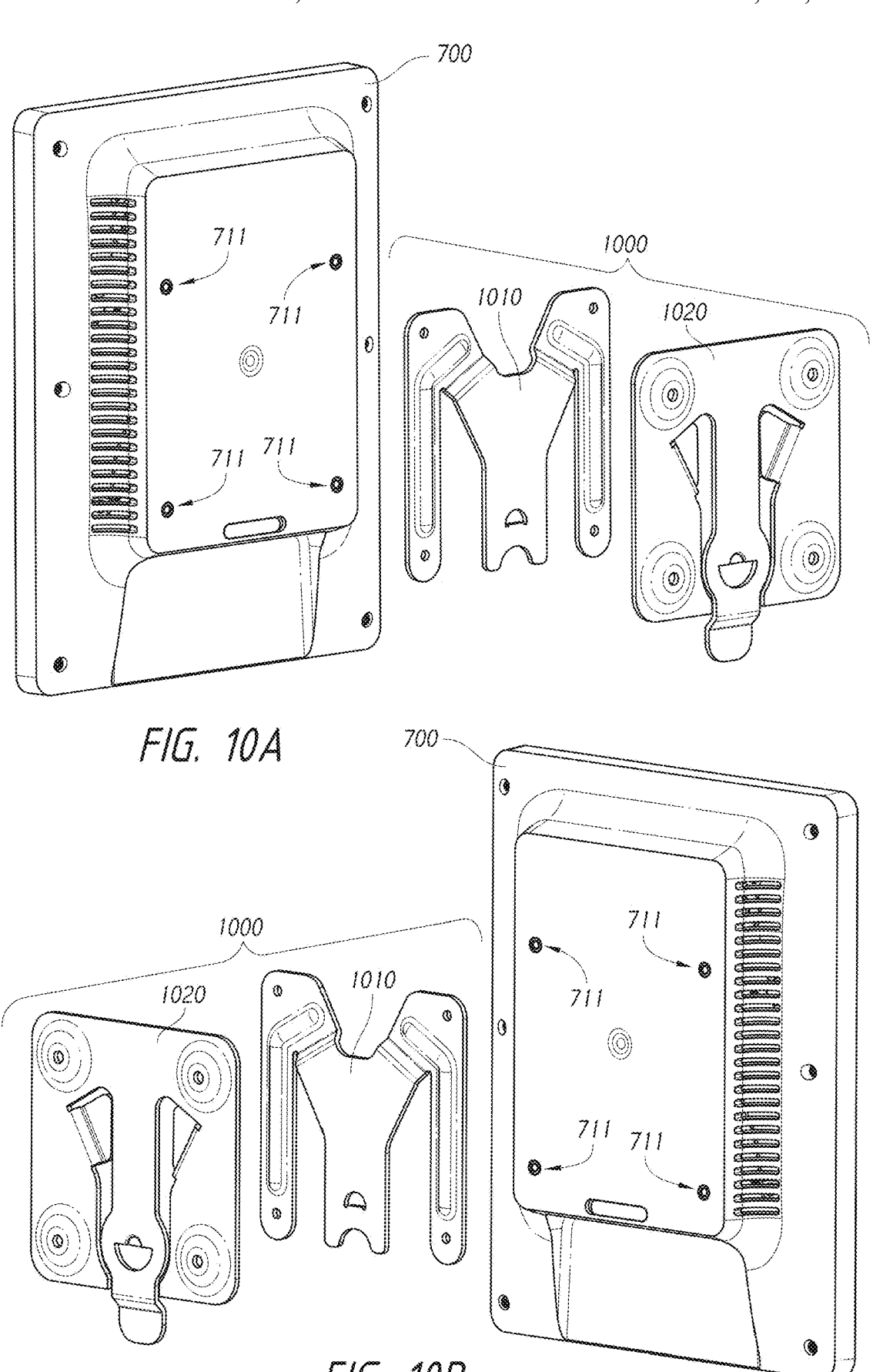
FIGS. 10A-10B illustrate the monitoring hub of FIG. 7A and another implementation of a mounting assembly in accordance with aspects of this disclosure.
Figure 10C:
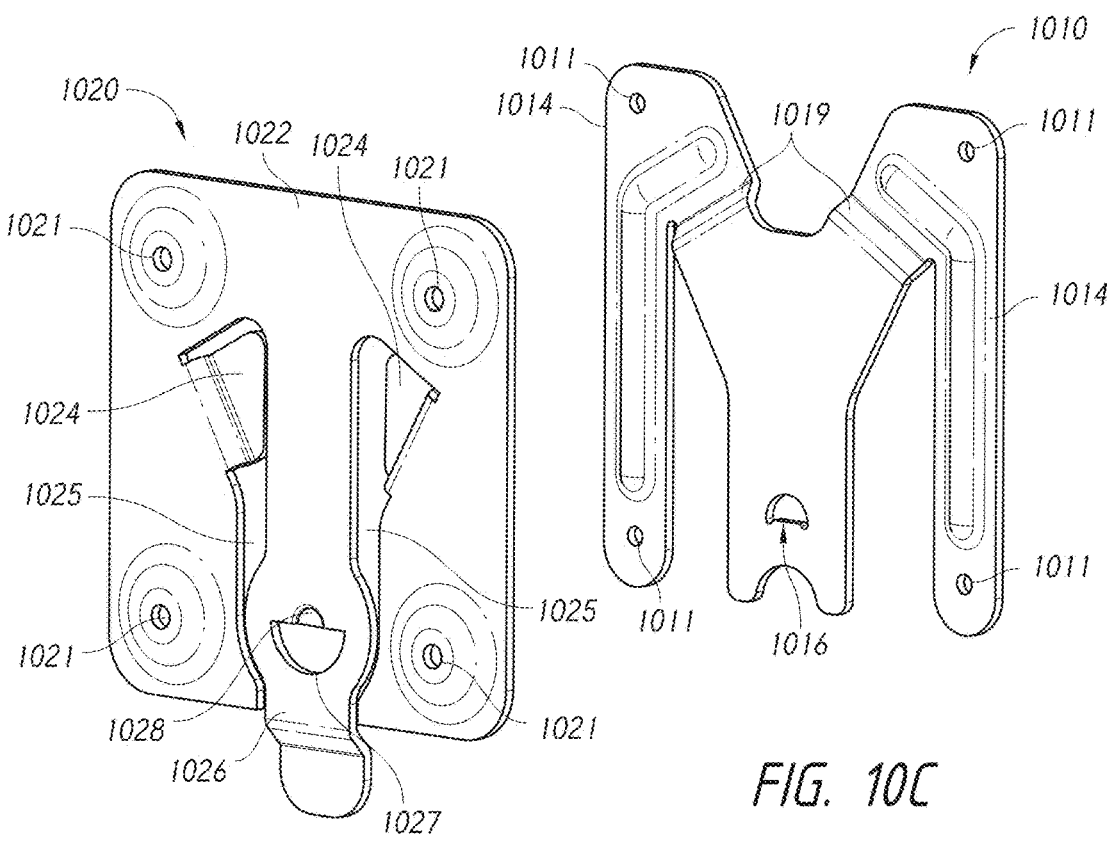
FIGS. 10C-10D illustrate the mounting assembly of FIGS. 10A-10B in accordance with aspects of this disclosure.
Figure 10D:
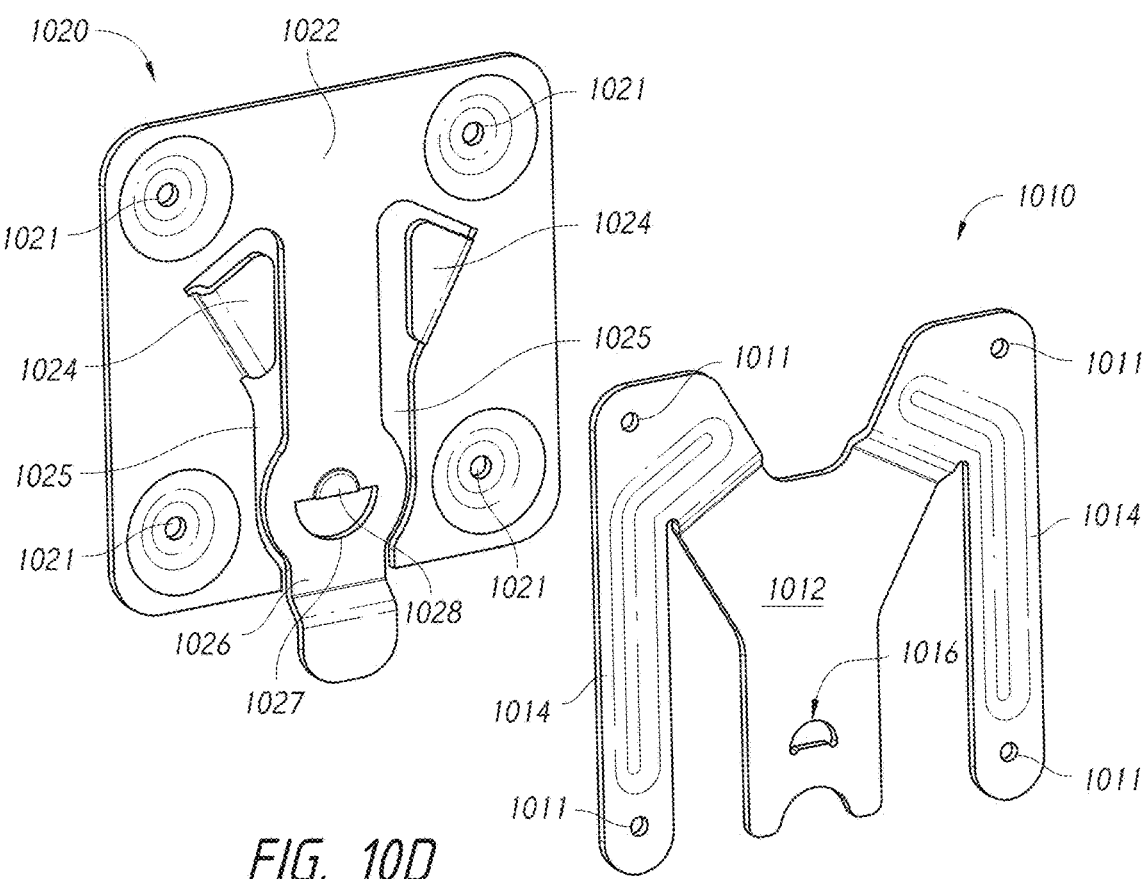
Figure 10E:
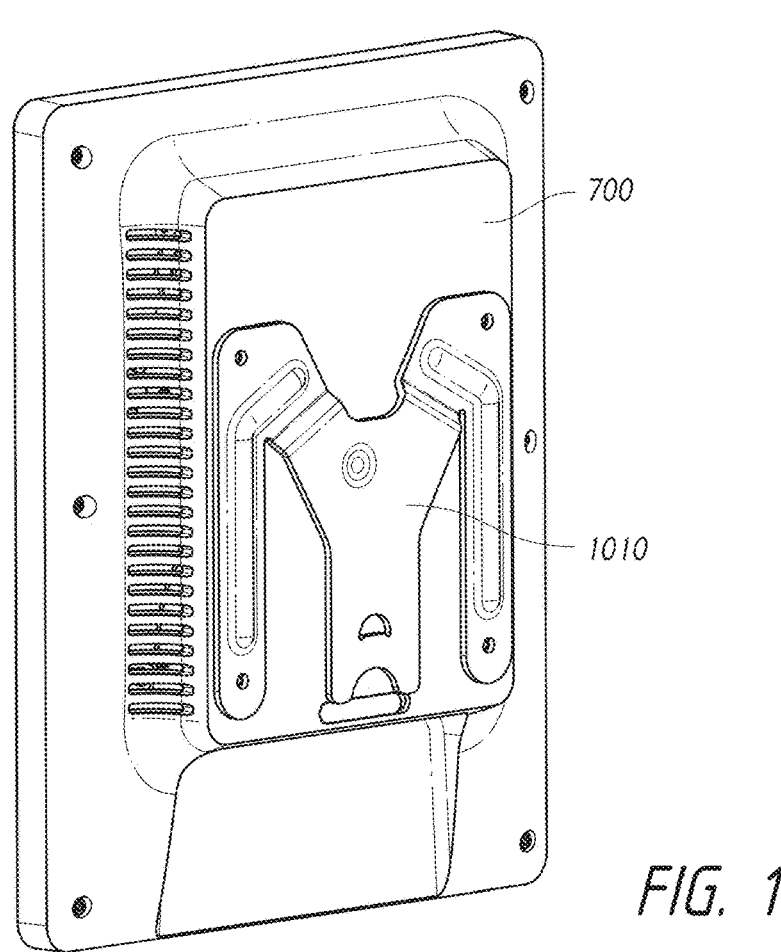
FIGS. 10E-10F illustrate rear perspective and rear views (respectively) of a mount of the mounting assembly of FIGS. 10A-10B connected to the monitoring hub of FIG. 7A in accordance with aspects of this disclosure.
Figure 10F:
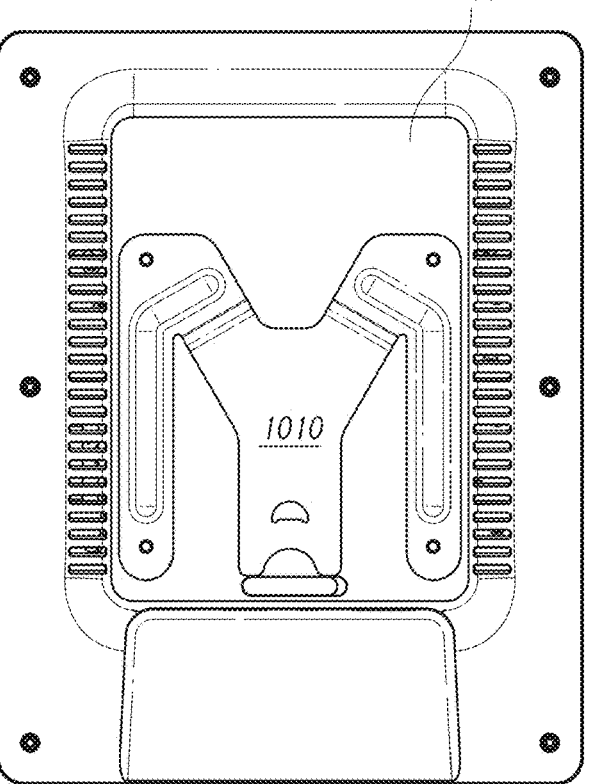
Figures 10G, 10H:
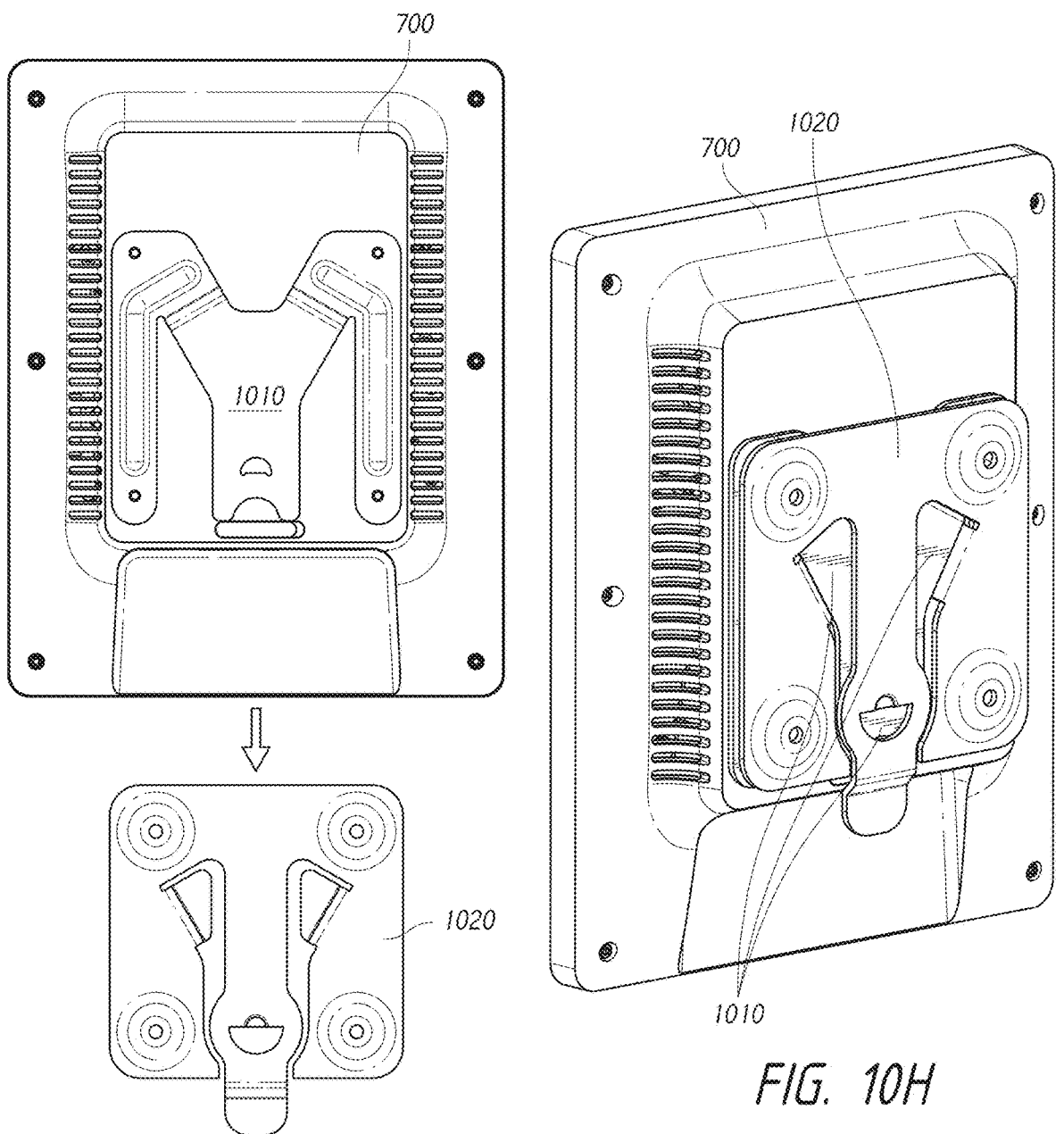
FIG. 10G illustrates how the monitoring hub and mounting assembly of FIGS. 10A-10B can be attached in accordance with aspects of this disclosure.
FIG. 10H illustrates the monitoring hub and mounting assembly of FIGS. 10A-10B attached together in accordance with aspects of this disclosure.

FIGS. 10A-10D illustrate another implementation of a mounting assembly 1000. Mounting assembly 1000 can include mounts 1010 and 1020. FIGS. 10C-10D illustrate rear and front (respectively) perspective views of mounts 1010, 1020 detached from one another. Mount 1010 can include a base 1012 (which may also be referred to as a "body" or "body portion") and one or more arms 1014 extending from and connecting to base 1012. In some implementations, mount 1010 includes two arms, portions of each of which are separated from a portion of base 1012 by openings (see FIGS. 10C-10D). In some implementations, as illustrated in the figures, a portion 1019 of arms 1014 is bent such that arms 1014 are spaced from base 1012 (for example, a plane along which arms 1014 extend is spaced from a plane extending along base 1012). Such implementation can allow base 1012 to be spaced from a surface of hub 700 by a gap which is sized and/or shaped to allow fingers 1024 of mount 1020 to engage portions of base 1012 and fit between base 1012 and the hub 700 when mounts 1010, 1020 and hub 700 are attached together.

Mount 1010 can include one or more through-holes configured to accommodate fasteners (e.g., screws) to allow mount 1010 to be secured to hub 700 (for example, via threaded holes 711 in hub 700). Such through-holes can be through-holes 1011 located in arms 1014, as shown. As shown in the figures, mount 1010 can include an opening 1016 that can interact with protrusion 1028 of mount 1020 as described in more detail below.

With continued reference to FIGS. 10C-10D, mount 1020 can include a base 1022 (which may also be referred to as a "body" or "body portion"). Mount 1020 can further include one or more through-holes 1021 configured to accommodate fasteners (e.g., screws) to allow mount 1010 to be secured to a surface (for example, of a wall) and/or to another object (such as a wall-mounted support arm). In some implementations, portions of base 1022 surrounding holes 1021 are recessed with respect to a first surface of base 1022 and/or protrude from a second, opposite surface of base 1022. Such recessed portion can allow a fastener head to be hidden ("countersunk") and the protruding portions can provide more space between a mounting surface (for example, wall) which can in turn provide more space for a user to access lever 1026 of mount 1020 (to allow detachment of mounts 1010, 1020 from one another).

Mount 1020 can include structure to allow mount 1010 to removably attach to mount 1020. For example, mount 1020 can include one or more fingers 1024 that can be configured to engage with portions of body 1012. Finger(s) 1024 can extend from base 1022, for example, at opening 1025. In some implementations, finger(s) 1024 can be formed by cutting material from base 1022 to form opening 1025 and fingers 1024. Fingers 1024 can include a first portion that is connected and transverse to base 1022 and a second portion that is transverse to such first portion, for example, such that the second portion of the fingers 1024 is substantially parallel to base 1022 (for example, a plane defined along base 1022). Such second portion of the fingers 1024 can be spaced from base 1022 by a gap that is sized to receive portions of base 1012 of mount 1010.

Mount 1020 can further include a lever 1026. Lever 1026 can be formed out of base 1022 (for example, via cutting portions of base 1022 to form opening 1025) and/or connected to base 1022. A first end of lever 1026 (which may be referred to as a "connected end") can be connected to base 1022 and a second end of lever 1026 can be "free". Such "free" end of lever 1026 can be operated (e.g., moved) by a user, which can allow for removal of mount 1010 from mount 1020 as described further below. Lever 1026 can include a protrusion 1028 configured to engage with an opening 1016 in mount 1010 and/or portions of base 1012 proximate said opening 1016. Lever 1026 can be movable from a first position in which lever 1026 engages a portion of mount 1010 to a second position in which such engagement is removed. In some implementations, when lever 1026 is in such first position, protrusion 1028 of lever 1026 engages portion(s) of base 1012 proximate opening 1016 and/or is at least partially positioned within and/or through opening 1016. When protrusion 1028 is positioned at least partially within and/or through opening 1016 and/or contacts structure surrounding opening 1016, the opening 1016 and/or such surrounding structure can present a physical interference that inhibits (for example, prevents) mount 1010 from detaching from mount 1020. When lever 1026 is moved to such second position, protrusion 1028 can be removed from opening 1016 and such physical interference can be removed, thereby allowing mount 1010 to be detached from mount 1020. In some implementations, lever 1026 is biased such that as mount 1010 is vertically inserted into mount 1020 (for example, base 1012 is inserted between fingers 1024) protrusion 1028 contacts a surface of base 1012 and snaps into engagement with opening 1016. As shown in at least FIGS. 10C-10D, in some implementations the "free" end of lever 1026 (which may also be referred to as an "actuation end") is bent, for example, away from a surface or plane of a remaining portion of lever 1026 and/or of base 1022. Such implementation can advantageously provide more space for a user to access the lever 1026 when mounts 1010, 1020 are attached to each other and/or to a surface (for example, a wall). In some implementations, protrusion 1028 comprises a semi-circular shape. In some implementations, opening 1027 comprises a semi-circular shape. In some implementations, opening 1016 comprises a semi-circular shape. In some implementations, a portion of base 1012 within opening 1016 (for example, disposed along a straight side of a semi-circular shaped opening 1016) is raised.

Figures 10I, 10J, 10K:
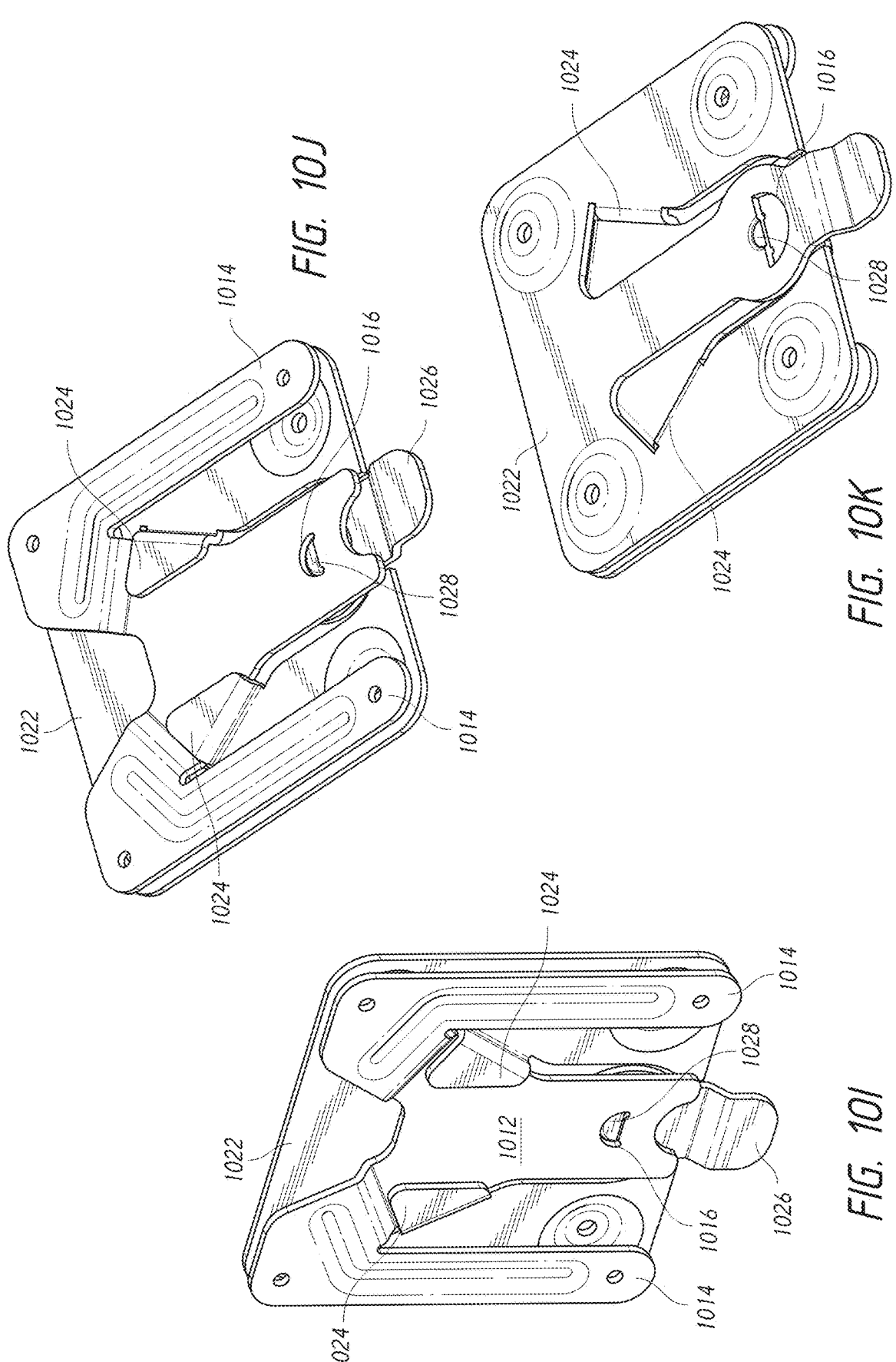
FIGS. 10I-10K illustrate the mounting assembly of FIGS. 10A-10B in an attached configuration without also showing a monitoring hub in accordance with aspects of this disclosure.

With continued reference to FIGS. 10C-10D, base 1012 of mount 1010 can have a width that tapers at least partially along a height thereof. For example, base 1012 can have a width that is larger at or near a top end of base 1012 which tapers to a smaller width at or near a middle portion of base 1012 and/or a bottom end of base 1012 (given the orientation of FIGS. As also shown in FIGS. 10C-10D, fingers 1024 of mount 1020 can be angled, for example, relative to vertical. Fingers 1024 can form a pocket that can receive portion(s) of mount 1010 (for example, base 1012). In some implementations, fingers 1024 form a funneled pocket configured to receive portion(s) of mount 1010 (for example, base 1012). Such configurations can advantageously allow mount 1010 (which can be secured to hub 700) to be vertically secured to mount 1002 by moving the base 1012 downward within and/or between fingers 1024, such that mounts 1010, 1020 can be connected as shown in FIGS. 10G-10K. It is noted that FIGS. 10I-10K illustrate mounts 1010, 1020 connected to one another without also showing hub 700 to more clearly illustrate how mounts 1010, 1020 can be positioned when secured to one another.

In one example method: mount 1010 is secured to hub 700, for example, via screws inserted through holes 1011 in arms 1014 (see FIGS. 10E-10F) and into threaded holes 711 in hub 700; mount 1020 is secured to a wall or other object via screws inserted through holes 1021; and hub 700 and mount 1010 are secured to mount 1020, for example, by vertically positioning base 1012 within fingers 1024 of mount 1020. In some implementations, a portion of lever 1026 can engage with a portion of mount 1010 when mounts 1010, 1020 are connected to one another. For example, protrusion 1028 can be positioned within opening 1016 of mount 1010 and/or can engage with structure surrounding opening 1016. Such engagement of lever 1026 with a portion of mount 1010 can inhibit (for example, prevent) mounts 1010, 1020 from being disconnected from one another. When disconnection is desired, lever 1026 can be actuated (for example, by moving a free end of lever 1026 in a direction generally perpendicular to a surface or plane of base 1022), which in turn can remove protrusion 1028 from opening 1016, thereby allowing mount 1010 to be disconnected from mount 1020. In some implementations, mount 1010 is removed from mount 1020 by moving mount 1010 in a direction that is opposite to a direction that mount 1010 was moved to insert mount 1010 into mount 1020. For example, in some implementations, mount 1010 is connected to mount 1020 by downwardly inserting mount 1010 into mount 1020, and mount 1010 is disconnected from mount 1020 by upwardly moving mount 1010 relative to mount 1020.

Although certain implementations of mounts 920, 1020 are described above as including levers 926, 1026, in some variants, mounts 920, 1020 do not includes levers 926, 1026. In such variants, mounts 920, 1020 can connect to and support mounts 910, 1010 (respectively), which can in turn be connected to hub 700. In some of such variants, mounts 910, 1010 can be supported (for example, vertically) by mounts 920, 1020 (respectively) but can allow mounts 910, 1010 to be removed (for example, by upward vertical movement or otherwise moved in an opposite direction as a direction in which the mounts were inserted/connected) without requiring an additional step to be taken (for example, "unlocking" of a lever). Additionally, while fingers 924, 1024 of mounts 920, 1020 are described as being angled and base 912, 1012 of mounts 910, 1010 are described as having tapered widths (at least for a portion of a height thereof), alternative implementations are possible that still allow base 912, 1012 to be received and/or supported by fingers 924, 1024 (for example, vertically supported). For example, in some variants, fingers 924, 1024 can form a pocket sized and/or shaped to receive and/or support base 912, 1012.

In some variants, mount 910 is integral with monitoring hub 700 (for example, is integrally formed into a housing of hub 700). In some variants, mount 1010 is integral with monitoring hub 700 (for example, is integrally formed into a housing of hub 700).

ADDITIONAL IMPLEMENTATIONS

As used herein, "real-time" or "substantial real-time" may refer to events (e.g., receiving, processing, transmitting, displaying etc.) that occur at the same time or substantially the same time (e.g., neglecting any small delays such as those that are imperceptible and/or inconsequential to humans such as delays arising from electrical conduction or transmission). As a non-limiting example, "real-time" may refer to events that occur within a time frame of each other that is on the order of milliseconds, seconds, tens of seconds, or minutes. For example, "real-time" may refer to events that occur within a time frame of less than 1 minute, less than 30 seconds, less than 10 seconds, less than 1 second, less than 0.05 seconds, less than 0.01 seconds, less than 0.005 seconds, less than 0.001 seconds, etc. In some implementations, "real-time" may refer to events that occur at a same time as, or during, another event.

As used herein, "system," "instrument," "apparatus," and "device" generally encompass both the hardware (for example, mechanical and electronic) and, in some implementations, associated software (for example, specialized computer programs for graphics control) components.

It is to be understood that not necessarily all objects or advantages may be achieved in accordance with any particular implementation described herein. Thus, for example, those skilled in the art will recognize that certain implementations may be configured to operate in a manner that achieves or optimizes one advantage or group of advantages as taught herein without necessarily achieving other objects or advantages as may be taught or suggested herein.

Each of the processes, methods, and algorithms described in the preceding sections may be embodied in, and fully or partially automated by, code modules executed by one or more computer systems or computer processors including computer hardware. The code modules may be stored on any type of non-transitory computer-readable medium or computer storage component, such as hard drives, solid state memory, optical disc, and/or the like. The systems and modules may also be transmitted as generated data signals (for example, as part of a carrier wave or other analog or digital propagated signal) on a variety of computer-readable transmission mediums, including wireless-based and wired/cable-based mediums, and may take a variety of forms (for example, as part of a single or multiplexed analog signal, or as multiple discrete digital packets or frames). The processes and algorithms may be implemented partially or wholly in application-specific circuitry. The results of the disclosed processes and process steps may be stored, persistently or otherwise, in any type of non-transitory computer storage such as, for example, volatile or non-volatile storage.

Many other variations than those described herein will be apparent from this disclosure. For example, depending on the implementation, certain acts, events, or functions of any of the algorithms described herein can be performed in a different sequence, can be added, merged, or left out altogether (for example, not all described acts or events are necessary for the practice of the algorithms). Moreover, in certain implementations, acts or events can be performed concurrently, for example, through multi-threaded processing, interrupt processing, or multiple processors or processor cores or on other parallel architectures, rather than sequentially. In addition, different tasks or processes can be performed by different machines and/or computing systems that can function together.

The various illustrative logical blocks, modules, and algorithm elements described in connection with the implementations disclosed herein can be implemented as electronic hardware, computer software, or combinations of both. To clearly illustrate this interchangeability of hardware and software, various illustrative components, blocks, modules, and elements have been described herein generally in terms of their functionality. Whether such functionality is implemented as hardware or software depends upon the particular application and design constraints imposed on the overall system. The described functionality can be implemented in varying ways for each particular application, but such implementation decisions should not be interpreted as causing a departure from the scope of the disclosure.

The various features and processes described herein may be used independently of one another, or may be combined in various ways. All possible combinations and sub-combinations are intended to fall within the scope of this disclosure. In addition, certain method or process blocks may be omitted in some implementations. The methods and processes described herein are also not limited to any particular sequence, and the blocks or states relating thereto can be performed in other sequences that are appropriate. For example, described blocks or states may be performed in an order other than that specifically disclosed, or multiple blocks or states may be combined in a single block or state. The example blocks or states may be performed in serial, in parallel, or in some other manner. Blocks or states may be added to or removed from the disclosed example implementations. The example systems and components described herein may be configured differently than described. For example, elements may be added to, removed from, or rearranged compared to the disclosed example implementations.

The various illustrative logical blocks and modules described in connection with the implementations disclosed herein can be implemented or performed by a machine, such as a general purpose processor, a digital signal processor ("DSP"), an application specific integrated circuit ("ASIC"), a field programmable gate array ("FPGA") or other programmable logic device, discrete gate or transistor logic, discrete hardware components, or any combination thereof designed to perform the functions described herein. A general purpose processor can be a microprocessor, but in the alternative, the processor can be a controller, microcontroller, or state machine, combinations of the same, or the like. A processor can include electrical circuitry configured to process computer-executable instructions. In another implementation, a processor includes an FPGA or other programmable devices that performs logic operations without processing computer-executable instructions. A processor can also be implemented as a combination of computing devices, for example, a combination of a DSP and a microprocessor, a plurality of microprocessors, one or more microprocessors in conjunction with a DSP core, or any other such configuration. Although described herein primarily with respect to digital technology, a processor may also include primarily analog components. For example, some, or all, of the signal processing algorithms described herein may be implemented in analog circuitry or mixed analog and digital circuitry. A computing environment can include any type of computer system, including, but not limited to, a computer system based on a microprocessor, a mainframe computer, a digital signal processor, a portable computing device, a device controller, or a computational engine within an appliance, to name a few.

The elements of a method, process, or algorithm described in connection with the implementations disclosed herein can be embodied directly in hardware, in a software module stored in one or more memory devices and executed by one or more processors, or in a combination of the two. A software module can reside in RAM memory, flash memory, ROM memory, EPROM memory, EEPROM memory, registers, hard disk, a removable disk, a CD-ROM, or any other form of non-transitory computer-readable storage medium, media, or physical computer storage known in the art. An example storage medium can be coupled to the processor such that the processor can read information from, and write information to, the storage medium. In the alternative, the storage medium can be integral to the processor. The storage medium can be volatile or nonvolatile. The processor and the storage medium can reside in an ASIC. The ASIC can reside in a user terminal. In the alternative, the processor and the storage medium can reside as discrete components in a user terminal.

Conditional language, such as, among others, "can," "could," "might," or "may," unless specifically stated otherwise, or otherwise understood within the context as used, is generally intended to convey that certain implementations include, while other implementations do not include, certain features, elements and/or steps. Thus, such conditional language is not generally intended to imply that features, elements and/or steps are in any way required for one or more implementations or that one or more implementations necessarily include logic for deciding, with or without user input or prompting, whether these features, elements and/or steps are included or are to be performed in any particular implementation.

Disjunctive language such as the phrase "at least one of X, Y, or Z," unless specifically stated otherwise, is otherwise understood with the context as used in general to present that an item, term, and so forth, may be either X, Y, or Z, or any combination thereof (for example, X, Y, and/or Z). Thus, such disjunctive language is not generally intended to, and should not, imply that certain implementations require at least one of X, at least one of Y, or at least one of Z to each be present.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain implementations, the terms "generally parallel" and "substantially parallel" refer to a value, amount, or characteristic that departs from exactly parallel by less than or equal to 10 degrees, 5 degrees, 3 degrees, or 1 degree. As another example, in certain implementations, the terms "generally perpendicular" and "substantially perpendicular" refer to a value, amount, or characteristic that departs from exactly perpendicular by less than or equal to 10 degrees, 5 degrees, 3 degrees, or 1 degree.

Any process descriptions, elements, or blocks in the flow diagrams described herein and/or depicted in the attached figures should be understood as potentially representing modules, segments, or portions of code which include one or more executable instructions for implementing specific logical functions or steps in the process. Alternate implementations are included within the scope of the implementations described herein in which elements or functions may be deleted, executed out of order from that shown or discussed, including substantially concurrently or in reverse order, depending on the functionality involved, as would be understood by those skilled in the art.

Unless otherwise explicitly stated, articles such as "a" or "an" should generally be interpreted to include one or more described items. Accordingly, phrases such as "a device configured to" are intended to include one or more recited devices. Such one or more recited devices can also be collectively configured to carry out the stated recitations. For example, "a processor configured to carry out recitations A, B and C" can include a first processor configured to carry out recitation A working in conjunction with a second processor configured to carry out recitations B and C.

All of the methods and processes described herein may be embodied in, and partially or fully automated via, software code modules executed by one or more general purpose computers. For example, the methods described herein may be performed by the computing system and/or any other suitable computing device. The methods may be executed on the computing devices in response to execution of software instructions or other executable code read from a tangible computer readable medium. A tangible computer readable medium is a data storage device that can store data that is readable by a computer system. Examples of computer readable mediums include read-only memory, random-access memory, other volatile or non-volatile memory devices, CD-ROMs, magnetic tape, flash drives, and optical data storage devices.

It should be emphasized that many variations and modifications may be made to the herein-described implementations, the elements of which are to be understood as being among other acceptable examples. All such modifications and variations are intended to be included herein within the scope of this disclosure. The section headings used herein are merely provided to enhance readability and are not intended to limit the scope of the implementations disclosed in a particular section to the features or elements disclosed in that section. The foregoing description details certain implementations. It will be appreciated, however, that no matter how detailed the foregoing appears in text, the systems and methods can be practiced in many ways. As is also stated herein, it should be noted that the use of particular terminology when describing certain features or aspects of the systems and methods should not be taken to imply that the terminology is being re-defined herein to be restricted to including any specific characteristics of the features or aspects of the systems and methods with which that terminology is associated.

Those of skill in the art would understand that information, messages, and signals may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

What is claimed is:

1. A monitoring hub configured to monitor a health status of a subject having a wireless physiological sensor, the monitoring hub comprising:

one or more hardware computer processors configured to execute a plurality of computer executable instructions to cause the monitoring hub to:

responsive to a request to establish wireless monitoring of a subject's physiology at the monitoring hub:

access wireless configuration data governing wireless communication with a wireless physiological sensor on a subject, said wireless configuration data comprising at least one or more device addresses associated with the wireless physiological sensor, said wireless configuration data received at the monitoring hub from a remote server;

based on at least the wireless configuration data, establish wireless communication between the monitoring hub and the wireless physiological sensor to cause the monitoring hub to wirelessly receive real-time physiological data from the wireless physiological sensor using one or more wireless communication protocols;

receive historical physiological data from the remote server, the historical physiological data comprising physiological data collected by the wireless physiological sensor before establishing the wireless communication between the monitoring hub and the wireless physiological sensor, the historical physiological data comprising physiological data communicated from the wireless physiological sensor to another monitoring hub an electronic device before establishing the wireless communication between the monitoring hub and the wireless physiological sensor; and generate user interface data for rendering a user interface including the real-time physiological data in combination with the historical physiological data to reduce a gap in monitoring between the historical physiological data and the real-time physiological data.

2. The monitoring hub of claim 1, wherein the one or more hardware computer processors is further configured to execute the plurality of computer executable instructions to cause the monitoring hub to establish said wireless communication between the monitoring hub and the wireless physiological sensor by establishing a Bluetooth connection between the monitoring hub and the wireless physiological sensor.

3. The monitoring hub of claim 1, wherein the one or more hardware computer processors is further configured to execute the plurality of computer executable instructions to cause the monitoring hub to establish said wireless communication between the monitoring hub and the wireless physiological sensor by establishing said wireless communication without implementing a Bluetooth pairing process.

4. The monitoring hub of claim 1, wherein the one or more hardware computer processors is further configured to execute the plurality of computer executable instructions to cause the monitoring hub to establish said wireless communication between the monitoring hub and the wireless physiological sensor in response to a user input, the user input comprising a non-contact user input.

5. The monitoring hub of claim 1, wherein the one or more hardware computer processors is further configured to execute the plurality of computer executable instructions to cause the monitoring hub to:

receive identification data via the monitoring hub using one or more of near field communication (NFC) or radio frequency identification (RFID), the identification data associated with a user requesting to establish wireless monitoring with the monitoring hub; and determine, based on at least the identification data, that the user has permission to establish the wireless monitoring.

6. The monitoring hub of claim 1, wherein the one or more hardware computer processors is further configured to execute the plurality of computer executable instructions to cause the monitoring hub to establish said wireless communication between the monitoring hub and the wireless physiological sensor based on at least a proximity of the wireless physiological sensor to the monitoring hub.

7. The monitoring hub of claim 1, wherein the one or more hardware computer processors is further configured to execute the plurality of computer executable instructions to cause the monitoring hub to access said wireless configuration data by wirelessly receiving said wireless configuration data from the remote server.

8. The monitoring hub of claim 1, wherein the one or more hardware computer processors is further configured to execute the plurality of computer executable instructions to cause the monitoring hub to access said wireless configuration data based on at least retrieving said wireless configuration data from memory.

9. The monitoring hub of claim 1, wherein the one or more hardware computer processors is further configured to execute the plurality of computer executable instructions to cause the monitoring hub to render the user interface via a display of the monitoring hub.

10. The monitoring hub of claim 1, wherein the one or more hardware computer processors is further configured to execute the plurality of computer executable instructions to cause the monitoring hub to receive historical user interface data from the remote server, the historical user interface data corresponding to the historical physiological data, the historical user interface data previously generated by the electronic device.

* * * * *